United States Patent
Shapiro et al.

(10) Patent No.: US 10,029,125 B2
(45) Date of Patent: Jul. 24, 2018

(54) ULTRASONIC SURGICAL INSTRUMENT WITH ARTICULATION JOINT HAVING INTEGRAL STIFFENING MEMBERS

(71) Applicant: Ethicon Endo-Surgery, LLC, Guaynabo, PR (US)

(72) Inventors: Cara L. Shapiro, Milford, OH (US); Ryan M. Asher, Cincinnati, OH (US); Kristen Denzinger, Cincinnati, OH (US); William B. Weisenburgh, II, Maineville, OH (US); David J. Cagle, Cincinnati, OH (US); Benjamin D. Dickerson, Cincinnati, OH (US); Barry C. Worrell, Centerville, OH (US); Gregory W. Johnson, Milford, OH (US); Joseph E. Hollo, Liberty Township, OH (US); Jason R. Sullivan, Morrow, OH (US); Tylor C. Muhlenkamp, Cincinnati, OH (US); Stephen J. Balek, Springboro, OH (US)

(73) Assignee: Ethicon LLC, Guaynabo, PR (US)

( * ) Notice: Subject to any disclaimer, the term of this patent is extended or adjusted under 35 U.S.C. 154(b) by 318 days.

(21) Appl. No.: 14/688,424

(22) Filed: Apr. 16, 2015

(65) Prior Publication Data
US 2016/0303403 A1 Oct. 20, 2016

(51) Int. Cl.
*A61B 17/28* (2006.01)
*A61N 7/02* (2006.01)
(Continued)

(52) U.S. Cl.
CPC .............. *A61N 7/02* (2013.01); *A61B 17/295* (2013.01); *A61B 17/320068* (2013.01);
(Continued)

(58) Field of Classification Search
CPC ............ A61N 7/02; A61B 2018/00607; A61B 2017/2946; A61B 2017/2927;
(Continued)

(56) References Cited

U.S. PATENT DOCUMENTS

| 5,322,055 A | 6/1994 | Davison et al. |
|---|---|---|
| 5,873,873 A | 2/1999 | Smith et al. |

(Continued)

OTHER PUBLICATIONS

U.S. Appl. No. 14/258,179, filed Apr. 22, 2014.
(Continued)

*Primary Examiner* — Michael Carey
(74) *Attorney, Agent, or Firm* — Frost Brown Todd LLC

(57) ABSTRACT

A surgical apparatus comprises a body, an ultrasonic transducer, a shaft, an acoustic waveguide, an articulation section, an end effector, and a rigidizing member. The ultrasonic transducer is operable to convert electrical power into ultrasonic vibrations. The shaft couples the end effector and the body together. The acoustic waveguide is coupled with the transducer. The articulation section is operable to flex to thereby deflect the end effector from a longitudinal axis defined by the shaft. The rigidizing member is operable to selectively rigidize the articulation section and thereby prevent deflection of the end effector by preventing flexibility of the articulation section. Such rigidization includes removing any "play" or other small movement that might otherwise be provided by the articulation section due to manufacturing tolerances and/or looseness between parts.

20 Claims, 47 Drawing Sheets

(51) Int. Cl.
*A61B 17/295* (2006.01)
*A61B 17/32* (2006.01)
*A61B 17/00* (2006.01)
*A61B 17/29* (2006.01)
*A61B 18/00* (2006.01)

(52) U.S. Cl.
CPC ...... *A61B 17/320092* (2013.01); *A61B 2017/003* (2013.01); *A61B 2017/00309* (2013.01); *A61B 2017/00314* (2013.01); *A61B 2017/00327* (2013.01); *A61B 2017/00336* (2013.01); *A61B 2017/2927* (2013.01); *A61B 2017/2946* (2013.01); *A61B 2018/00607* (2013.01)

(58) Field of Classification Search
CPC .... A61B 2017/00336; A61B 2017/00327; A61B 2017/00314; A61B 2017/00309; A61B 2017/003; A61B 17/320092; A61B 17/320068; A61B 17/295
USPC .......................................... 606/41, 46, 47, 34
See application file for complete search history.

(56) References Cited

U.S. PATENT DOCUMENTS

| | | | |
|---|---|---|---|
| 5,897,523 A | 4/1999 | Wright et al. | |
| 5,980,510 A | 11/1999 | Tsonton et al. | |
| 5,989,264 A | 11/1999 | Wright | |
| 6,063,098 A | 5/2000 | Houser et al. | |
| 6,090,120 A | 7/2000 | Wright et al. | |
| 6,325,811 B1 | 12/2001 | Messerly | |
| 6,454,782 B1 | 9/2002 | Schwemberger | |
| 6,589,200 B1 | 7/2003 | Schwemberger et al. | |
| 6,752,815 B2 | 6/2004 | Beaupre | |
| 6,773,444 B2 | 8/2004 | Messerly | |
| 6,783,524 B2 | 8/2004 | Anderson et al. | |
| 7,135,030 B2 | 11/2006 | Schwemberger et al. | |
| 7,288,075 B2 | 10/2007 | Parihar et al. | |
| 7,621,930 B2 | 11/2009 | Houser | |
| 8,105,350 B2 | 1/2012 | Lee et al. | |
| 8,461,744 B2 | 6/2013 | Wiener et al. | |
| 8,550,989 B2 | 10/2013 | Dohi et al. | |
| 8,574,263 B2 | 11/2013 | Mueller | |
| 8,591,536 B2 | 11/2013 | Robertson | |
| 8,623,027 B2 | 1/2014 | Price et al. | |
| 8,906,019 B2 | 12/2014 | Mueller | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 2006/0079874 A1 | 4/2006 | Faller et al. | |
| 2007/0191713 A1 | 8/2007 | Eichmann et al. | |
| 2007/0219550 A1 | 9/2007 | Thompson et al. | |
| 2007/0282333 A1 | 12/2007 | Fortson et al. | |
| 2008/0200940 A1 | 8/2008 | Eichmann et al. | |
| 2010/0324370 A1* | 12/2010 | Dohi ................. | A61B 1/00078 600/144 |
| 2012/0078247 A1 | 3/2012 | Worrell et al. | |
| 2012/0112687 A1 | 5/2012 | Houser et al. | |
| 2012/0116265 A1 | 5/2012 | Houser et al. | |
| 2012/0179151 A1* | 7/2012 | Mueller ................ | A61B 17/29 606/33 |
| 2013/0023923 A1* | 1/2013 | Mueller ................ | A61B 17/29 606/205 |
| 2013/0289592 A1 | 10/2013 | Stulen et al. | |
| 2014/0005701 A1 | 1/2014 | Olson et al. | |
| 2014/0005703 A1 | 1/2014 | Stulen et al. | |
| 2015/0080924 A1 | 3/2015 | Stulen et al. | |

OTHER PUBLICATIONS

U.S. Appl. No. 61/410,603, filed Nov. 5, 2010.
International Search Report and Written Opinion dated Oct. 31, 2016 re Application No. PCT/US16/27672.
International Search Report and Written Opinion dated Jul. 7, 2016 for Application No. PCT/US2016/027672, 11 pgs.

* cited by examiner

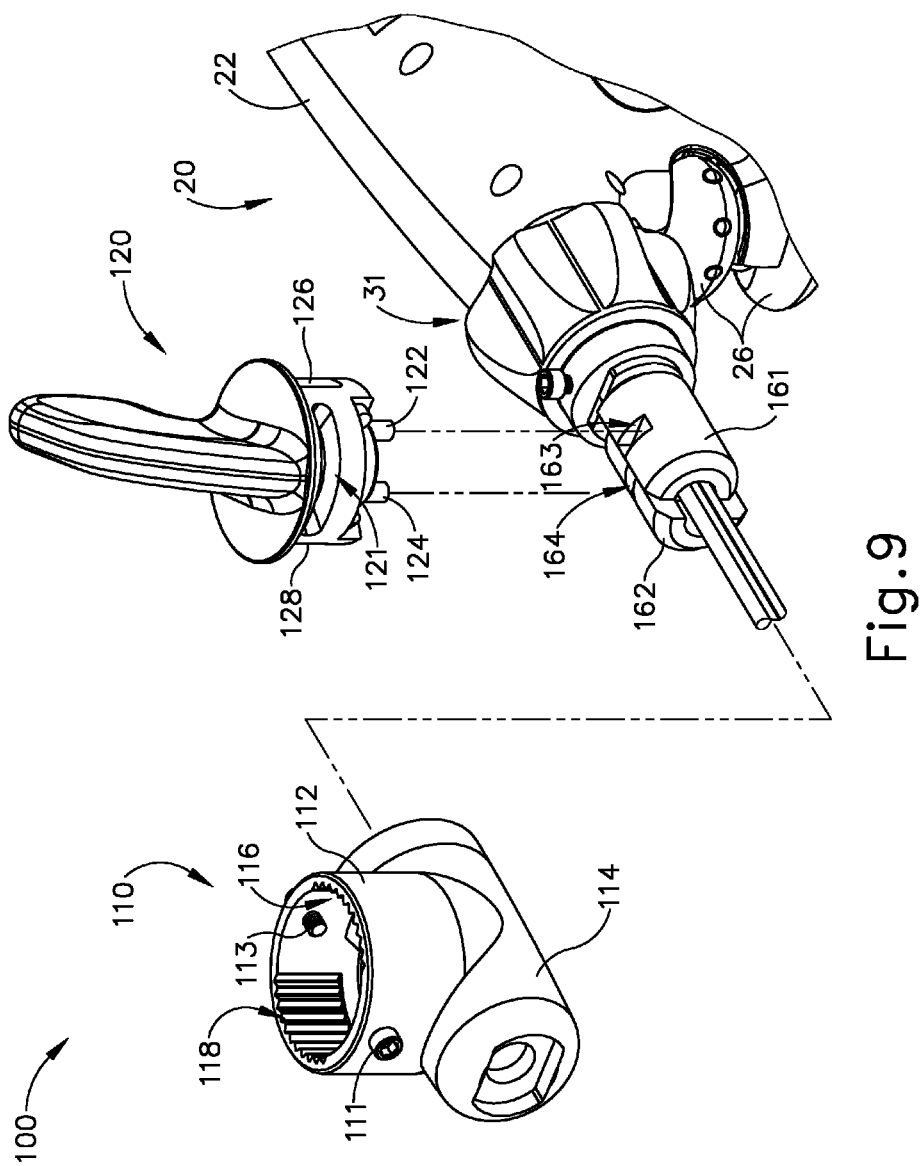

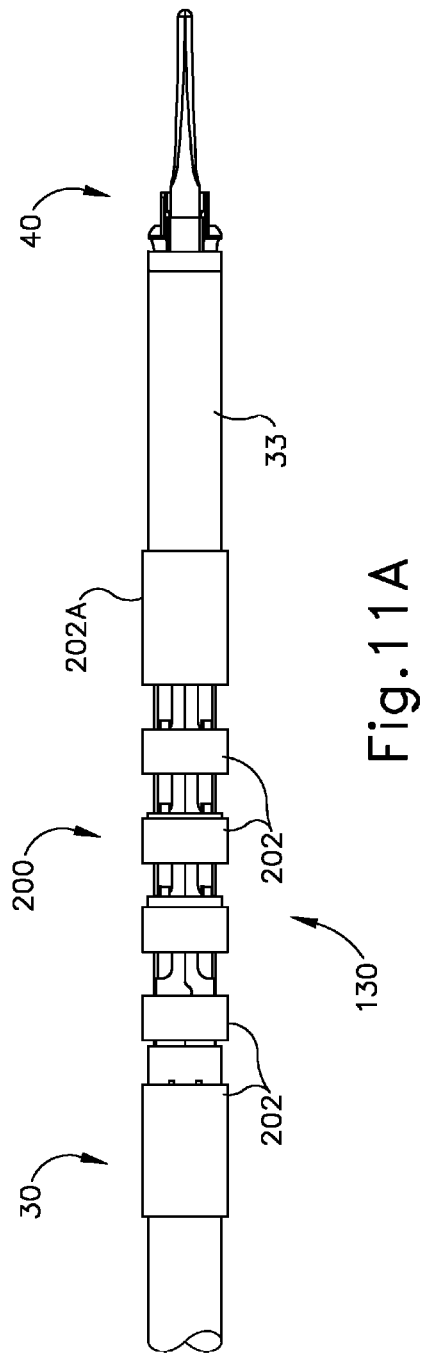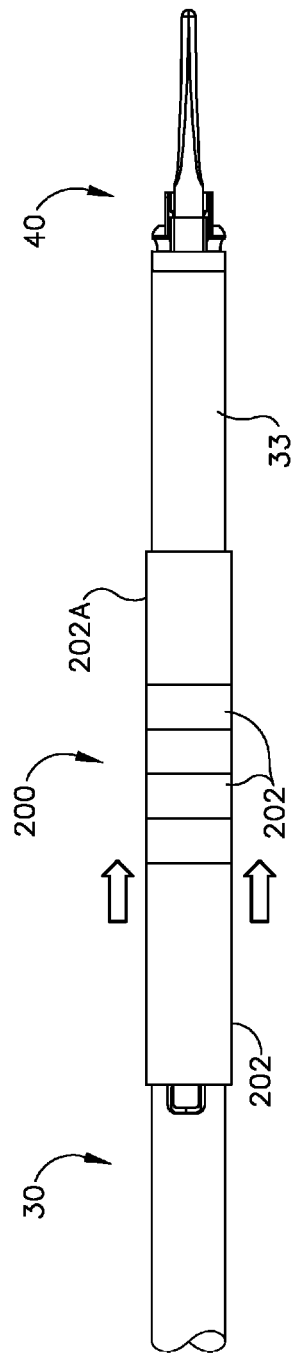
Fig.11A
Fig.11B

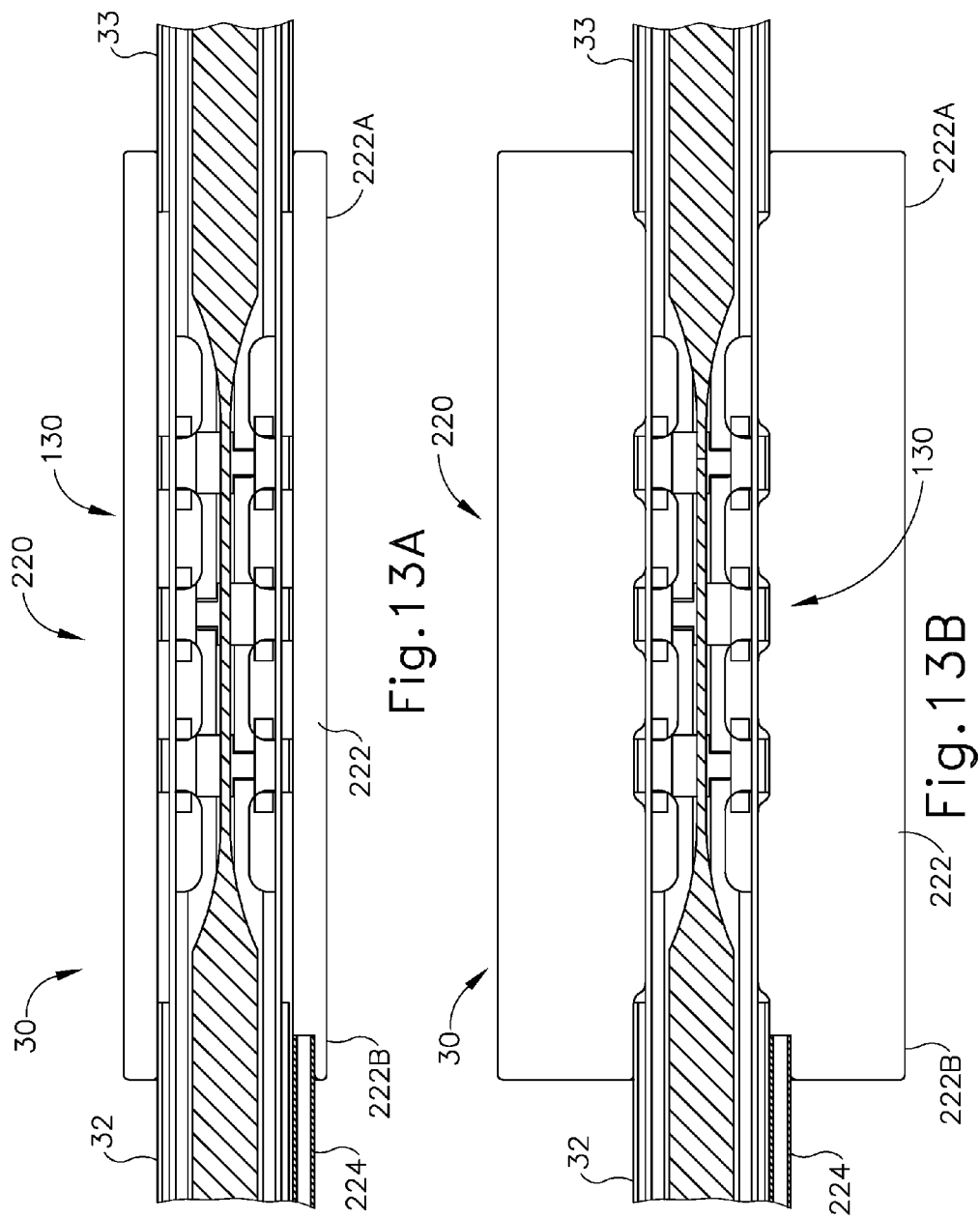

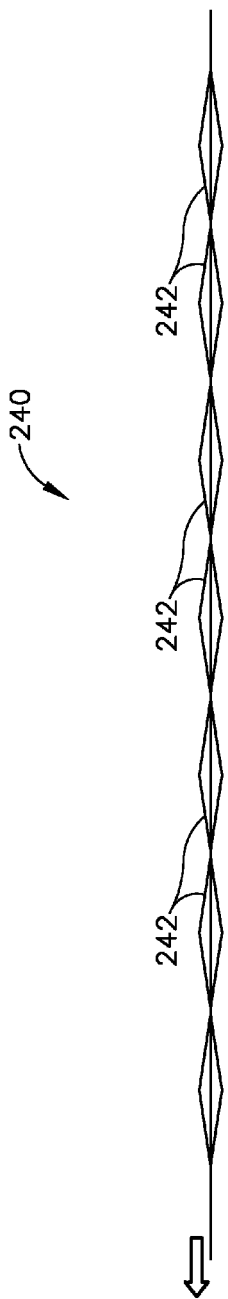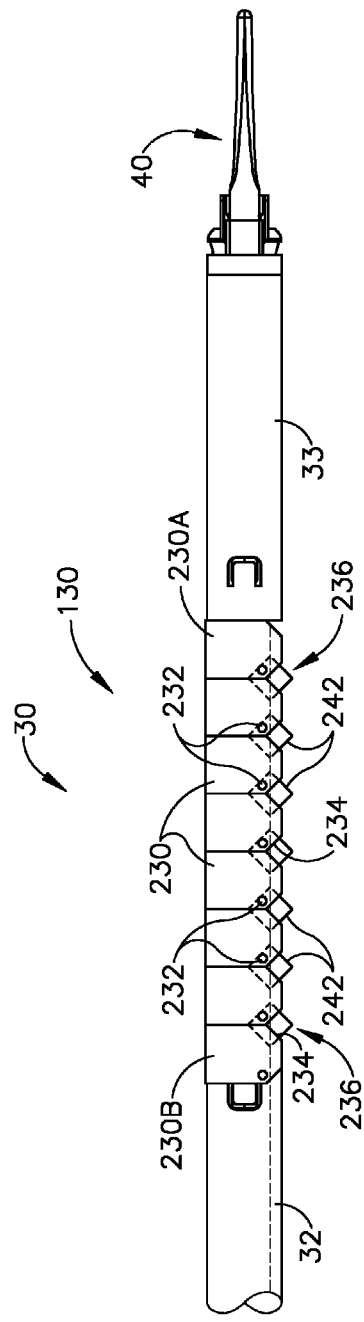
Fig.15B
Fig.16

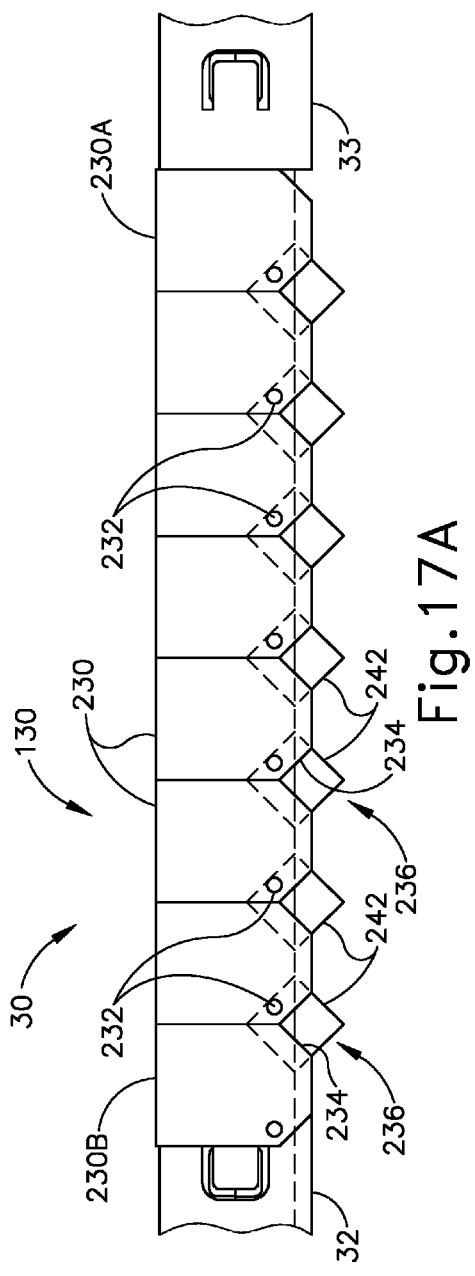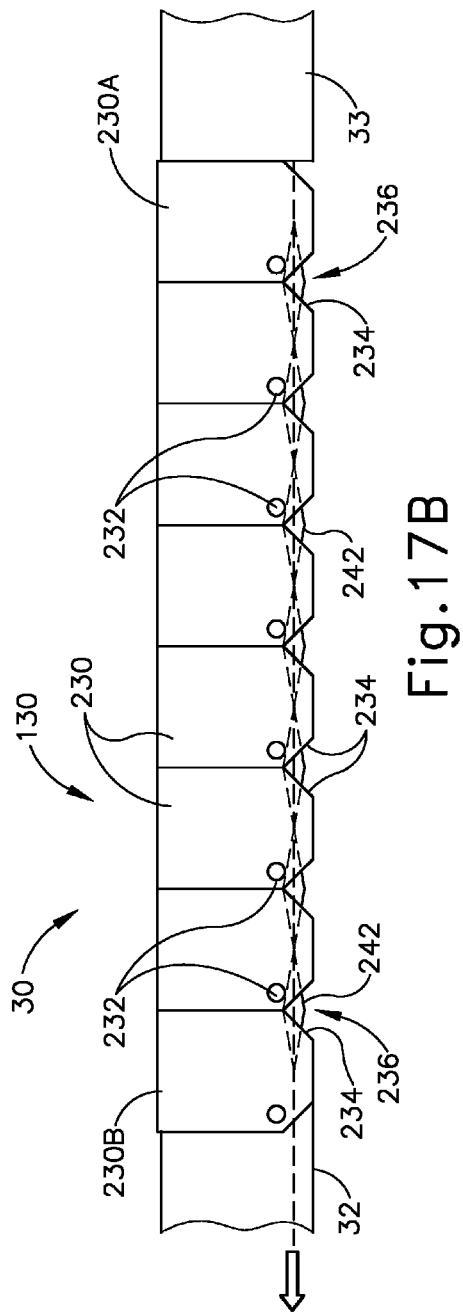

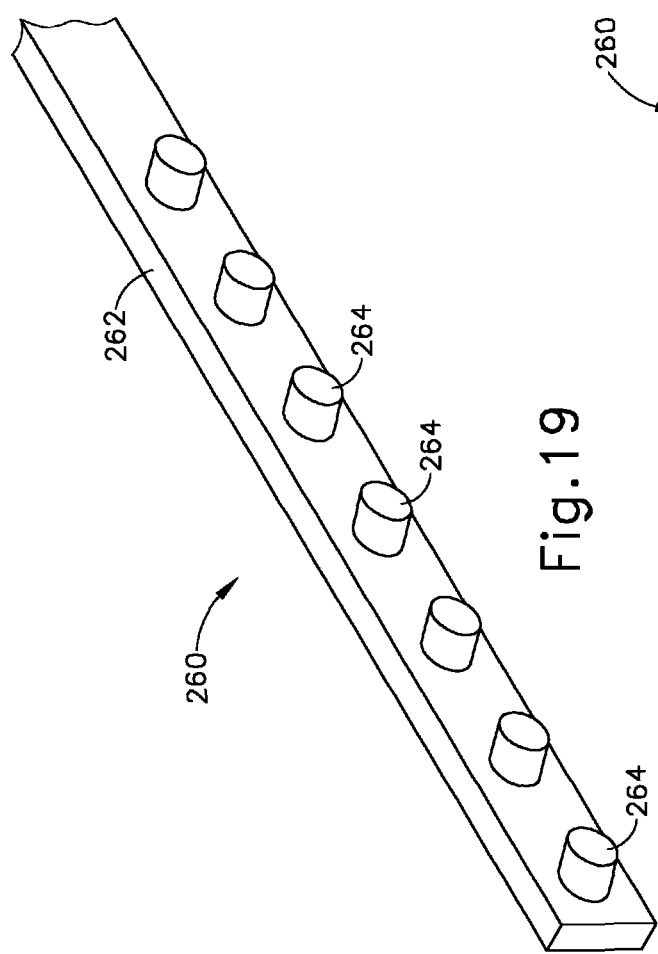
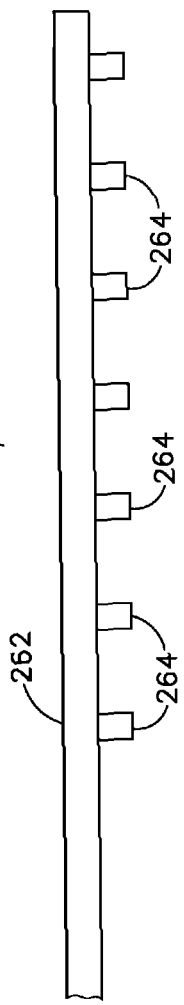
Fig.19
Fig.20

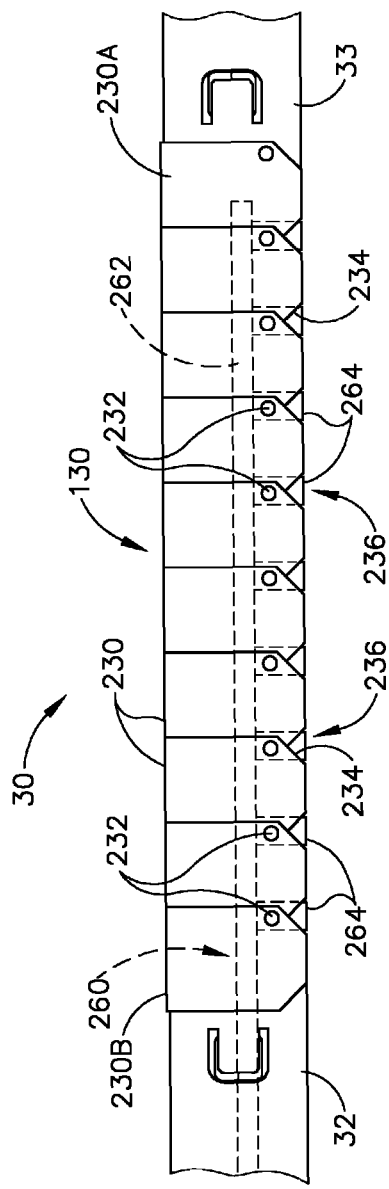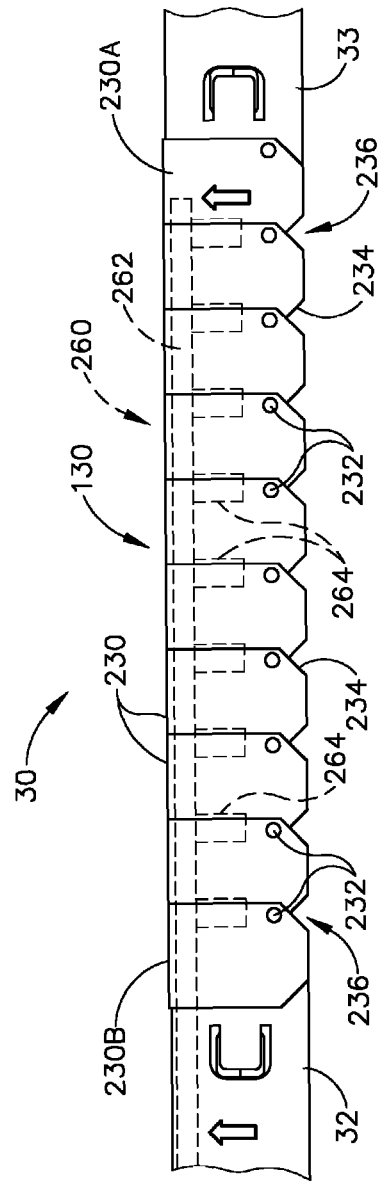

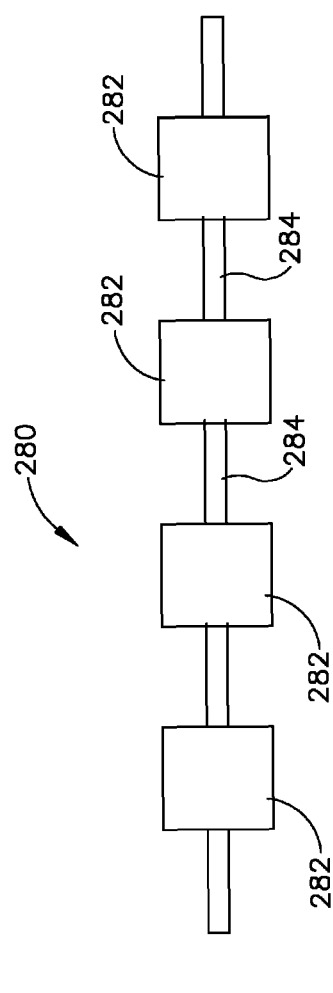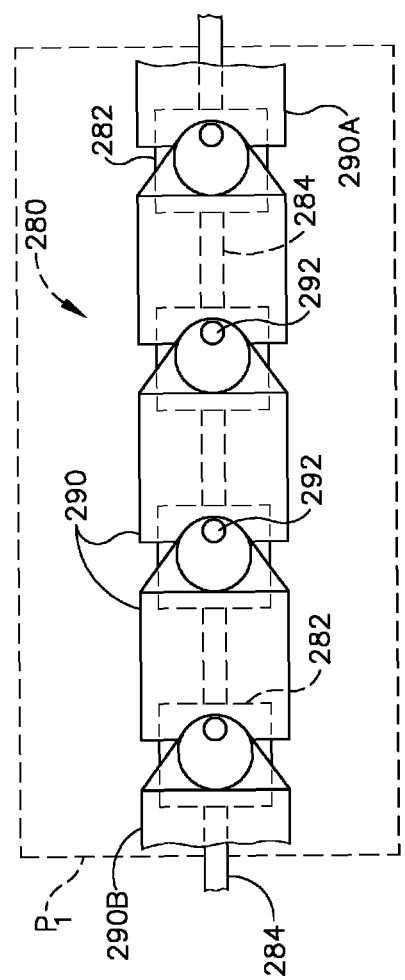

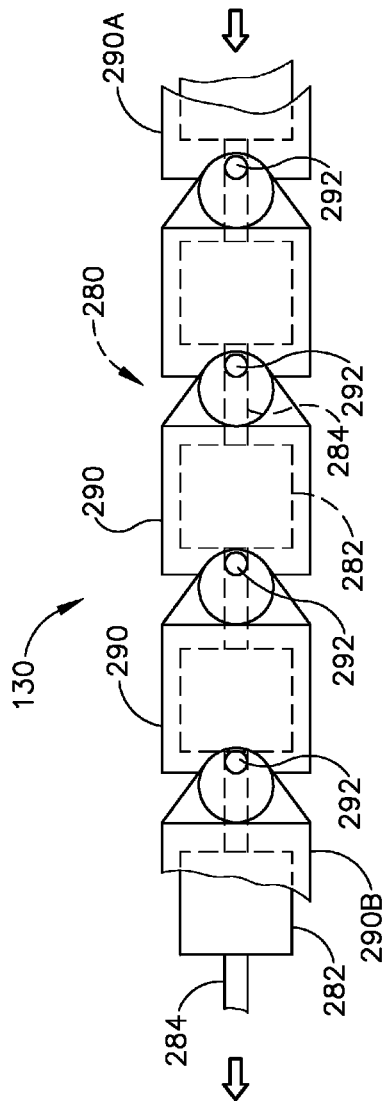
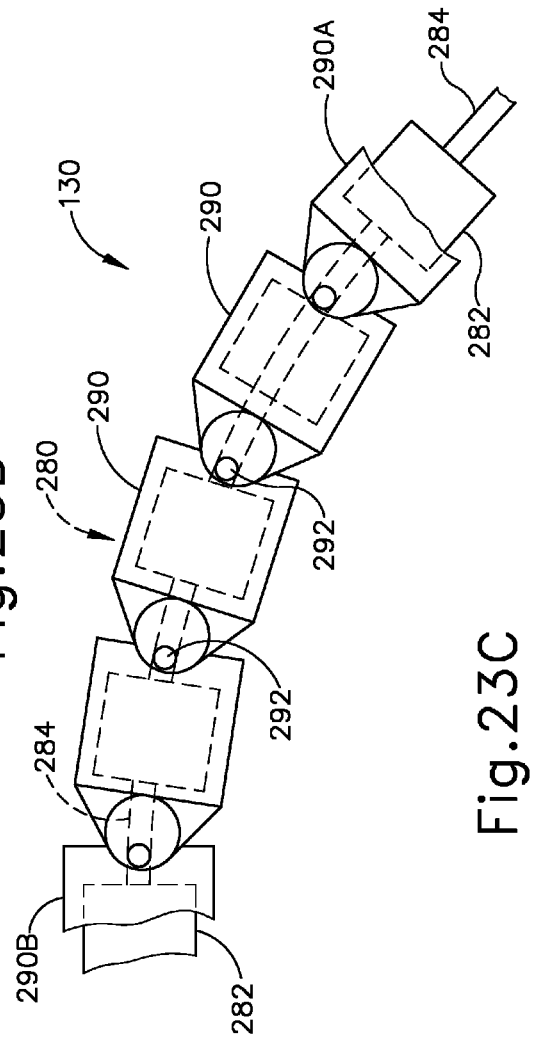
Fig.23B
Fig.23C

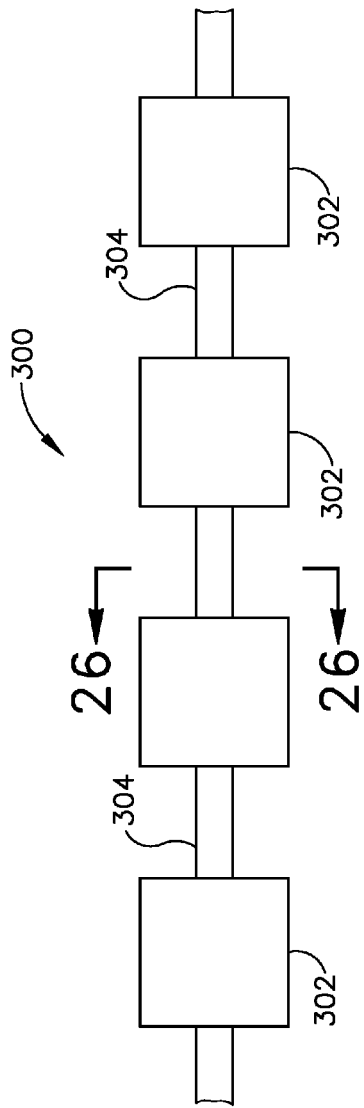
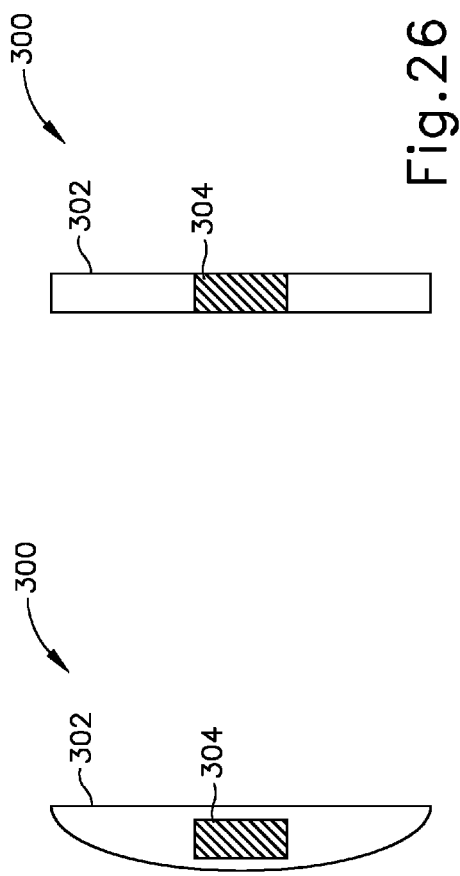

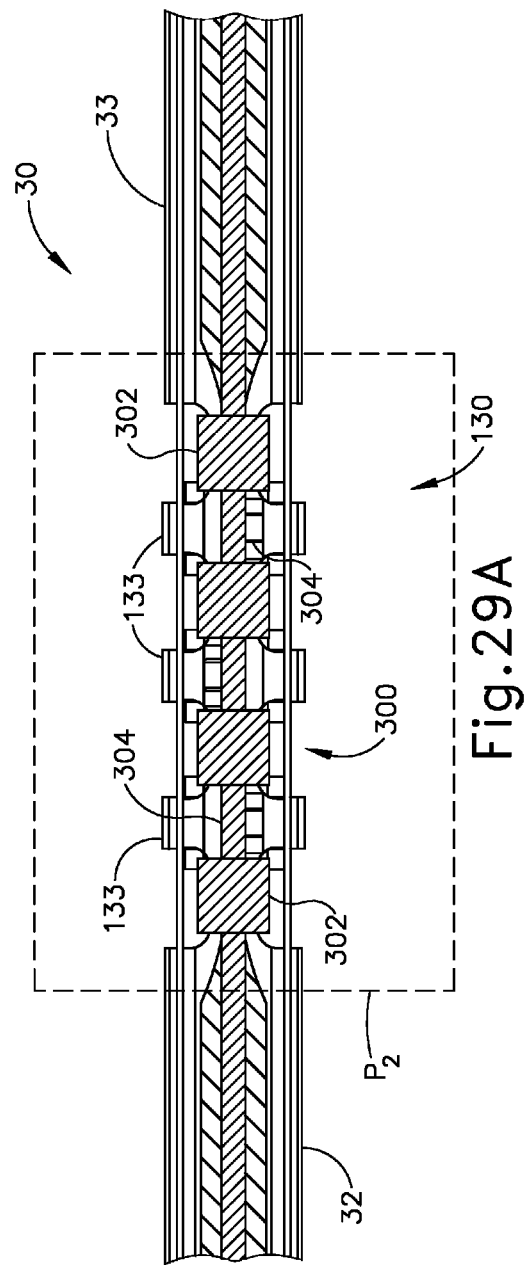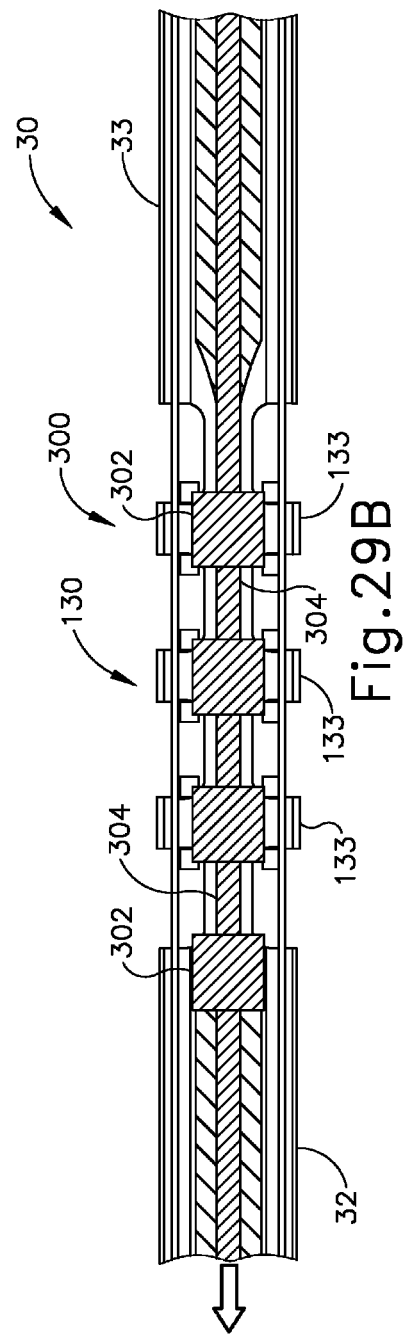

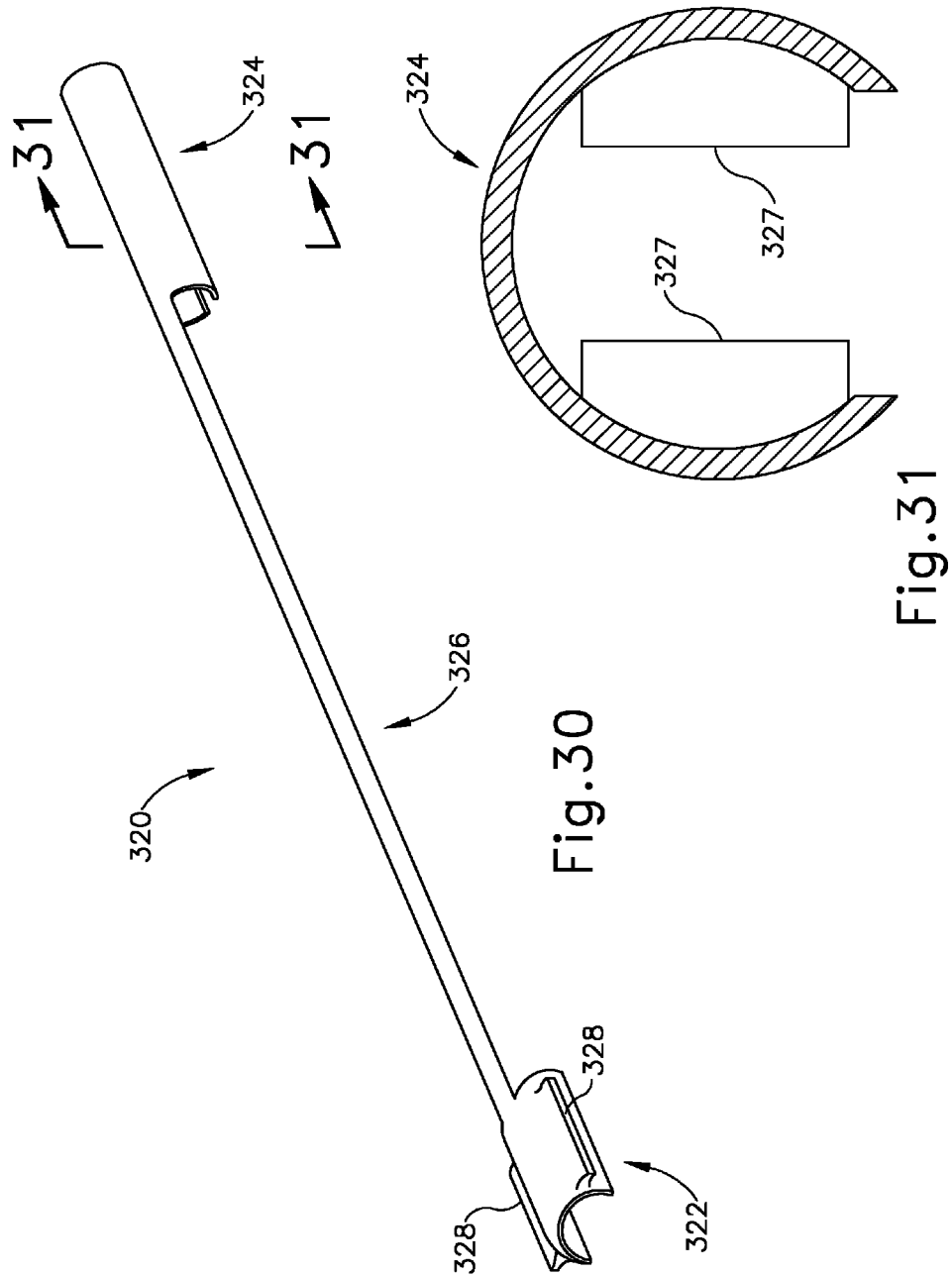

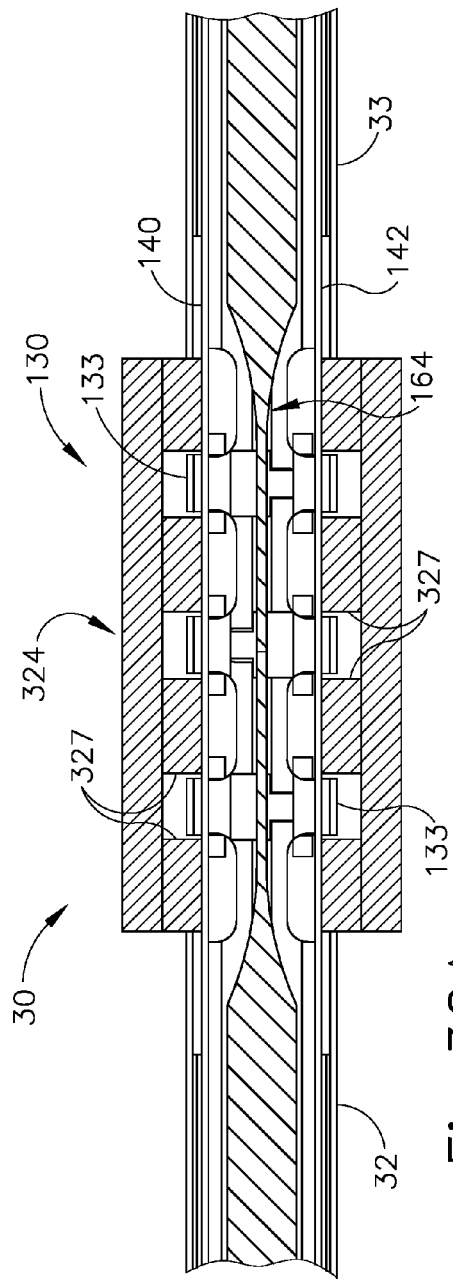
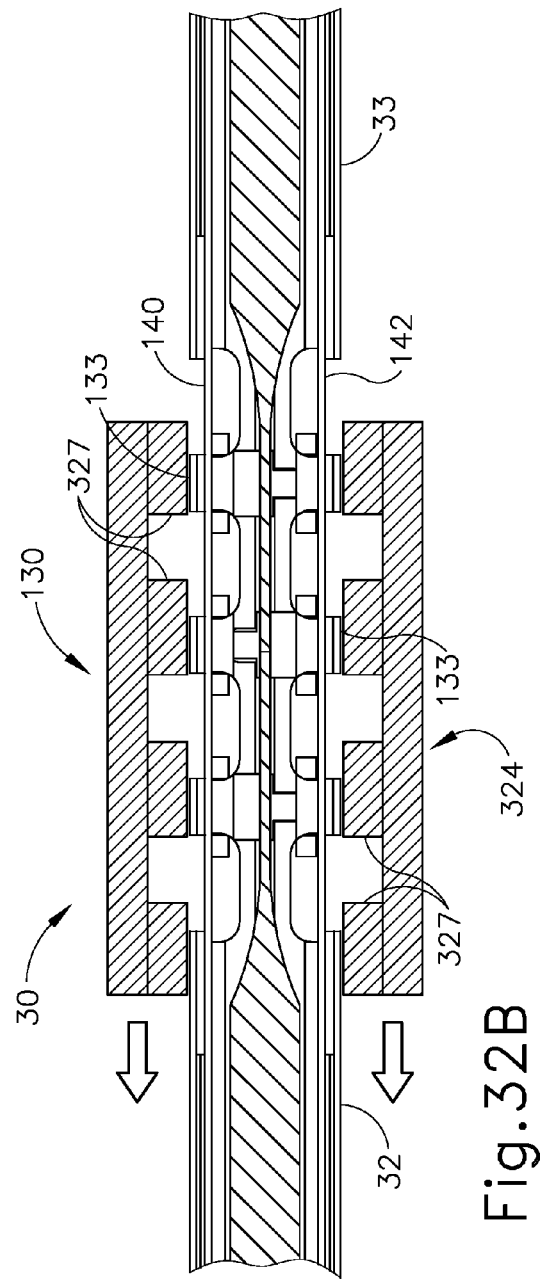
Fig. 32A
Fig. 32B

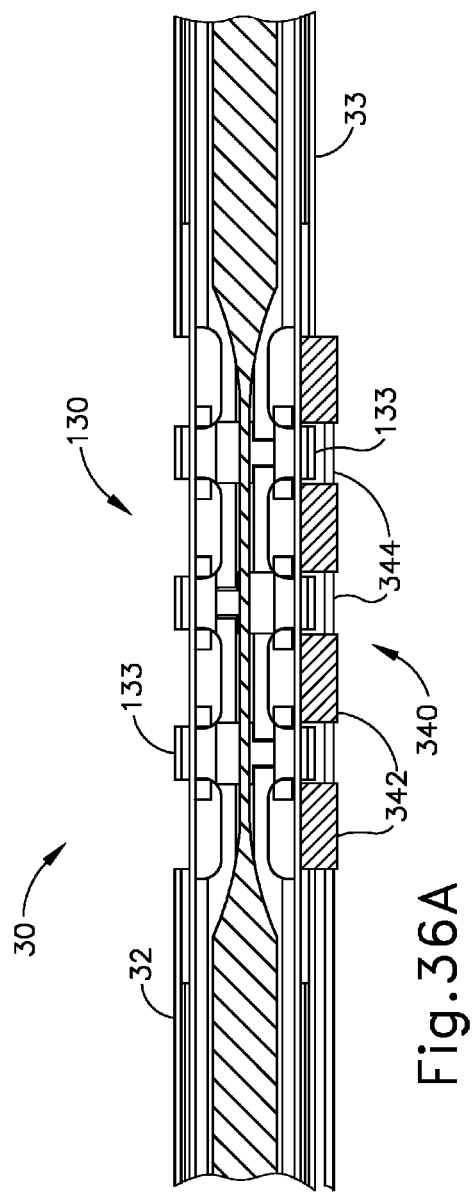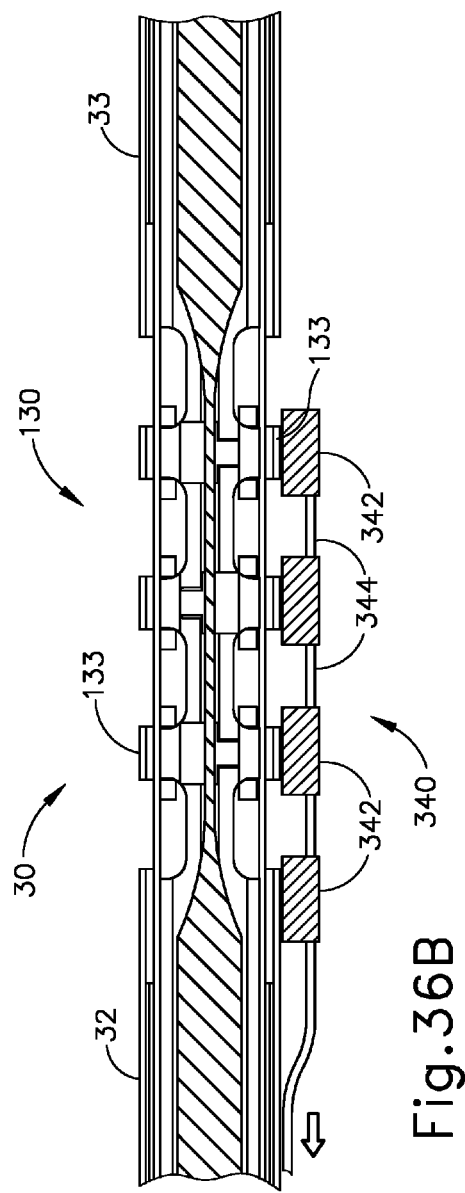

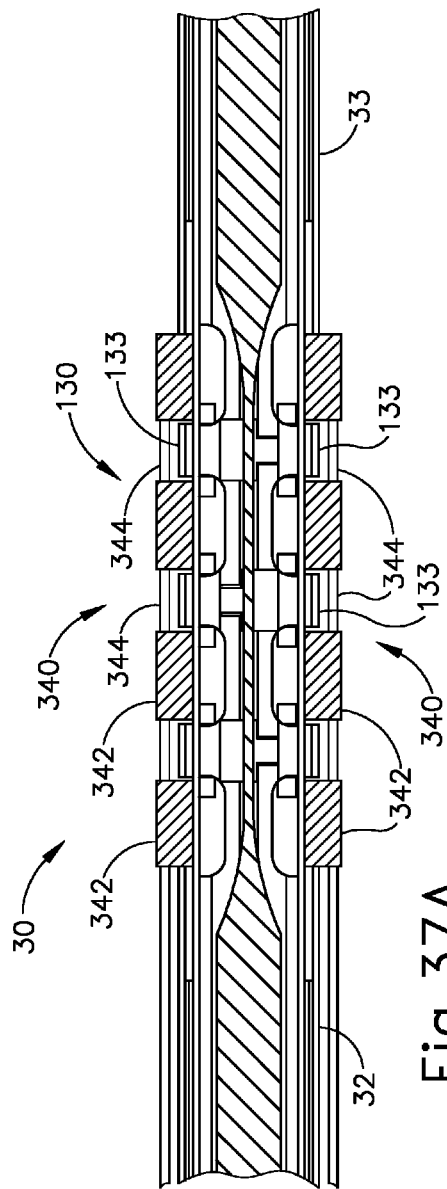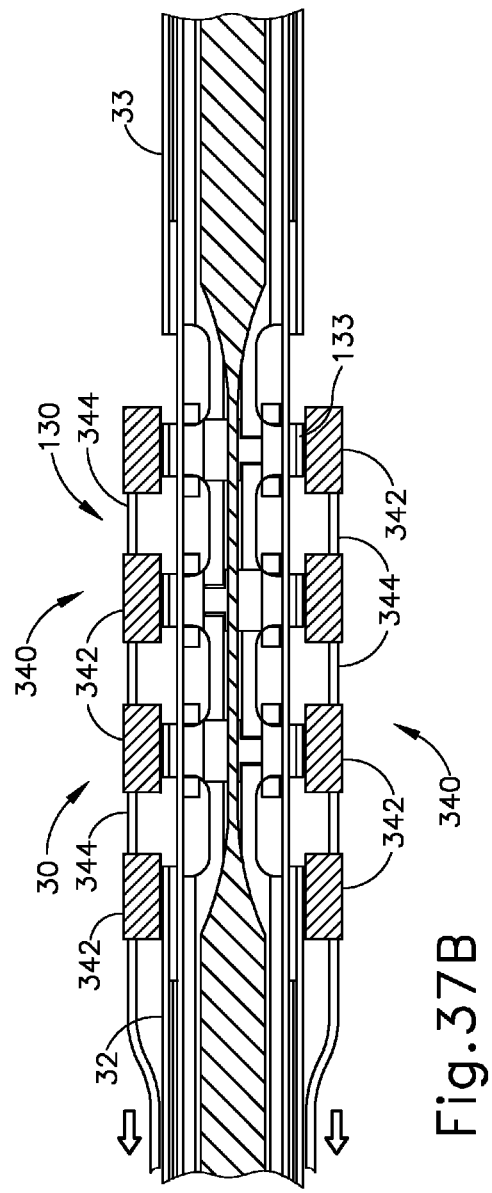

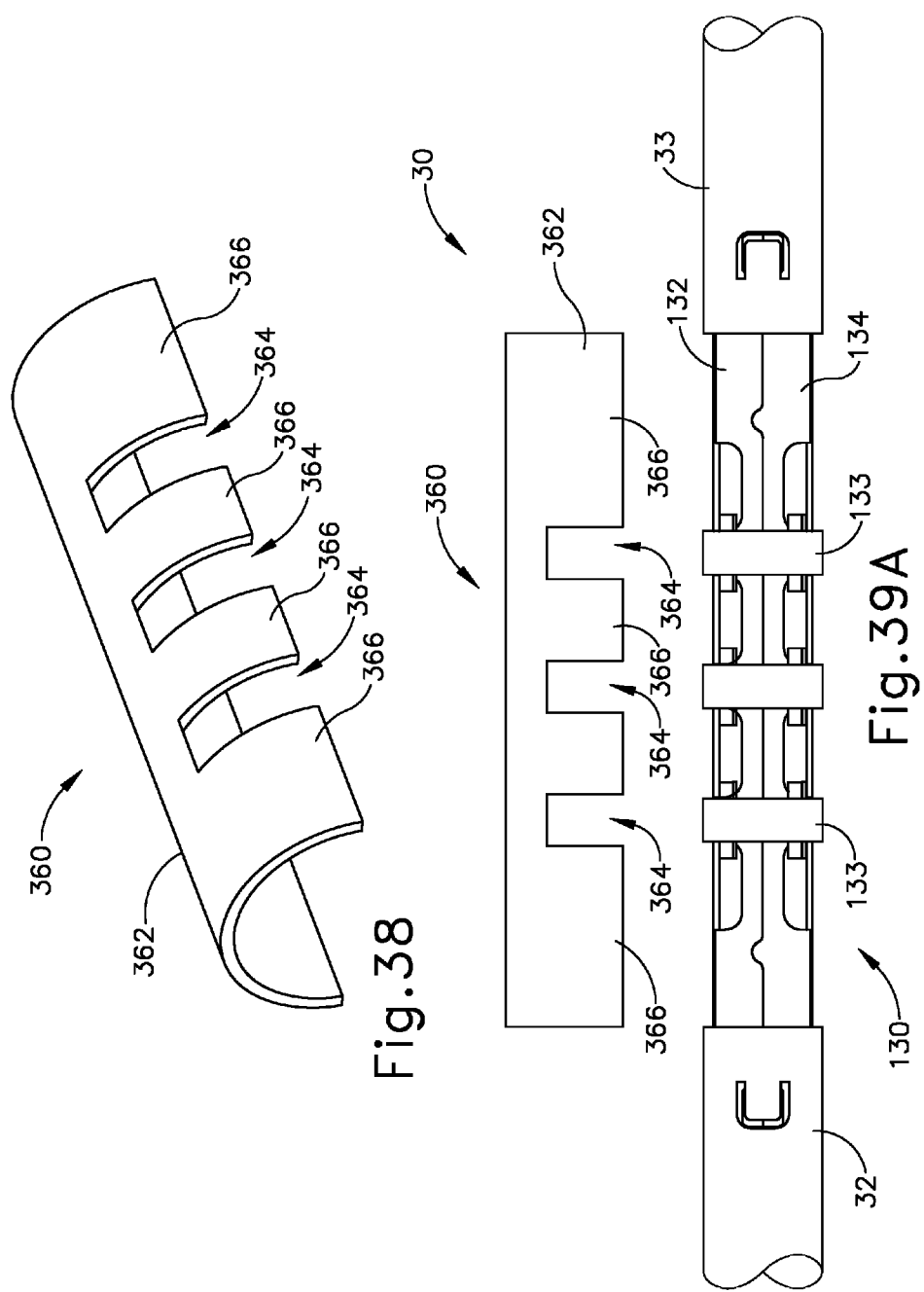

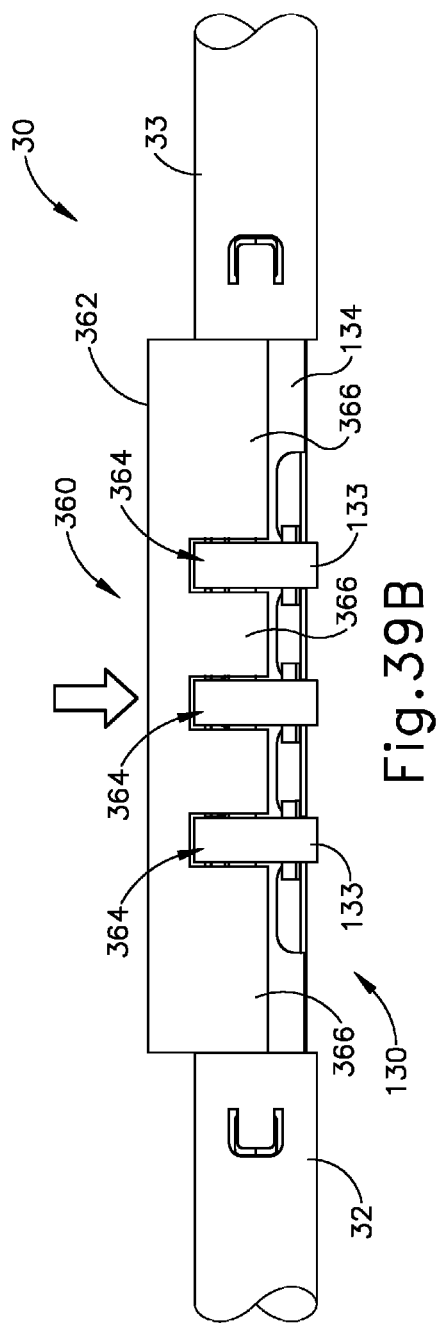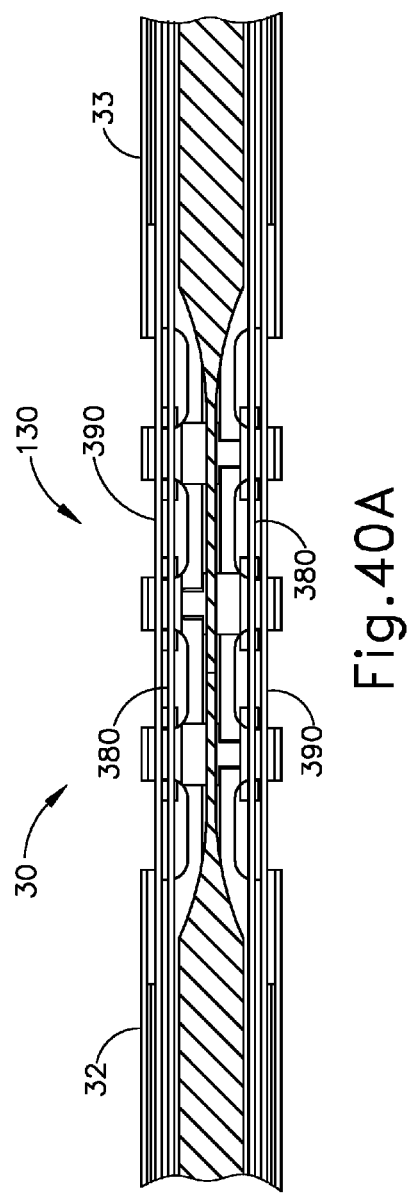

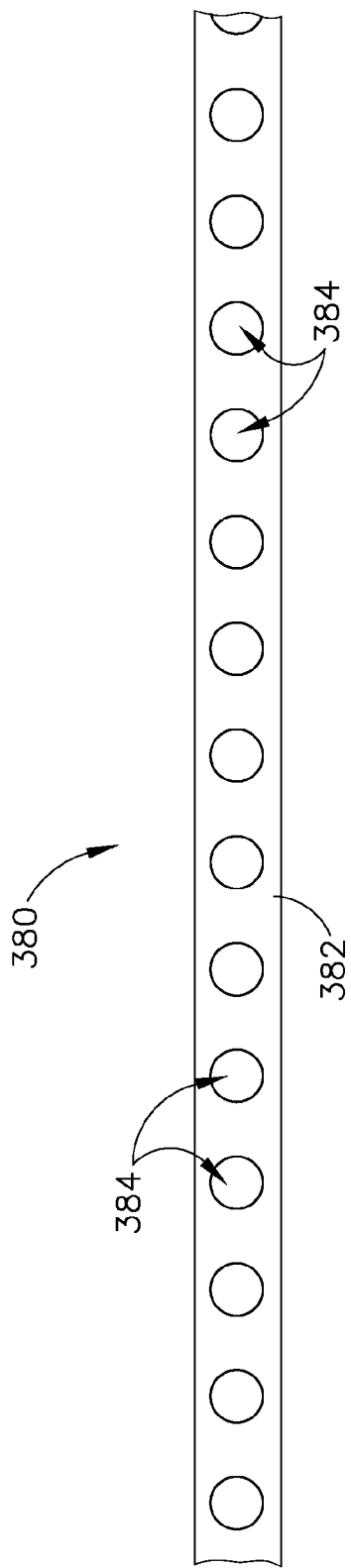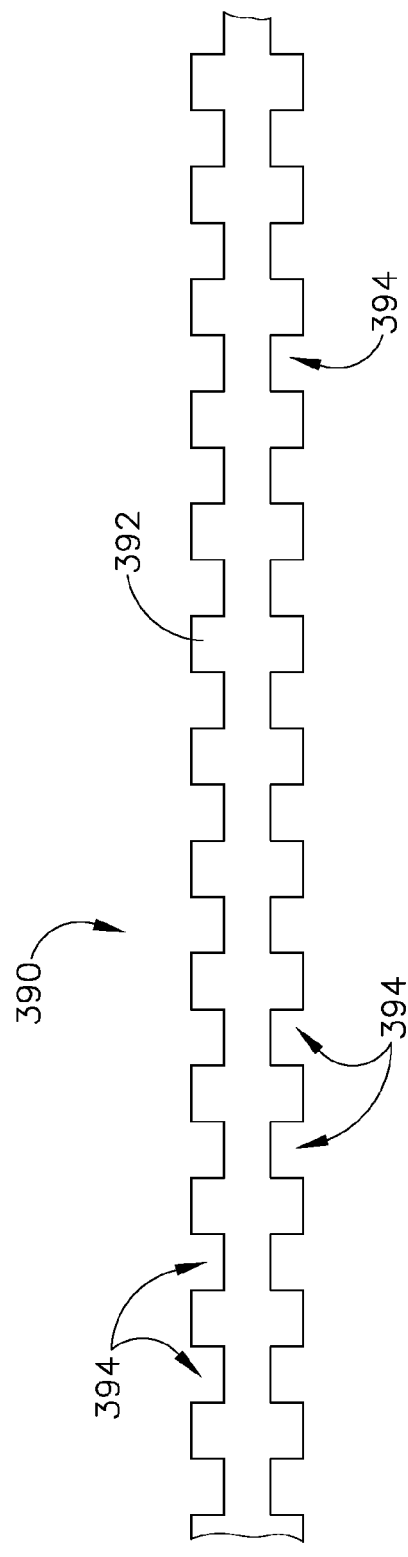

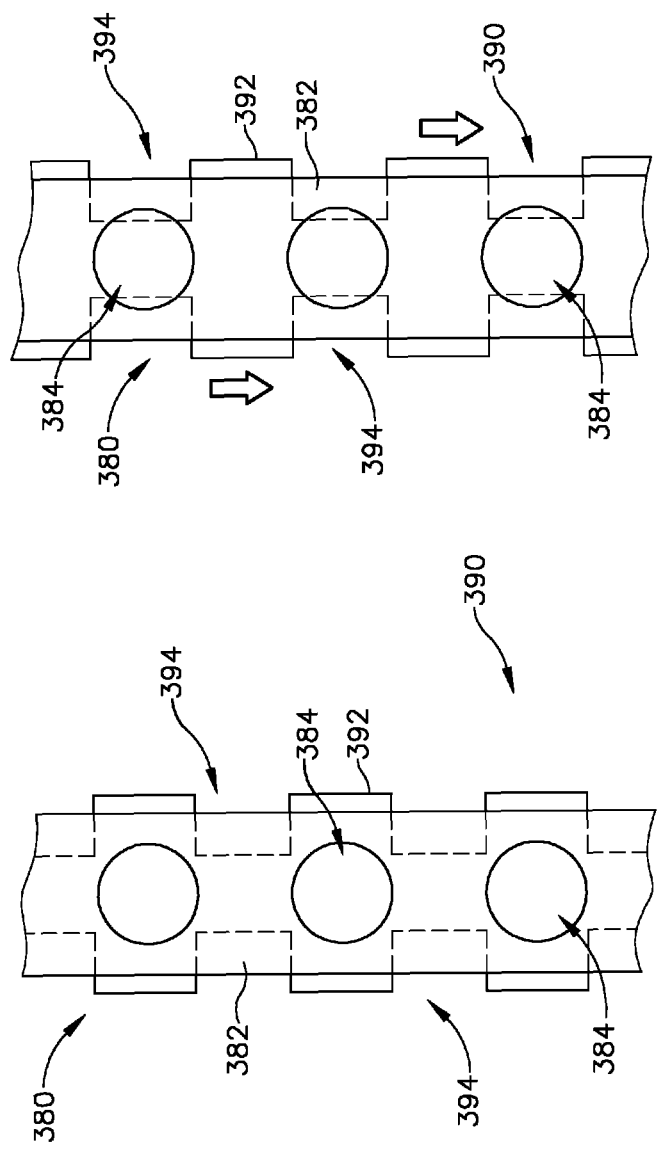

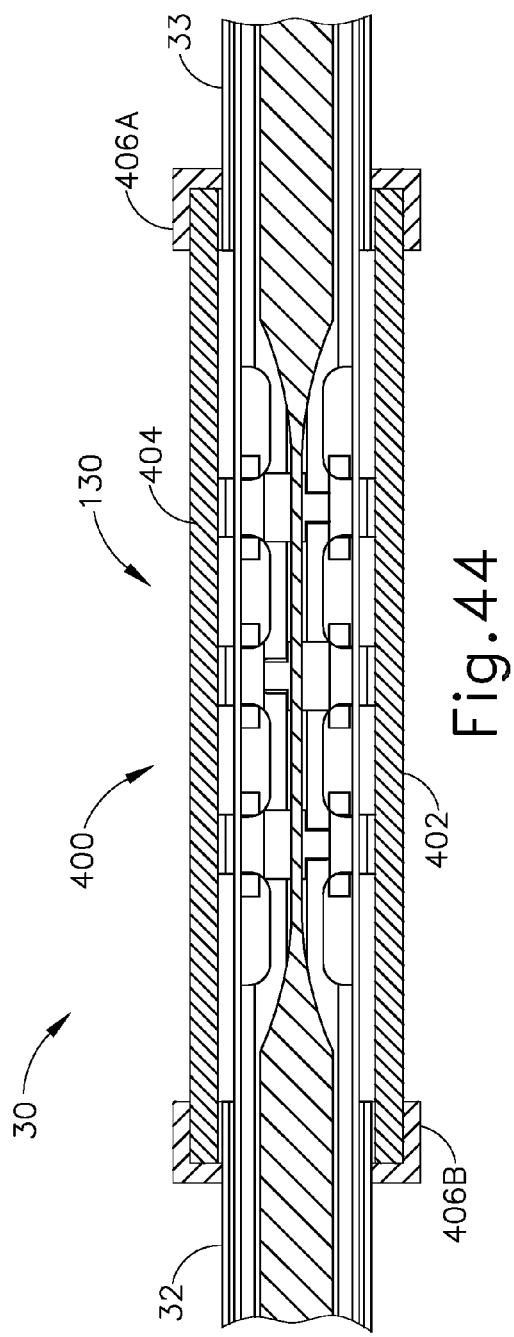
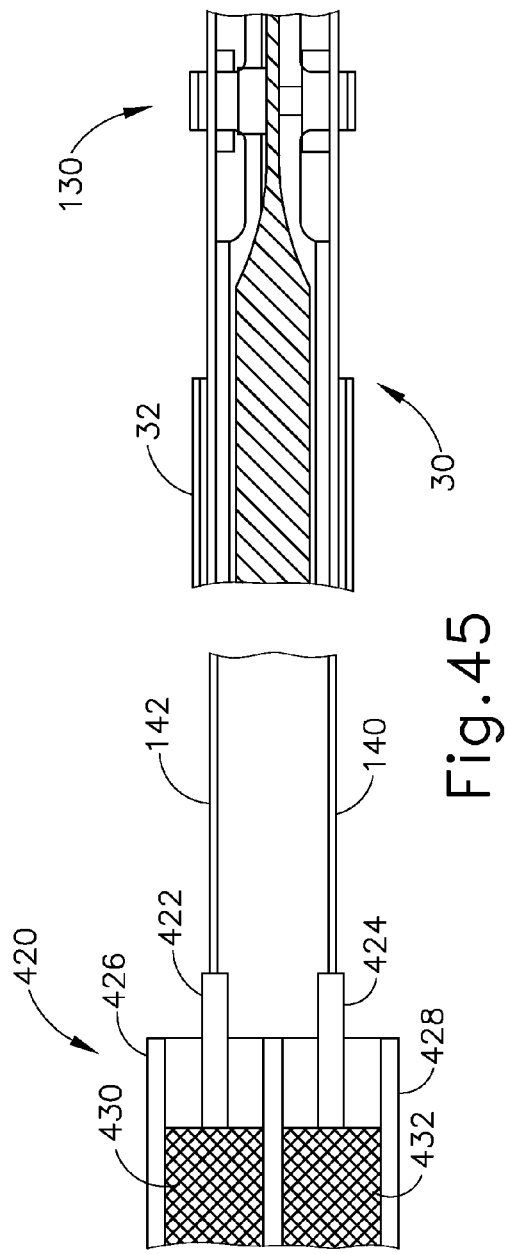
Fig. 44
Fig. 45

ULTRASONIC SURGICAL INSTRUMENT WITH ARTICULATION JOINT HAVING INTEGRAL STIFFENING MEMBERS

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012 now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, entitled "Surgical Instruments with Articulating Shafts," issued as U.S. Pat. No. 9,393,037 on Jul. 19, 2016 the disclosure of which is incorporated by reference herein; U.S. Pub. No. 2014/0005703, entitled "Surgical Instruments with Articulating Shafts," published Jan. 2, 2014, issued as U.S. Pat. No. 9,408,622 on Aug. 9, 2016, the disclosure of which is incorporated by reference herein; U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein; U.S. Pub. No. 2015/0080924, entitled "Articulation Features for Ultrasonic Surgical Instrument," published Mar. 19, 2015, the disclosure of which is incorporated by reference herein; and U.S. patent application Ser. No. 14/258,179, entitled Ultrasonic Surgical Device with Articulating End Effector," filed Apr. 22, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 9 depicts a partially exploded perspective view of an articulation control assembly of the instrument of FIG. 1;

FIG. 11A depicts a top plan view of a modified version of the shaft assembly and end effector of FIG. 2 having an exemplary structural feature in a spaced-apart orientation;

FIG. 11B depicts a top plan view of the modified shaft assembly and end effector of FIG. 11A with the structural feature of FIG. 11A in a closed orientation;

FIG. 13A depicts a cross-sectional top view of the modified shaft assembly and end effector of FIG. 12 in a straight configuration with the structural feature of FIG. 12 deflated;

FIG. 13B depicts a cross-sectional top view of the modified shaft assembly and end effector of FIG. 12 in a straight configuration with the structural feature of FIG. 12 inflated;

FIG. 15B depicts a top plan view of the structural feature of FIG. 15A in an expanded configuration;

FIG. 16 depicts a top view of the shaft assembly and end effector of FIG. 14 in a straight configuration with the structural feature of FIG. 15A in the contracted configuration positioned therein;

FIG. 17A depicts detailed a top view of the shaft assembly of FIG. 14 in a straight configuration with the structural feature of FIG. 15A in the contracted configuration positioned therein;

FIG. 17B depicts detailed a top view of the shaft assembly of FIG. 14 in a straight configuration with the structural feature of FIG. 15A in the expanded configuration positioned therein;

FIG. 19 depicts a perspective view of yet another exemplary structural feature that may be incorporated into the shaft assembly and end effector of FIG. 14;

FIG. 20 depicts a top plan view of the structural feature of FIG. 19;

FIG. 21A depicts detailed a top view of the shaft assembly of FIG. 14 in a straight configuration with the structural feature of FIG. 19 positioned therein in a first lateral position;

FIG. 21B depicts detailed a top view of the shaft assembly of FIG. 14 in a straight configuration with the structural feature of FIG. 19 positioned therein and moved to a second lateral position;

FIG. 22 depicts a top plan view of yet another exemplary structural feature that may be incorporated into the shaft assembly of FIG. 2;

FIG. 23A depicts a detailed top plan view of a modified version of the shaft assembly of FIG. 2 having a plurality of linkage members in a straight configuration with the structural feature of FIG. 22 positioned therein in a distal longitudinal position;

FIG. 23B depicts a detailed top plan view of the modified shaft assembly of FIG. 23A having a plurality of linkage members in a straight configuration with the structural feature of FIG. 22 positioned therein and moved into a proximal longitudinal position;

FIG. 23C depicts a detailed top plan view of the modified shaft assembly of FIG. 23A having a plurality of linkage members in an articulated configuration with the structural feature of FIG. 22 positioned therein in the proximal longitudinal position;

FIG. 25 depicts a top plan view of the structural feature of FIG. 24;

FIG. 26 depicts a cross-sectional front view of the stiffening feature of FIG. 24, taken along line 26-26 of FIG. 25;

FIG. 27 depicts an exemplary alternative cross-sectional front view of the stiffening feature of FIG. 24;

FIG. 29A depicts a detailed cross-sectional top plan view of the modified shaft assembly of FIG. 24 in a straight configuration with the structural feature of FIG. 24 positioned therein in a distal longitudinal position;

FIG. 29B depicts a detailed cross-sectional top plan view of the modified shaft assembly of FIG. 24 in a straight configuration with the structural feature of FIG. 24 positioned therein and moved into a proximal longitudinal position;

FIG. 30 depicts a perspective view of yet another exemplary structural feature that may be incorporated into the shaft assembly of FIG. 2;

FIG. 31 depicts a cross-sectional front view of the rigidizing member of FIG. 30, taken along line 31-31 of FIG. 30;

FIG. 32A depicts a detailed cross-sectional top plan view of a modified version of the shaft assembly of FIG. 2 in a straight configuration with the structural feature of FIG. 30 positioned thereabout in a distal longitudinal position;

FIG. 32B depicts a detailed cross-sectional top plan view of the modified shaft assembly of FIG. 32A in a straight configuration with the structural feature of FIG. 30 positioned thereabout and moved into a proximal longitudinal position;

FIG. 36A depicts a detailed cross-sectional top plan view of a modified version of the shaft assembly of FIG. 2 in a straight configuration with the structural feature of FIG. 33 positioned thereabout in a distal longitudinal position;

FIG. 36B depicts a detailed cross-sectional top plan view of the modified shaft assembly of FIG. 36A in a straight configuration with the structural feature of FIG. 33 positioned thereabout and moved into a proximal longitudinal position;

FIG. 37A depicts a detailed cross-sectional top plan view of the modified shaft assembly of FIG. 36A in a straight configuration with a pair of the structural features of FIG. 33 positioned thereabout in a distal longitudinal position;

FIG. 37B depicts a detailed cross-sectional top plan view of the modified shaft assembly of FIG. 36A in a straight configuration with a pair of the structural features of FIG. 33 positioned thereabout and moved into a proximal longitudinal position;

FIG. 38 depicts a perspective view of yet another exemplary structural feature that may be incorporated into the shaft assembly of FIG. 2;

FIG. 39A depicts a detailed top plan view of the shaft assembly of FIG. 2 with the structural feature of FIG. 38 spaced apart therefrom;

FIG. 39B depicts a detailed top plan view of the shaft assembly of FIG. 2 with the structural feature of FIG. 38 positioned thereabout;

FIG. 40A depicts a detailed cross-sectional top plan view of a modified version of the shaft assembly of FIG. 2 having a pair of exemplary structural articulation bands in a straight configuration;

FIG. 41 depicts a side elevation view of an articulation band of the modified shaft assembly of FIG. 40A;

FIG. 42 depicts a side elevation view of another articulation band of the modified shaft assembly of FIG. 40A;

FIG. 43A depicts the articulation bands of FIG. 40A with "weak spots" of the articulation bands offset from one another;

FIG. 43B depicts the articulation bands of FIG. 40A with "weak spots" of the articulation bands aligned with one another;

FIG. 44 depicts a detailed cross-sectional top plan view of a modified version of the shaft assembly of FIG. 2 having yet another exemplary structural feature;

FIG. 45 depicts a detailed cross-sectional top plan view of a modified version of the shaft assembly of FIG. 2 having yet another exemplary structural feature;

Figure 1:
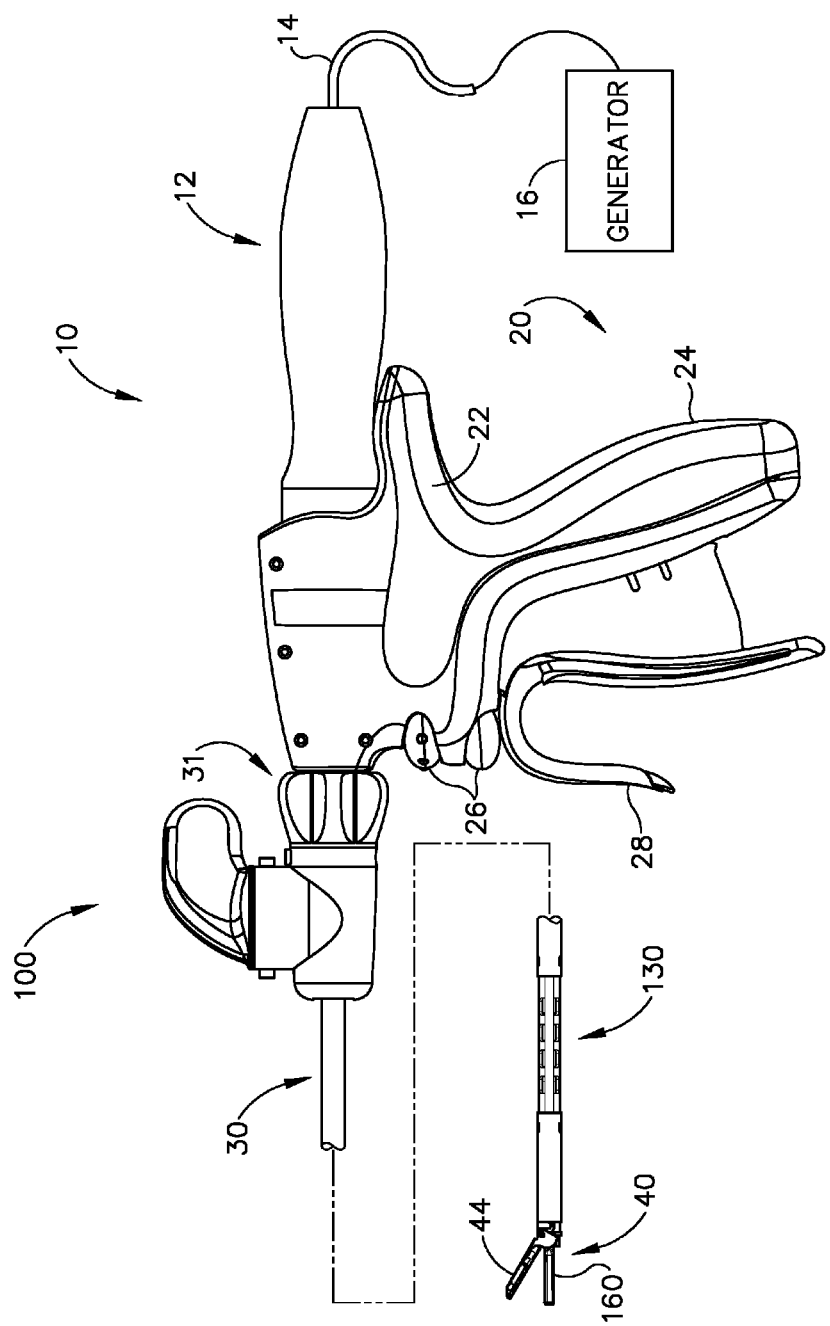
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (10) of the present example comprises a handle assembly (20), a shaft assembly (30), and an end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. End effector (40) includes an ultrasonic blade (160) and a pivoting clamp arm (44). Clamp arm (44) is coupled with trigger (28) such that clamp arm (44) is pivotable toward ultrasonic blade (160) in response to pivoting of trigger (28) toward pistol grip (24); and such that clamp arm (44) is pivotable away from ultrasonic blade (160) in response to pivoting of trigger (28) away from pistol grip (24). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (12) extends proximally from body (22) of handle assembly (20). Transducer assembly (12) is coupled with a generator (16) via a cable (14), such that transducer assembly (12) receives electrical power from generator (16). Piezoelectric elements in transducer assembly (12) convert that electrical power into ultrasonic vibrations. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

A. Exemplary End Effector and Acoustic Drivetrain

Figure 2:
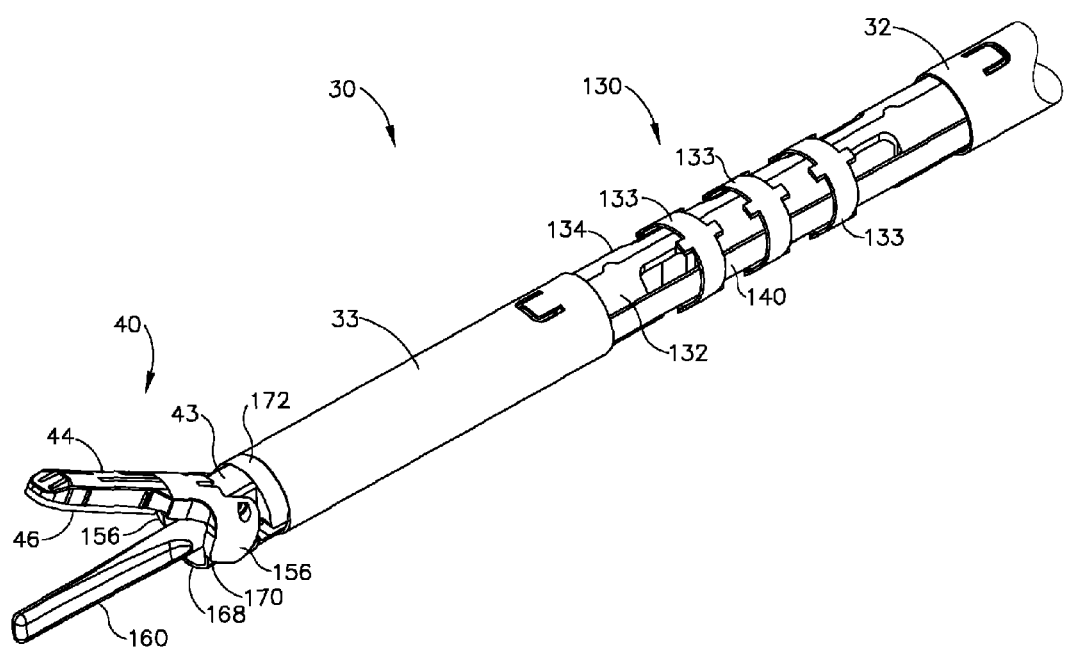
FIG. 2 depicts a perspective view of an articulation section of a shaft assembly and an end effector of the surgical instrument of FIG. 1.
Figure 3:
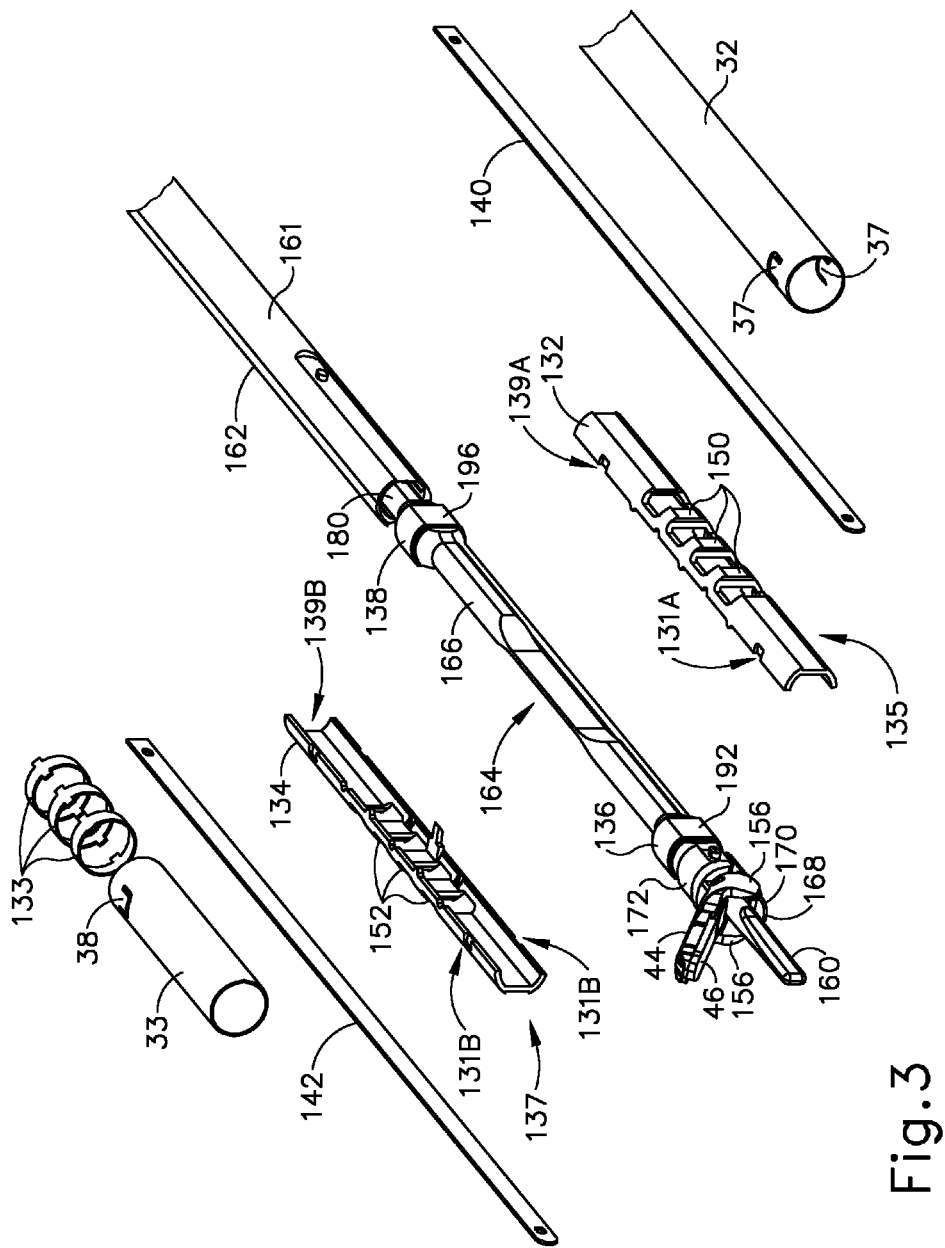
FIG. 3 depicts an exploded perspective view of an articulation section of the shaft assembly of FIG. 2.
Figure 4:
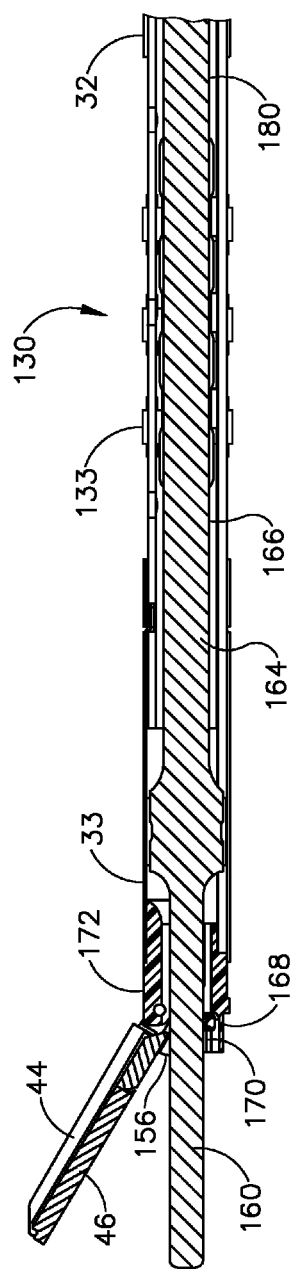
FIG. 4 depicts a cross-sectional side view of the shaft assembly and end effector of FIG. 2.

As best seen in FIGS. 2-4, end effector (40) of the present example comprises clamp arm (44) and ultrasonic blade (160). Clamp arm (44) includes a clamp pad (46) that is secured to the underside of clamp arm (44), facing blade (160). Clamp pad (46) may comprise polytetrafluoroethylene (PTFE) and/or any other suitable material(s). Clamp arm (44) is pivotally secured to a distally projecting tongue (43) of an upper distal shaft element (172), which is fixedly secured within a distal portion of a distal outer sheath (33). Clamp arm (44) is operable to selectively pivot toward and away from blade (160) to selectively clamp tissue between clamp arm (44) and blade (160). A pair of arms (156) extend transversely from clamp arm (44) and are pivotally secured to a lower distal shaft element (170), which is slidably disposed within the distal portion of distal outer sheath (33).

Figure 7:
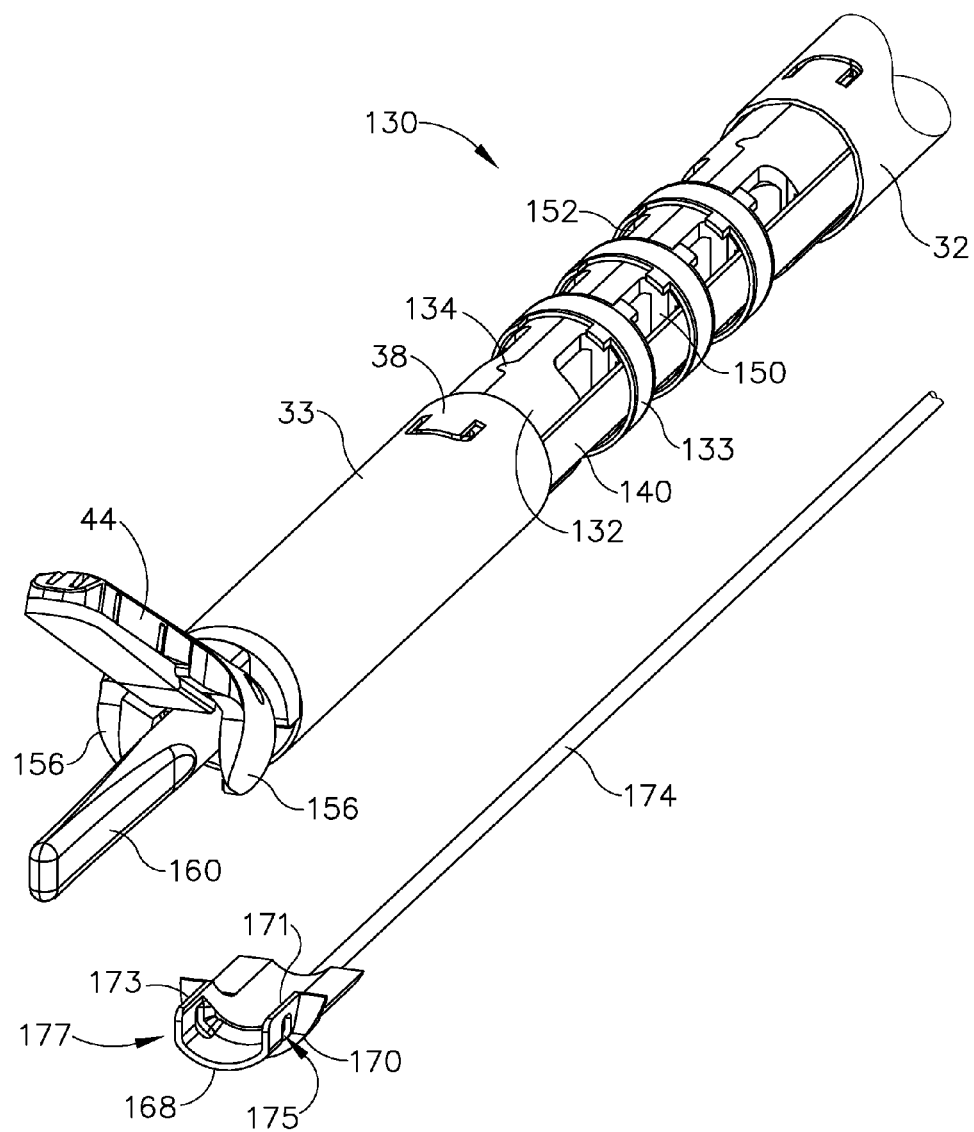
FIG. 7 depicts a partially exploded perspective view of the shaft assembly and end effector of FIG. 2.
Figure 8:
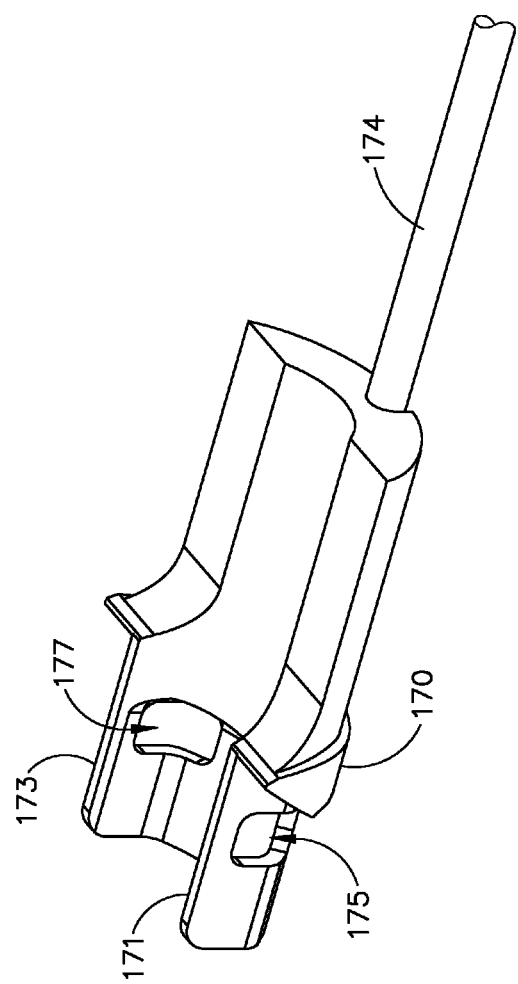
FIG. 8 depicts a perspective view of a distal collar and a drive cable of the shaft assembly of FIG. 2.

As best seen in FIGS. 7-8, a cable (174) is secured to lower distal shaft element (170). Cable (174) is operable to translate longitudinally relative to an articulation section (130) of shaft assembly (30) to selectively pivot clamp arm (44) toward and away from blade (160). In particular, cable (174) is coupled with trigger (28) such that cable (174) translates proximally in response to pivoting of trigger (28) toward pistol grip (24), and such that clamp arm (44) thereby pivots toward blade (160) in response to pivoting of trigger (28) toward pistol grip (24). In addition, cable (174) translates distally in response to pivoting of trigger (28) away from pistol grip (24), such that clamp arm (44) pivots away from blade (160) in response to pivoting of trigger (28) away from pistol grip (24). Clamp arm (44) may be biased toward the open position, such that (at least in some instances) the operator may effectively open clamp arm (44) by releasing a grip on trigger (28).

Figure 10A:
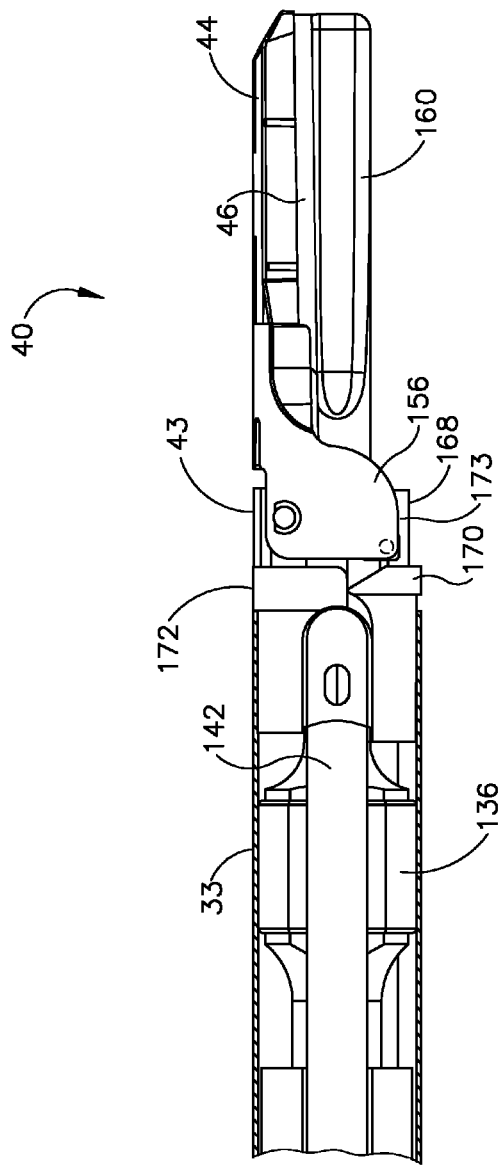
FIG. 10A depicts a side elevational view of the end effector and the distal portion of the shaft assembly of FIG. 2, with a clamp arm of the end effector in a closed position, and with an outer sheath shown in cross-section to reveal components within the outer sheath.
Figure 10B:
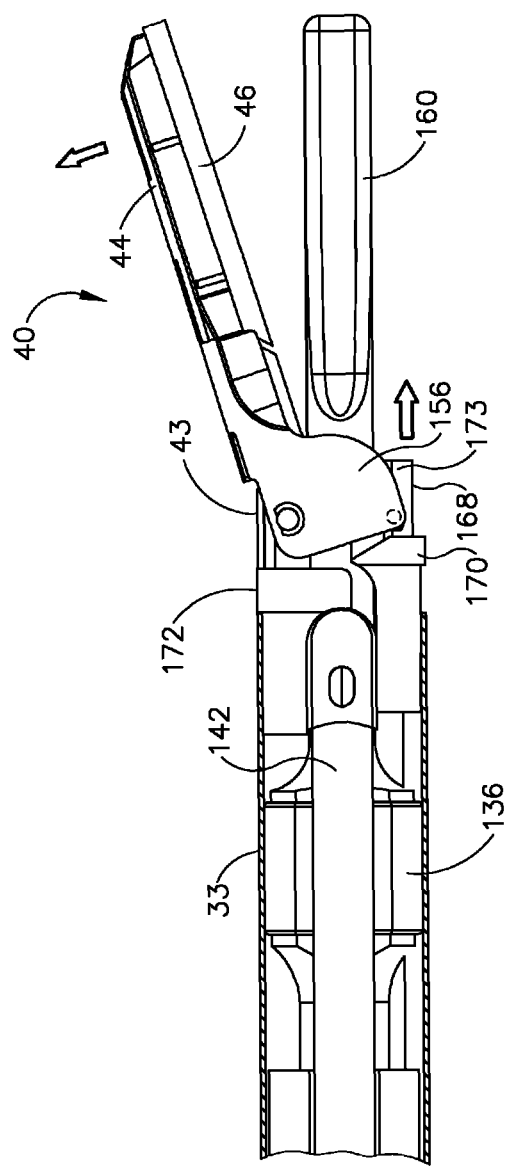
FIG. 10B depicts a side elevational view of the shaft assembly and end effector of FIG. 10A, with the clamp arm moved to a partially open position.
Figure 10C:
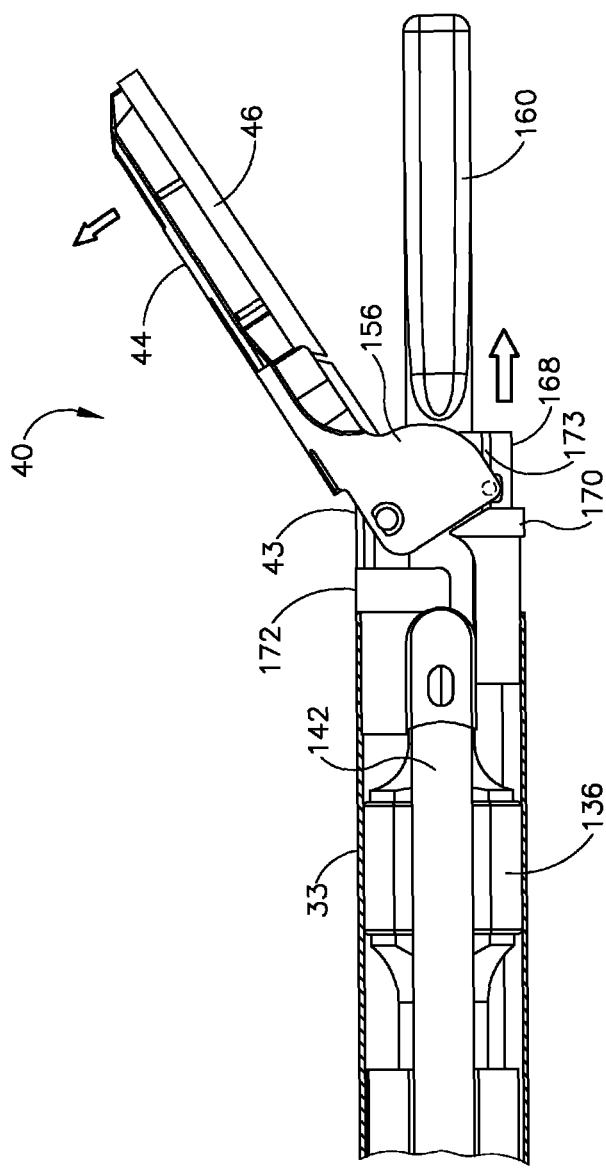
FIG. 10C depicts a side elevational view of the shaft assembly and end effector of FIG. 10A, with the clamp arm moved to a fully open position.

As shown in FIGS. 7-8, cable (174) is secured to a proximal end of lower distal shaft element (170). Lower distal shaft element (170) comprises a pair of distal flanges (171, 173) extending from a semi-circular base (168). Flanges (171, 173) each comprise a respective opening (175, 177). Clamp arm (44) is rotatably coupled to lower distal shaft element (170) via a pair of inwardly extending integral pins (41, 45). Pins (41, 45) extend inwardly from arms (156) of clamp arm (44) and are rotatably disposed within respective openings (175, 177) of lower distal shaft element (170). As shown in FIGS. 10A-10C, longitudinal translation of cable (174) causes longitudinal translation of lower distal shaft element (170) between a proximal position (FIG. 10A) and a distal position (FIG. 10C). Longitudinal translation of lower distal shaft element (170) causes rotation of clamp arm (44) between a closed position (FIG. 10A) and an open position (FIG. 10C).

Blade (160) of the present example is operable to vibrate at ultrasonic frequencies in order to effectively cut through and seal tissue, particularly when the tissue is being compressed between clamp pad (46) and blade (160). Blade (160) is positioned at the distal end of an acoustic drivetrain. This acoustic drivetrain includes transducer assembly (12) and an acoustic waveguide (180). Acoustic waveguide (180) comprises a flexible portion (166). Transducer assembly (12) includes a set of piezoelectric discs (not shown) located proximal to a horn (not shown) of waveguide (180). The piezoelectric discs are operable to convert electrical power into ultrasonic vibrations, which are then transmitted along waveguide (180), including flexible portion (166) of waveguide (180) to blade (160) in accordance with known configurations and techniques. By way of example only, this portion of the acoustic drivetrain may be configured in accordance with various teachings of various references that are cited herein.

As best seen in FIG. 3, flexible portion (166) of waveguide (180) includes a distal flange (136), a proximal flange (138), and a narrowed section (164) located between flanges (136, 138). In the present example, flanges (136, 138) are located at positions corresponding to nodes associated with resonant ultrasonic vibrations communicated through flexible portion (166) of waveguide (180). Narrowed section (164) is configured to allow flexible portion (166) of waveguide (180) to flex without significantly affecting the ability of flexible portion (166) of waveguide (180) to transmit ultrasonic vibrations. By way of example only, narrowed section (164) may be configured in accordance with one or more teachings of U.S. Pub. No. 2014/0005701, now U.S. Pat. No. 9,393,037 and/or U.S. Pub. No. 2014/0114334, now U.S. Pat. No. 9,095,367, the disclosures of which are incorporated by reference herein. It should be understood that waveguide (180) may be configured to amplify mechanical vibrations transmitted through waveguide (180). Furthermore, waveguide (180) may include features operable to control the gain of the longitudinal vibrations along waveguide (180) and/or features to tune waveguide (180) to the resonant frequency of the system. Various suitable ways in which waveguide (180) may be mechanically and acoustically coupled with transducer assembly (12) will be apparent to those of ordinary skill in the art in view of the teachings herein.

In the present example, the distal end of blade (160) is located at a position corresponding to an anti-node associated with resonant ultrasonic vibrations communicated through flexible portion (166) of waveguide (180), in order to tune the acoustic assembly to a preferred resonant frequency $f_o$ when the acoustic assembly is not loaded by tissue. When transducer assembly (12) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguide (180) to reach blade (160), thereby providing oscillation of blade (160) at the resonant ultrasonic frequency. Thus, when tissue is secured between blade (160) and clamp pad (46), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (44) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

B. Exemplary Shaft Assembly and Articulation Section

Shaft assembly (30) of the present example extends distally from handle assembly (20). As shown in FIGS. 2-7, shaft assembly (30) includes distal outer sheath (33) and a proximal outer sheath (32) that enclose clamp arm (44) drive features and the above-described acoustic transmission features. Shaft assembly (30) further includes an articulation section (130), which is located at a distal portion of shaft assembly (30), with end effector (40) being located distal to articulation section (130). As shown in FIG. 1, a knob (31) is secured to a proximal portion of proximal outer sheath (32). Knob (31) is rotatable relative to body (22), such that shaft assembly (30) is rotatable about the longitudinal axis defined by outer sheath (32), relative to handle assembly (20). Such rotation may provide rotation of end effector (40), articulation section (130), and shaft assembly (30) unitarily. Of course, rotatable features may simply be omitted if desired.

Articulation section (130) is operable to selectively position end effector (40) at various lateral deflection angles relative to a longitudinal axis defined by outer sheath (32). Articulation section (130) may take a variety of forms. By way of example only, articulation section (130) may be configured in accordance with one or more teachings of U.S. Pub. No. 2012/0078247, now U.S. Pat. No. 9,402,682, the disclosure of which is incorporated by reference herein. As another merely illustrative example, articulation section (130) may be configured in accordance with one or more teachings of U.S. Pub. No. 2014/0005701, now U.S. Pat. No. 9,393,037 and/or U.S. Pub. No. 2014/0114334, now U.S. Pat. No. 9,095,367, the disclosures of which are incorporated by reference herein. Various other suitable forms that articulation section (130) may take will be apparent to those of ordinary skill in the art in view of the teachings herein.

As best seen in FIGS. 2-6B articulation section (130) of this example comprises a set of three retention collars (133) and a pair of ribbed body portions (132, 134), with a pair of articulation bands (140, 142) extending along respective channels (135, 137) defined between interior surfaces of retention collars (133) and exterior surfaces of ribbed body portions (132, 134). Ribbed body portions (132, 134) are longitudinally positioned between flanges (136, 138) of flexible portion (166) of waveguide (180). In some versions, ribbed body portions (132, 134) snap together about flexible portion (166) of waveguide (180). Ribbed body portions (132, 134) are configured to flex with flexible portion (166) of waveguide (180) when articulation section (130) bends to achieve an articulated state.

FIG. 3 shows ribbed body portions (132, 134) in greater detail. In the present example, ribbed body portions (132, 134) are formed of a flexible plastic material, though it should be understood that any other suitable material may be used. Ribbed body portion (132) comprises a set of three ribs (150) that are configured to promote lateral flexing of ribbed body portion (132). Of course, any other suitable number of ribs (150) may be provided. Ribbed body portion (132) also defines a channel (135) that is configured to receive articulation band (140) while allowing articulation band (140) to slide relative to ribbed body portion (132). Similarly, ribbed body portion (134) comprises a set of three ribs (152) that are configured to promote lateral flexing of ribbed body portion (134). Of course, any other suitable number of ribs (152) may be provided. Ribbed body portion (134) also defines a channel (137) that is configured to receive articulation band (142) while allowing articulation band (142) to slide relative to ribbed body portion (137).

Figure 5:
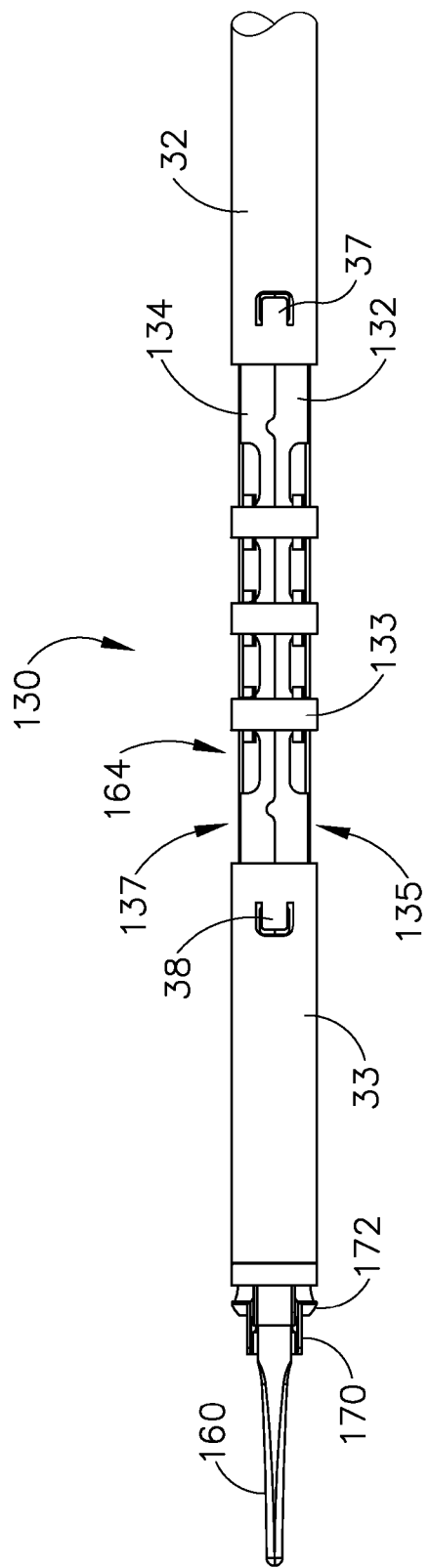
FIG. 5 depicts a top plan view of the shaft assembly and end effector of FIG. 2.

As best seen in FIG. 5, ribbed body portions (132, 134) are laterally interposed between articulation bands (140, 142) and flexible portion (166) of waveguide (180). Ribbed body portions (132, 134) mate with each other such that they together define an internal passage sized to accommodate flexible portion (166) of waveguide (180) without contacting waveguide (180). In addition, when ribbed body portions (132, 134) are coupled together, a pair of complementary distal notches (131A, 131B) formed in ribbed body portions (132, 134) align to receive a pair of inwardly projecting resilient tabs (38) of distal outer sheath (33). This engagement between tabs (38) and notches (131A, 131B) longitudinally secures ribbed body portions (132, 134) relative to distal outer sheath (33). Similarly, when ribbed body portions (132, 134) are coupled together, a pair of complementary proximal notches (139A, 139B) formed in ribbed body portions (132, 134) align to receive a pair of inwardly projecting resilient tabs (37) of proximal outer sheath (32). This engagement between tabs (37) and notches (139A, 139B) longitudinally secures ribbed body portions (132, 134) relative to proximal outer sheath (32). Of course, any other suitable kinds of features may be used to couple ribbed body portions (132, 134) with proximal outer sheath (32) and/or distal outer sheath (33).

Figure 6A:
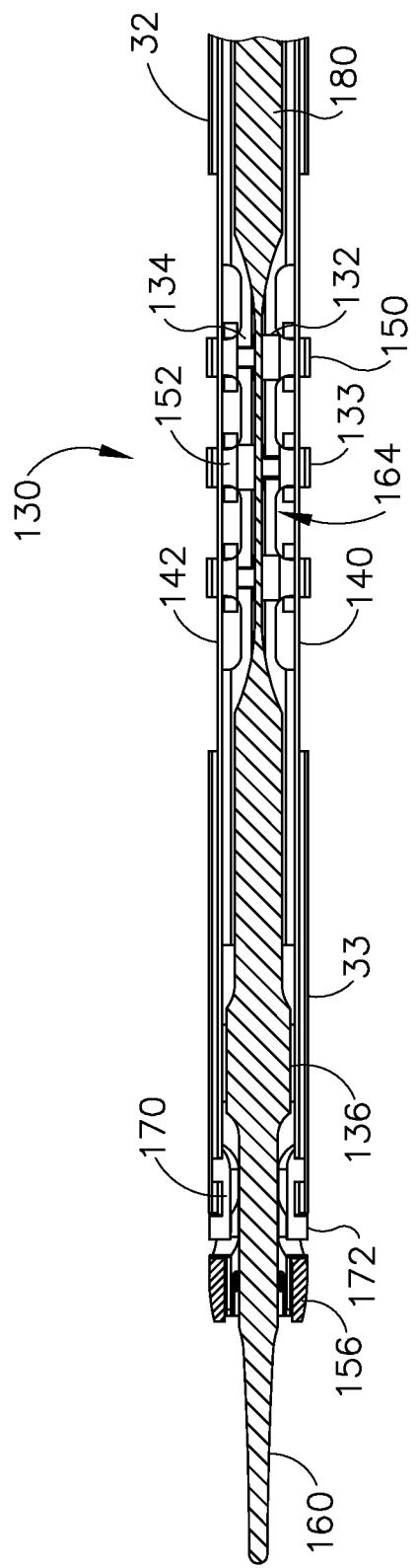
FIG. 6A depicts a cross-sectional top view of the shaft assembly and end effector of FIG. 2 in a straight configuration.
Figure 6B:
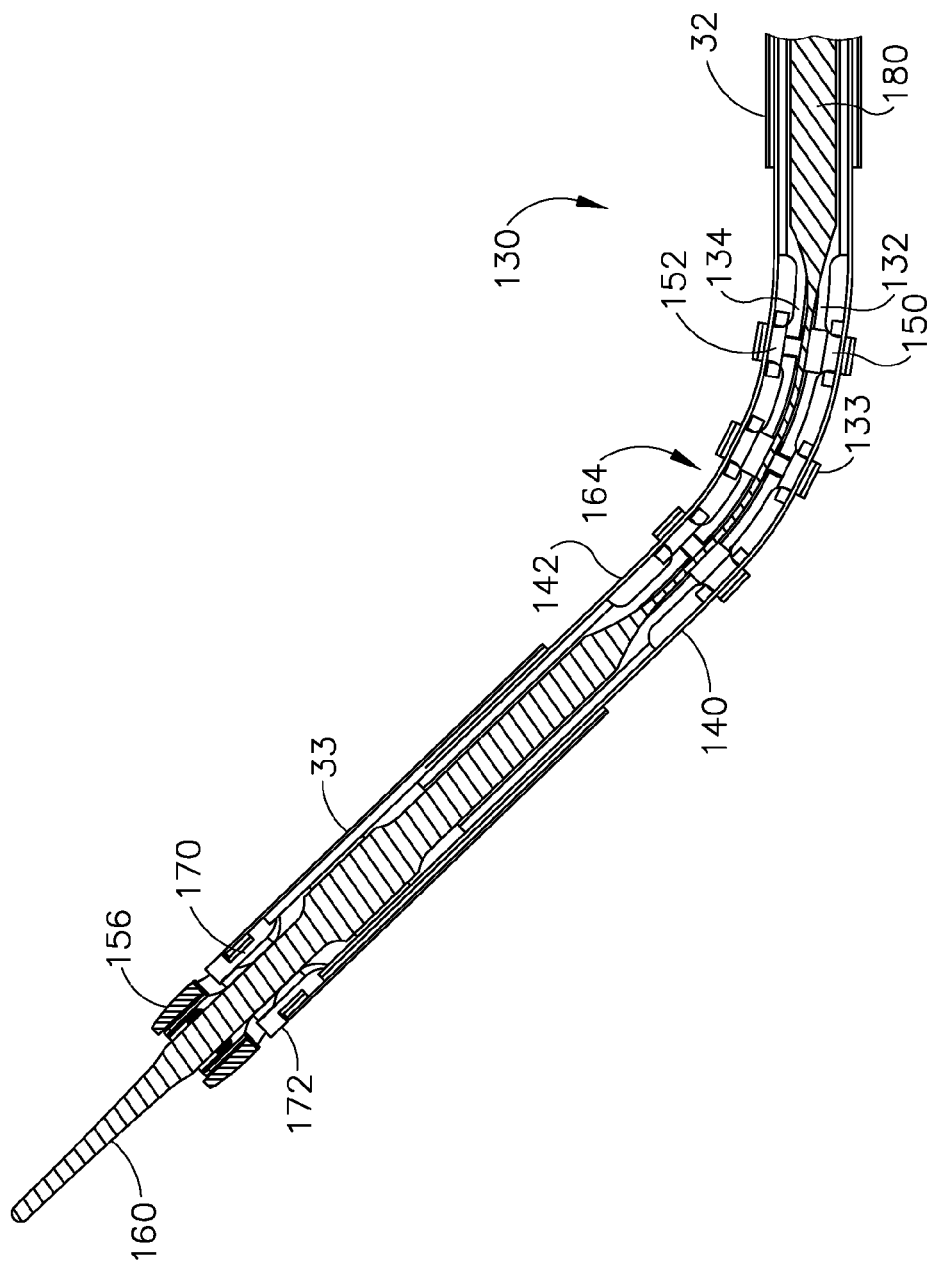
FIG. 6B depicts a cross-sectional top view of the shaft assembly and end effector of FIG. 2 in an articulated configuration.

The distal ends of articulation bands (140, 142) are unitarily secured to upper distal shaft element (172). When articulation bands (140, 142) translate longitudinally in an opposing fashion, this will cause articulation section (130) to bend, thereby laterally deflecting end effector (40) away from the longitudinal axis of shaft assembly (30) from a straight configuration as shown in FIG. 6A to an articulated configuration as shown in FIG. 6B. In particular, end effector (40) will be articulated toward the articulation band (140, 142) that is being pulled proximally. During such articulation, the other articulation band (140, 142) may be pulled distally by upper distal shaft element (172). Alternatively, the other articulation band (140, 142) may be driven distally by an articulation control. Ribbed body portions (132, 134) and narrowed section (164) are all sufficiently flexible to accommodate the above-described articulation of end effector (40). Furthermore, flexible acoustic waveguide (166) is configured to effectively communicate ultrasonic vibrations from waveguide (180) to blade (160) even when articulation section (130) is in an articulated state as shown in FIG. 6B.

As best seen in FIG. 3, each flange (136, 138) of waveguide (180) includes a respective pair of opposing flats (192, 196). Flats (192, 196) are oriented along vertical planes that are parallel to a vertical plane extending through narrowed section (164) of flexible portion (166). Flats (192, 196) are configured to provide clearance for articulation bands (140, 142). In particular, flats (196) of proximal flange (138) accommodate articulation bands (140, 142) between proximal flange (138) and the inner diameter of proximal outer sheath (32): while flats (192) of distal flange (136) accommodate articulation bands (140, 142) between distal flange (136) and the inner diameter of distal outer sheath (33). Of course, flats (192, 196) could be substituted with a variety of features, including but not limited to slots, channels, etc., with any suitable kind of profile (e.g., square, flat, round, etc.). In the present example, flats (192, 196) are formed in a milling process, though it should be understood that any other suitable process(es) may be used. Various suitable alternative configurations and methods of forming flats (192, 196) will be apparent to those of ordinary skill in the art in view of the teachings herein. It should also be understood that waveguide (180) may include flats formed in accordance with at least some of the teachings of U.S. Pub. No. 2013/0289592, entitled "Ultrasonic Device for Cutting and Coagulating," filed Apr. 23, 2013, the disclosure of which is incorporated by reference herein.

In the present example, outer rings (133) are located at longitudinal positions corresponding to ribs (150, 152), such that three rings (133) are provided for three ribs (150, 152). Articulation band (140) is laterally interposed within channel (135) between rings (133) and ribbed body portion (132); while articulation band (142) is laterally interposed within channel (137) between rings (133) and ribbed body portion (134). Rings (133) are configured to keep articulation bands (140, 142) in a parallel relationship, particularly when articulation section (130) is in a bent configuration (e.g., similar to the configuration shown in FIG. 6B). In other words, when articulation band (140) is on the inner diameter of a curved configuration presented by a bent articulation section (130), rings (133) may retain articulation band (140) such that articulation band (140) follows a curved path that complements the curved path followed by articulation band (142). It should be understood that channels (135, 137) are sized to accommodate respective articulation bands (140, 142) in such a way that articulation bands (140, 142) may still freely slide through articulation section (130), even with rings (133) being secured to ribbed body portions (150, 152). It should also be understood that rings (133) may be secured to ribbed body portions (132, 134) in various ways, including but not limited to interference fitting, adhesives, welding, etc.

When articulation bands (140, 142) are translated longitudinally in an opposing fashion, a moment is created and applied to a distal end of distal outer sheath (33) via upper distal shaft element (172). This causes articulation section (130) and narrowed section (164) of flexible portion (166) of waveguide (180) to articulate, without transferring axial forces in articulation bands (140, 142) to waveguide (180). It should be understood that one articulation band (140, 142) may be actively driven distally while the other articulation band (140, 142) is passively permitted to retract proximally. As another merely illustrative example, one articulation band (140, 142) may be actively driven proximally while the other articulation band (140, 142) is passively permitted to advance distally. As yet another merely illustrative example, one articulation band (140, 142) may be actively driven distally while the other articulation band (140, 142) is actively driven proximally. Various suitable ways in which articulation bands (140, 142) may be driven will be apparent to those of ordinary skill in the art in view of the teachings herein.

As best seen in FIG. 9, an articulation control assembly (100) is secured to a proximal portion of outer sheath (32). Articulation control assembly (100) comprises a housing (110) and a rotatable knob (120). Housing (110) comprises a pair of perpendicularly intersecting cylindrical portions (112, 114). Knob (120) is rotatably disposed within a first hollow cylindrical portion (112) of housing (110) such that knob (120) is operable to rotate within cylindrical portion (112) of housing (110). Shaft assembly (30) is slidably and rotatably disposed within a second cylindrical portion (114). Shaft assembly (30) comprises a pair of translatable members (161, 162), both of which extend slidably and longitudinally through the proximal portion of outer sheath (32). Translatable members (161, 162) are longitudinally translatable within second cylindrical portion (114) between a distal position and a proximal position. Translatable members (161, 162) are mechanically coupled with respective articulation bands (140, 142) such that longitudinal translation of translatable member (161) causes longitudinal translation of articulation band (140), and such that longitudinal translation of translatable member (162) causes longitudinal translation of articulation band (142).

Knob (120) comprises a pair of pins (122, 124) extending downwardly from a bottom surface of knob (120). Pins (122, 124) extend into second cylindrical portion (114) of housing (110) and are rotatably and slidably disposed within a respective pair of channels (163, 164) formed in top surfaces of translatable members (161, 162). Channels (163, 164) are positioned on opposite sides of an axis of rotation of knob (120), such that rotation of knob (120) about that axis causes opposing longitudinal translation of translatable members (161, 162). For instance, rotation of knob (120) in a first direction causes distal longitudinal translation of translatable member (161) and articulation band (140), and proximal longitudinal translation of translatable member (162) and articulation band (142); and rotation of knob (120) in a second direction causes proximal longitudinal translation of translatable member (161) and articulation band (140), and distal longitudinal translation of translatable member (162) and articulation band (142). Thus, it should be understood that rotation of rotation knob (120) causes articulation of articulation section (130).

Housing (110) of articulation control assembly (100) comprises a pair of set screws (111, 113) extending inwardly from an interior surface of first cylindrical portion (112). With knob (120) rotatably disposed within first cylindrical portion (112) of housing (110), set screws (111, 113) are slidably disposed within a pair of arcuate channels (121, 123) formed in knob (120). Thus, it should be understood that rotation of knob (120) will be limited by movement of set screws (111, 113) within channels (121, 123). Set screws (111, 113) also retain knob (120) in housing (110), preventing knob (120) from traveling vertically within first cylindrical portion (112) of housing (110).

An interior surface of first cylindrical portion (112) of housing (110) comprises a first angular array of teeth (116) and a second angular array of teeth (118) formed in an interior surface of first cylindrical portion (112). Rotation knob (120) comprises a pair of outwardly extending engagement members (126, 128) that are configured to engage teeth (116, 118) of first cylindrical portion (112) in a detent relationship to thereby selectively lock knob (120) in a particular rotational position. The engagement of engagement members (126, 128) with teeth (116, 118) may be overcome by a user applying sufficient rotational force to knob (120); but absent such force, the engagement will suffice to maintain the straight or articulated configuration of articulation section (130). It should therefore be understood that the ability to selectively lock knob (120) in a particular rotational position lock will enable an operator to selectively lock articulation section (130) in a particular deflected position relative to the longitudinal axis defined by outer sheath (32).

In some versions of instrument (10), articulation section (130) of shaft assembly (30) is operable to achieve articulation angles up to between approximately 15° and approximately 30°, both relative to the longitudinal axis of shaft assembly (30) when shaft assembly (30) is in a straight (non-articulated) configuration. Alternatively, articulation section (130) may be operable to achieve any other suitable articulation angles.

In some versions of instrument (10), narrowed section (164) of waveguide (180) has a thickness between approximately 0.01 inches and approximately 0.02 inches. Alternatively, narrowed section (164) may have any other suitable thickness. Also in some versions, narrowed section (164) has a length of between approximately 0.4 inches and approximately 0.65 inches. Alternatively, narrowed section (164) may have any other suitable length. It should also be understood that the transition regions of waveguide (180) leading into and out of narrowed section (164) may be quarter rounded, tapered, or have any other suitable configuration.

In some versions of instrument (10), flanges (136, 138) each have a length between approximately 0.1 inches and approximately 0.2 inches. Alternatively, flanges (136, 138) may have any other suitable length. It should also be understood that the length of flange (136) may differ from the length of flange (138). Also in some versions, flanges (136, 138) each have a diameter between approximately 0.175 inches and approximately 0.2 inches. Alternatively, flanges (136, 138) may have any other suitable outer diameter. It should also be understood that the outer diameter of flange (136) may differ from the outer diameter of flange (138).

While the foregoing exemplary dimensions are provided in the context of instrument (10) as described above, it should be understood that the same dimensions may be used in any of the other examples described herein. It should also be understood that the foregoing exemplary dimensions are merely optional. Any other suitable dimensions may be used.

II. Exemplary Alternative Shaft Assemblies

In some versions of instrument (10) it may be desirable to provide features that are configured to selectively provide rigidity to articulation section (130). For instance, because of various factors such as manufacturing tolerances, design limitations, material limitations, and/or other factors, some versions of articulation section (130) may be susceptible to some "play" or other small movement of the articulation section despite being relatively fixed in a given position, such that articulation section (130) is not entirely rigid. It may be desirable to reduce or eliminate such play in articulation section (130), particularly when articulation section (130) is in a straight, non-articulated configuration. Features may thus be provided to selectively rigidize articulation section (130). Various examples of features that are configured to selectively provide rigidity to articulation section (130) and/or to limit or prevent inadvertent deflection of end effector (40) will be described in greater detail below. Other examples will be apparent to those of ordinary skill in the art according to the teachings herein. It should be understood that the examples of shaft assemblies and/or articulation sections described below may function substantially similar to shaft assembly (30) discussed above.

It should also be understood that articulation section (130) may still be at least somewhat rigid before being modified to include the features described below, such that the features described below actually just increase the rigidity of articulation section (130) rather than introducing rigidity to an otherwise non-rigid articulation section (130). For instance, an articulation section (130) in the absence of features as described below may be rigid enough to substantially maintain a straight or articulated configuration; yet may still provide "play" of about 1 mm or a fraction thereof such that the already existing rigidity of articulation section (130) may be increased. Thus, terms such as "provide rigidity" and "providing rigidity" shall be understood to include just increasing rigidity that is already present in some degree. The terms "provide rigidity" and "providing rigidity" should not be read as necessarily requiring articulation section (130) to completely lack rigidity before the rigidity is "provided."

A. Exemplary Collapsible and Expandable Rigidizing Member

FIGS. 11A and 11B show shaft assembly (30) of instrument (10) described above having a collapsible and expandable tube (200) added thereon. As will be described in more detail below, tube (200) may function to selectively provide rigidity to articulation section (130) and/or to prevent inadvertent deflection of end effector (40) relative to outer sheath (32). Tube (200) of the present example comprises a plurality of annular members (202) disposed about shaft assembly (30), including articulation section (130). As will be described in more detail below, annular members (202) are longitudinally translatable along a length of shaft assembly (30) relative to one another between an expanded configuration (FIG. 11A) and a collapsed configuration (FIG. 11B). Also as will be described in more detail below, when in the collapsed configuration, annular members (202) function to provide rigidity to articulation section (130) and/or to prevent inadvertent deflection of end effector (40) relative to outer sheath (32).

A distal-most ring-shaped member (202A) of tube (200) is secured to an exterior surface of distal outer sheath (33) of shaft assembly (30) distally of articulation section (130). The remainder of annular members (202) of outer sheath (200) are slidably disposed about shaft assembly (30), including articulation section (130), such that annular members (202) are translatable along a length shaft assembly (30) relative to one another. As shown in FIG. 11A, when in the expanded configuration, annular members (202), although positioned about articulation section (130), are spaced apart from one another. The space between consecutive annular members (202) allows articulation section (130) to flex to thereby deflect end effector (40) relative to the longitudinal axis of outer sheath (32). As shown in FIG. 11B, annular members (202) may be translated distally toward distal-most ring-shaped member (202A) into the collapsed configuration. In the collapsed configuration, annular members (202) abut one another to form a substantially continuous and rigid tubular member. Because annular members (202) abut one another in the collapsed configuration, annular members (202) function to provide rigidity to articulation section (130) and/or to prevent inadvertent deflection of end effector (40) relative to outer sheath (32). If a user then desires to deflect end effector (40), annular members (202) may be moved back to the expanded configuration to permit articulation section (130) to flex.

It should be understood that annular members (202) may be moved directly (e.g. by grasping one or more of annular members (202) directly, etc.) or by providing instrument (10) with additional actuation features. For example, handle assembly (20) of instrument (10) may be provided with a slidable actuator that is operable to cause independent or concurrent translation of annular members (202). It should further be understood that tube (200) may be provided with additional features that are configured to improve the structural integrity of tube (200) when in the collapsed configuration. For example, annular members (202) may be provided with mating projections and recesses or slots that are configured to allow annular members (202) to further engage one another when in the collapsed configuration. Additionally, or alternatively, annular members (202) may be provided with mating pins and pinholes that are configured to allow annular members (202) to further engage one another when in the collapsed configuration.

It should also be understood that annular members (202) may be tethered to each other by wires, cables, or other kinds of flexible members. In such versions, when the proximal-most annular member (202) is pulled proximally from the position shown in FIG. 11B to the position shown in FIG. 11A, such tethers may communicate the proximal motion from the proximal-most annular member (202) to the rest of the annular members (202), thereby pulling the rest of the proximal members from the positions shown in FIG. 11B to the positions shown in FIG. 11A. Such tethers may have a length selected to provide the spacing shown in FIG. 11A; while also having the flexibility to allow annular members (202) to reach the positions shown in FIG. 11B. Various suitable ways in which annular members (202) may be configured, actuated, and coupled with each other will be apparent to those of ordinary skill in the art in view of the teachings herein.

B. Exemplary Inflatable and Deflatable Rigidizing Member

Figure 12:
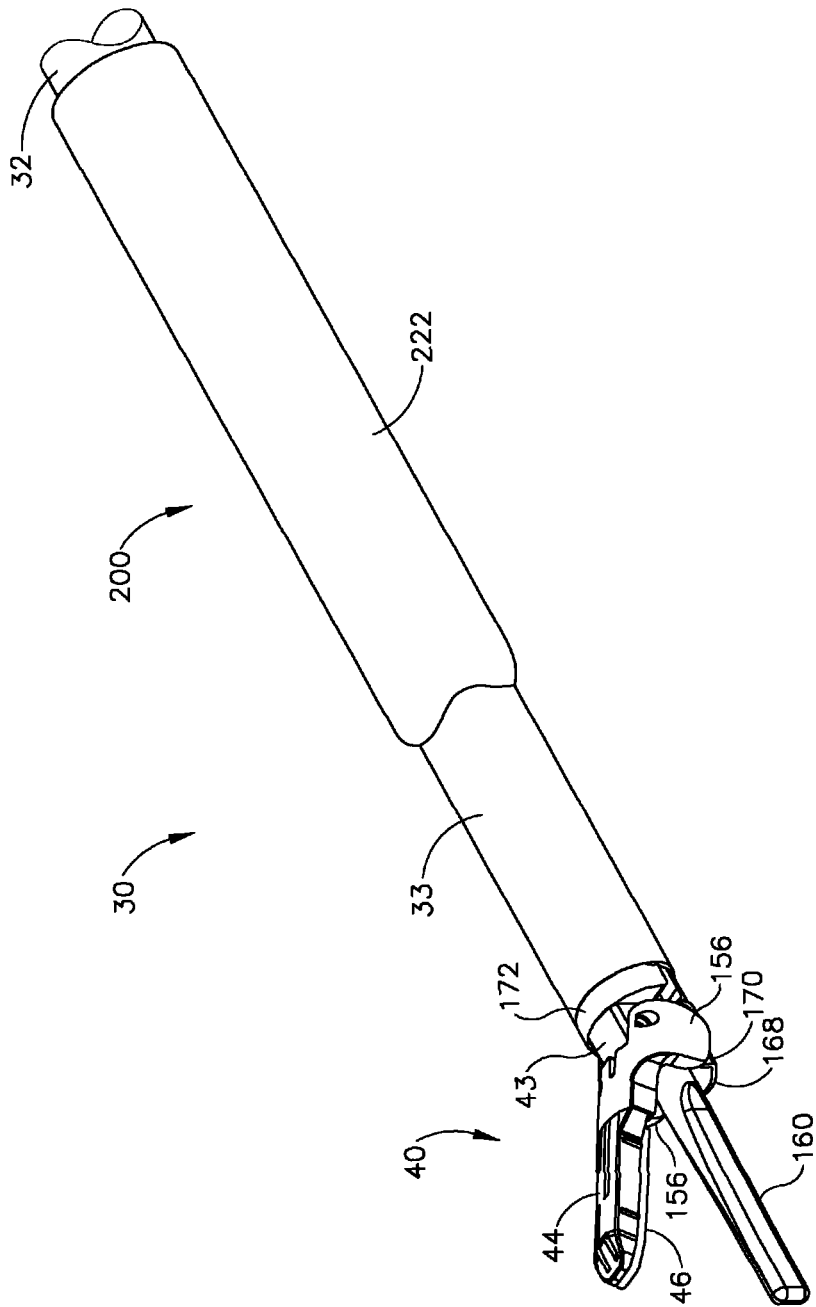
FIG. 12 depicts a perspective view of another modified version of the shaft assembly and end effector of FIG. 2 having another exemplary structural feature.
Figure 13C:
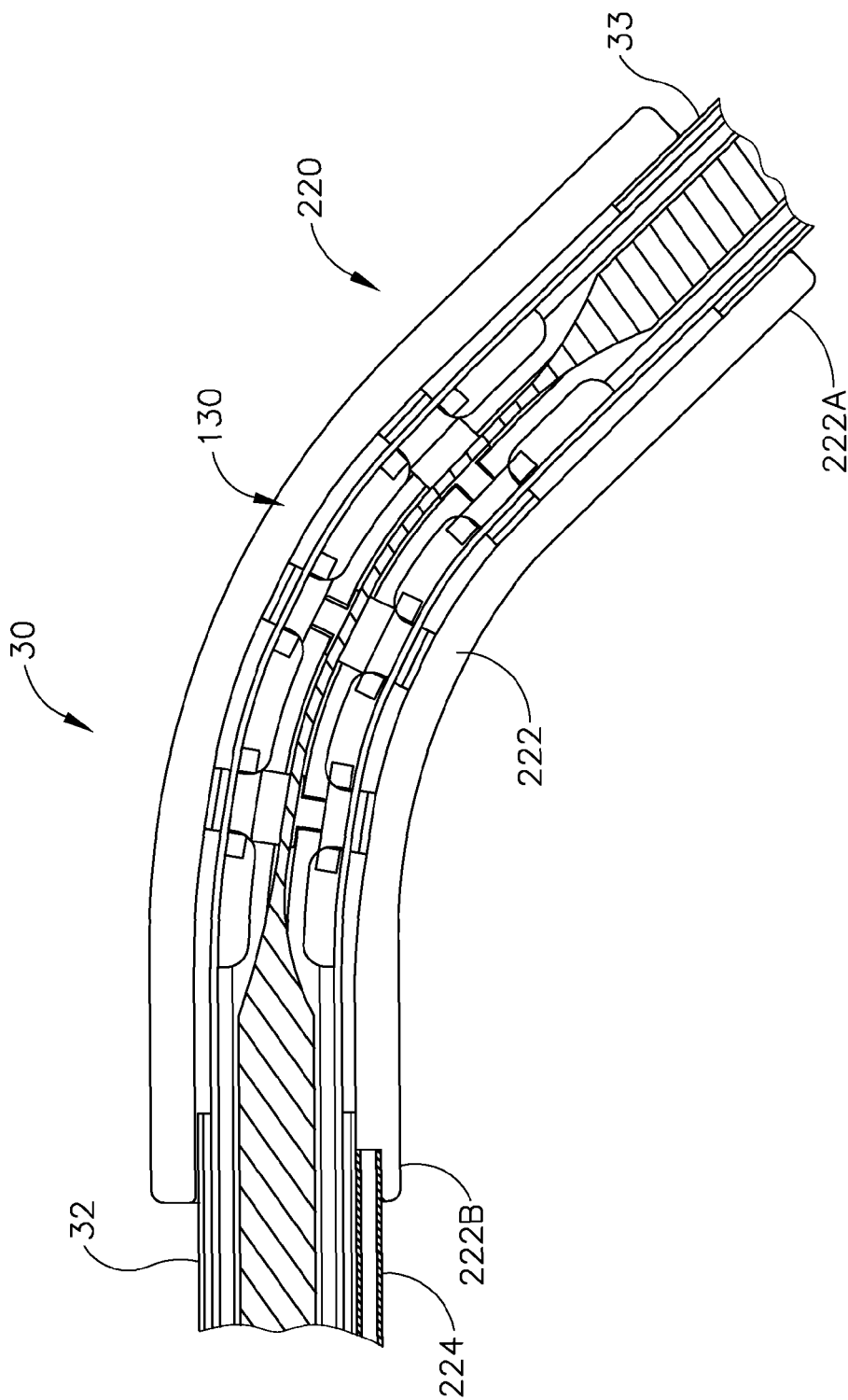
FIG. 13C depicts a cross-sectional top view of the modified shaft assembly and end effector of FIG. 12 in an articulated configuration with the structural feature of FIG. 12 deflated.

FIGS. 12-13C show shaft assembly (30) of instrument (10) described above having an inflatable and deflatable balloon (220) secured thereto. As will be described in more detail below, balloon (220) may function to selectively provide rigidity to articulation section (130) and/or to prevent inadvertent deflection of end effector (40) relative to outer sheath (32). Balloon (220) of the present example comprises a tubular body (222) disposed about shaft assembly (30), including articulation section (130). Fluid is provided to tubular body (222) via a tube (224) which extends along a length of shaft assembly (30) adjacent an exterior surface of outer sheath (30). As will be described in more detail below, tube (224) functions to provide fluid to or to remove fluid from tubular body (222) so as to transition balloon (220) between a deflated state (FIGS. 13A and 13C) and an inflated state (FIG. 13B). Also as will be described in more detail below, when in the inflated state, balloon (220) functions to provide rigidity to articulation section (130) and/or to prevent inadvertent deflection of end effector (40) relative to outer sheath (32) when balloon (220) is in an inflated state.

Tubular body (222) is disposed about shaft assembly (30), including articulation section (130). In the present example, tubular body (222) is formed of a flexible yet non-extensible material. Various suitable materials that may be used to form tubular body (222) will be apparent to those of ordinary skill in the art in view of the teachings herein. A distal end (222A) of tubular body (222) is secured to an exterior surface of distal outer sheath (33) of shaft assembly (30) distally of articulation section (130). A proximal end (222B) of tubular body (222) is secured to an exterior surface of outer sheath (32) of shaft assembly (30) proximally of articulation section (130). Thus, as shown in FIG. 13A, tubular body (222) completely encompasses articulation section (130). As shown in FIGS. 13A and 13C, when in the deflated state, tubular body (222), although positioned about articulation section (130), remains flexible enough to allow articulation section (130) to flex to thereby deflect end effector (40) relative to outer sheath (32). As shown in FIG. 13B, when in the inflated state, tubular body (222) becomes more rigid and functions to provide rigidity to articulation section (130) and/or to prevent inadvertent deflection of end effector (40) relative to outer sheath (32). If a user then desires to deflect end effector (40), tubular body (222) may be deflated to permit articulation section (130) to flex.

In the present example, the fluid communicated to tubular body (222) comprises saline, though it should be understood that any other suitable fluid may be used. There are various ways in such fluid (e.g., saline, etc.) may be provided to tubular body (222). By way of example only, a fluid syringe (not shown) may be coupled with a proximal end of tube (224) to thereby provide fluid to and to remove fluid from tubular body (222). It should also be understood that, when fluid is communicated to tubular body (222), the non-extensibility of tubular body may enable tubular body (222) to be inflated to pressures that make tubular body (222) substantially rigid, thereby effectively rigidizing articulation section (130). Various suitable fluid pressures and volumes that may be used for balloon (220) will be apparent to those of ordinary skill in the art in view of the teachings herein.

C. Exemplary Accordion-Like Rigidizing Member

FIGS. 14-18B show shaft assembly (30) of instrument (10) described above having an accordion-like rigidizing member (240) incorporated therein. As will be described in more detail below, rigidizing member (240) may function to selectively provide rigidity to articulation section (130) and/or to prevent inadvertent deflection of end effector (40) relative to outer sheath (32). As best seen in FIGS. 15A and 15B, rigidizing member (240) of the present example comprises a plurality of bellows (242) linked to one another along a length of rigidizing member (240). As will be described in more detail below, rigidizing member (240) is longitudinally translatable along a length of shaft assembly (30) so as to transition bellows (242) between a contracted configuration (FIG. 15A) and an expanded configuration (FIG. 15B). Also as will be described in more detail below, when in the contracted configuration, bellows (242) of rigidizing member (240) function to provide rigidity to articulation section (130) and/or to prevent inadvertent deflection of end effector (40) relative to outer sheath (32). By way of example only, rigidizing member (240) may be formed by a series of linkages that pivotably define bellows (242). Use of the term "bellows" should therefore be understood to not necessarily require a vessel that defines a variable capacity. Various suitable ways in which rigidizing member (240) may be configured will be apparent to those of ordinary skill in the art in view of the teachings herein.

Figure 14:
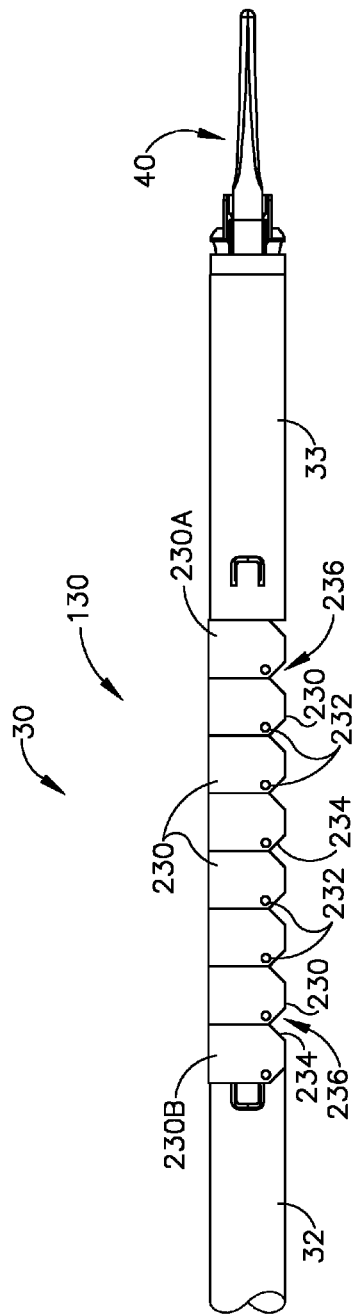
FIG. 14 depicts a top plan view of another modified version of the shaft assembly and end effector of FIG. 2 having a plurality of couplers linked to one another.
Figure 15A:
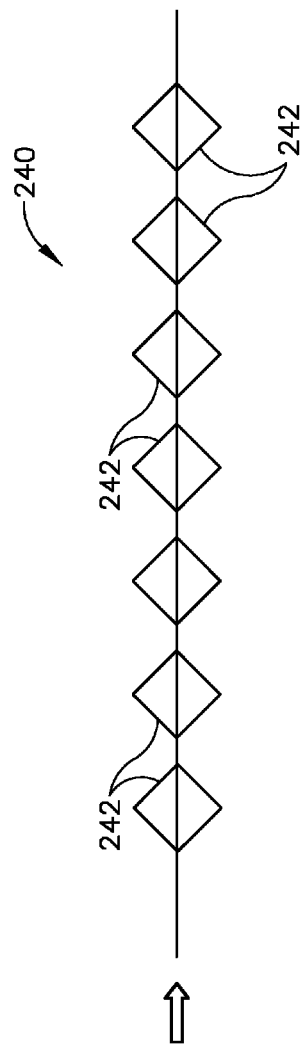
FIG. 15A depicts a top plan view of yet another exemplary structural feature that may be incorporated into the shaft assembly of FIG. 14, in a contracted configuration.

As shown in FIG. 14, shaft assembly (30) of the present example comprises a plurality of couplers (230) pivotably linked to one another via a plurality of pins (232). Couplers (230) are disposed about shaft assembly (30), including articulation section (130). A distal-most coupler (230A) of couplers (230) is secured to an exterior surface of distal outer sheath (33) of shaft assembly (30) distally of articulation section (130). A proximal-most coupler (230B) of couplers (230) is secured to an exterior surface of outer sheath (32) of shaft assembly (30) proximally of articulation section (130). Thus, as shown in FIG. 14, couplers (230), when linked to one another, completely encompass articulation section (130). Each coupler (230) includes a pair of angled surfaces (234) which, when couplers (230) are linked to one another, forms a plurality of V-shaped pockets (236) in a side surface rigidizing member (240). Pockets (236) are configured to provide clearance between couplers (230) to allow couplers (230) to pivot relative to each other about pins (232) as articulation section (130) is articulated. Pockets (236) are also configured to receive bellows (242) as described in greater detail below. While pockets (236) are shown on only one side of couplers (230) in this example, it should be understood that pockets (236) may be provided on both sides of couplers (230) if desired. Such a configuration may permit or facilitate articulation of articulation sections in two opposite directions relative to the longitudinal axis of outer sheath (32).

As shown in FIG. 17A, with bellows (242) in the contracted configuration, bellows (242) of rigidizing member (240) are configured to extend through V-shaped pockets (236) and bear against angled surfaces (234) of couplers (230) to thereby provide rigidity to articulation section (130) and/or to prevent inadvertent deflection of end effector (40) relative to outer sheath (32). As shown in FIG. 17B, rigidizing member (240) is drawn proximally so as to transition bellows (242) to the expanded configuration. This transitioning of bellows (242) draws bellows (242) inwardly from V-shaped pockets (236) such that bellows (242) no longer bear against angled surfaces (234) of couplers (230) and such that articulation section (130) may flex to thereby deflect end effector (40) relative to outer sheath (32).

Figure 18A:
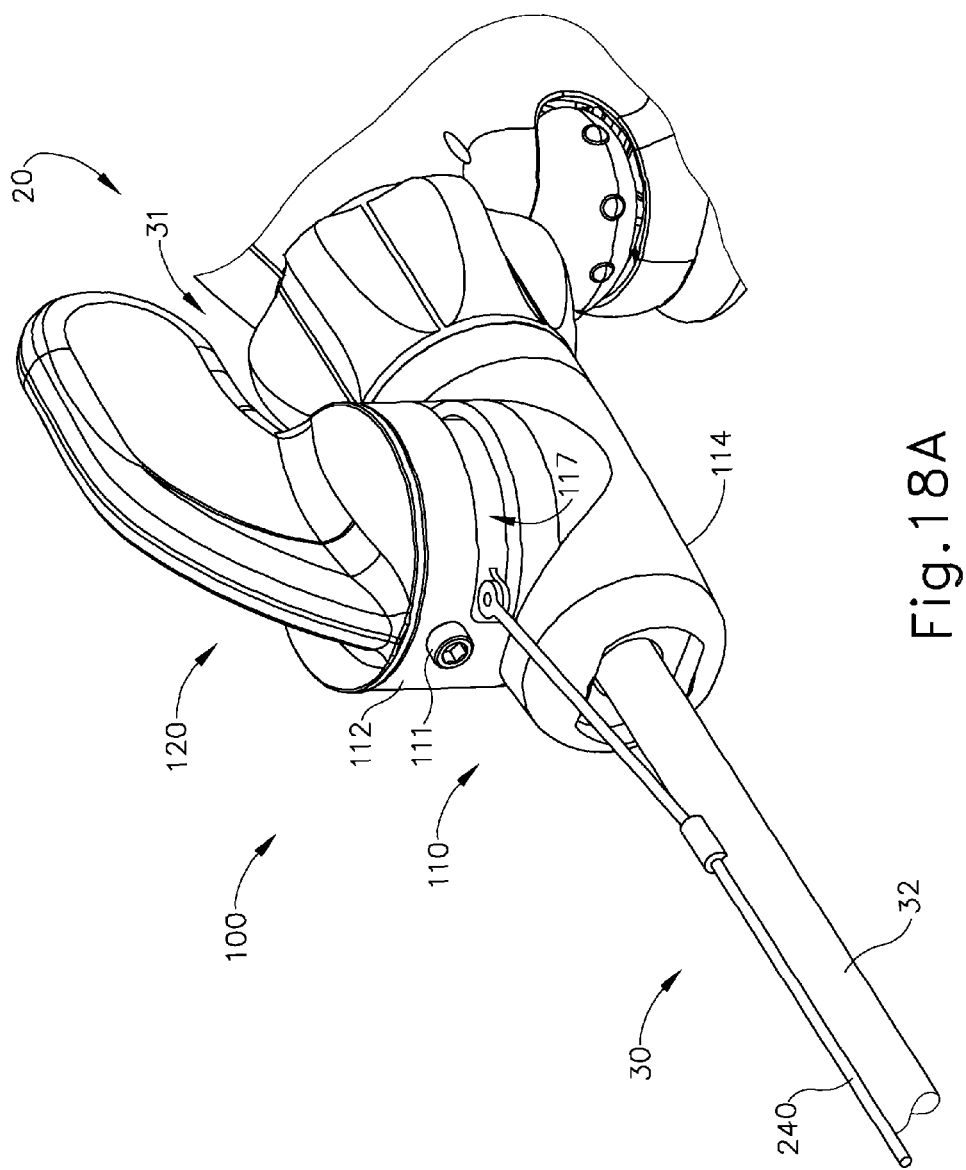
FIG. 18A depicts a perspective view of a modified version of the articulation control assembly of FIG. 9 in a first rotational position and coupled with a linkage of the structural feature of FIG. 15A.
Figure 18B:
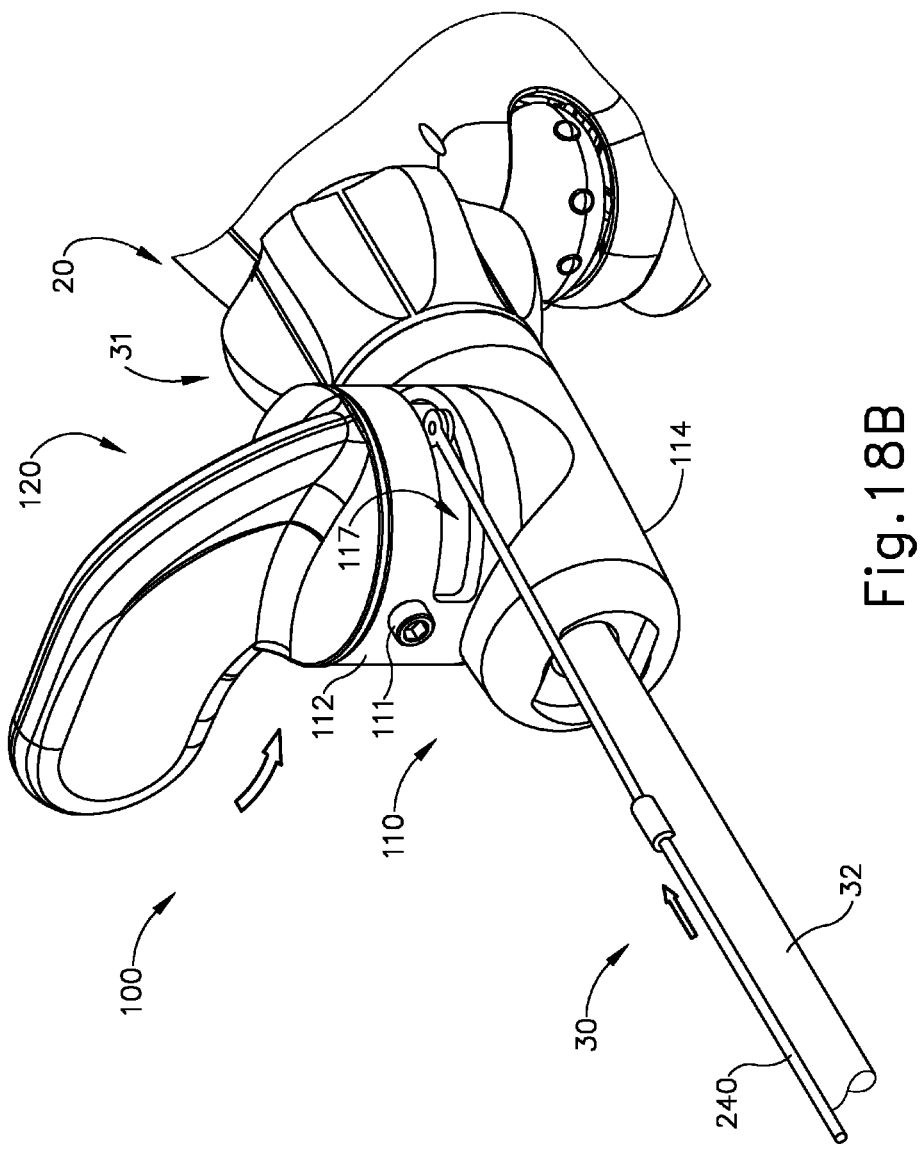
FIG. 18B depicts a perspective view of the modified articulation control assembly of FIG. 18A moved into a second rotational position so as to translate the linkage of FIG. 18A.
Figure 24:
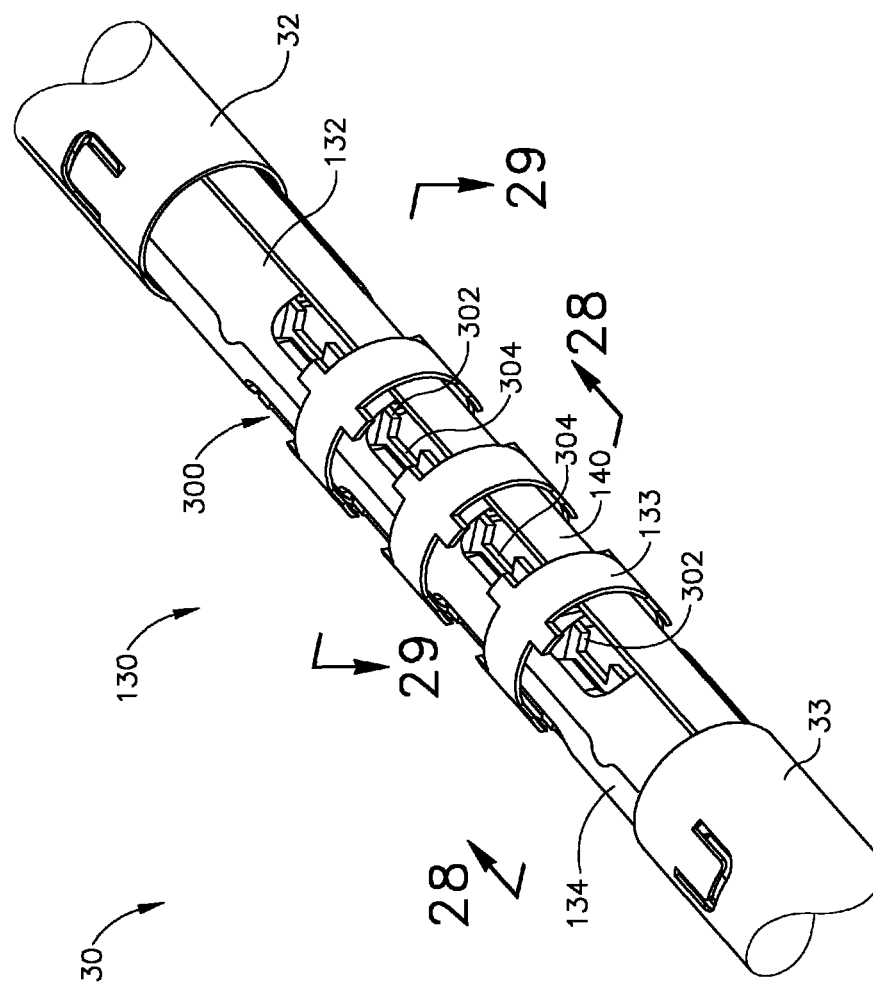
FIG. 24 depicts a perspective view of another modified version of the shaft assembly of FIG. 2 having yet another exemplary structural feature positioned therein.

In some versions of instrument (10), rigidizing member (240) may be coupled with rotation knob (120) such that rotation of rotation knob (120) causes concurrent articulation of articulation section (130) and translation of rigidizing member (240). For instance, as shown in FIGS. 18A and 18B, the proximal end of rigidizing member (240) may be coupled with rotation knob (120) via a slot (117) formed in a side of first hollow cylindrical portion (112) of housing (110). The distal end of rigidizing member (240) may be fixedly secured to distal outer sheath (33) or some other structure that is distal to articulation section (130). Thus, as rotation knob (120) is rotated in a first direction from the position shown in FIG. 18A to the position shown in FIG. 18B to cause articulation of articulation section (130), rigidizing member (240) is concurrently drawn proximally so as to transition bellows (242) from the configuration shown in FIG. 17A to the configuration shown in FIG. 17B. This causes bellows (242) to disengage angled surfaces (234), thus allowing articulation section (130) to flex to thereby deflect end effector (40) relative to outer sheath (32).

As rotation knob (120) is rotated in the opposite direction from the position shown in FIG. 18B to the position shown in FIG. 18A to return articulation section (130) to back toward the straight configuration, rigidizing member (240) is concurrently driven distally so as to transition bellows (242) back from the configuration shown in FIG. 17B to the configuration shown in FIG. 17A. This causes bellows (242) to re-engage angled surfaces (234), thus providing rigidity to articulation section (130) and/or preventing inadvertent deflection of end effector (40) relative to outer sheath (32). It should therefore be understood that articulation section (130) may be automatically rigidized upon reaching a straight configuration.

D. Exemplary Pegged Rigidizing Member

FIGS. 19-21B show a rigidizing member (260) that may be used in lieu of rigidizing member (240) discussed above. As best seen in FIGS. 19 and 20, rigidizing member (260) of the present example comprises an elongate shaft (262), having a rectangular cross-section, and a plurality of pegs (264) extending transversely from a side surface of shaft (262). As will be described in more detail below, rigidizing member (260) is laterally translatable within an interior space of shaft assembly (30) between a first position (FIG. 21A) and a second position (FIG. 21B). Also as will be described in more detail below, when in the first position, pegs (264) of rigidizing member (260) function to provide rigidity to articulation section (130) and/or to prevent inadvertent deflection of end effector (40) relative to outer sheath (32).

As shown in FIGS. 21A and 21B, rigidizing member (260) is configured to be positioned within an interior space of shaft assembly (30), including articulation section (130). As shown in FIG. 21A, with rigidizing member (260) positioned within the interior space of shaft assembly (30) in the first position, pegs (264) are configured to extend through V-shaped pockets (236) and bear against (or at least contact) angled surfaces (234) of couplers (230) to thereby provide rigidity to articulation section (130) and/or to prevent inadvertent deflection of end effector (40) relative to outer sheath (32). As shown in FIG. 21B, rigidizing member (260) is translated laterally inwardly into the second position to thereby draw pegs (264) inwardly from V-shaped pockets (236) such that pegs (264) no longer bear against (or otherwise contact) angled surfaces (234) of couplers (230). With pegs (264) moved out of V-shaped pockets (236), articulation section (130) is free to flex to thereby deflect end effector (40) relative to outer sheath (32). Various suitable ways in which rigidizing member (260) may be actuated between the positions shown in FIGS. 21A and 21B will be apparent to those of ordinary skill in the art in view of the teachings herein.

E. Exemplary Variable-Thickness Rigidizing Member and Couplers

FIGS. 22-23C show a variable-thickness rigidizing member (280) that may be incorporated into articulation section (130) of shaft assembly (30) of instrument (10). As will be described in more detail below, rigidizing member (280) may function to selectively provide rigidity to articulation section (130) and/or to prevent inadvertent deflection of end effector (40) relative to outer sheath (32). As best seen in FIG. 22, rigidizing member (280) of the present example comprises a plurality of flanges (282) linked to one another by a plurality of flexible rods (284), which are positioned between consecutive flanges (282). It should be understood that rods (284) may be substituted with wires, cables, or any other suitable kind of flexible member. As will be described in more detail below, rigidizing member (280) is longitudinally translatable along a length of shaft assembly (30) so as to transition flanges (282) between a first position (FIG. 23A) and a second position (FIGS. 23B and 23C). Also as will be described in more detail below, when in the first position, flanges (282) of rigidizing member (280) function to provide rigidity to articulation section (130) and/or to prevent inadvertent deflection of end effector (40) relative to outer sheath (32).

In the present example a modified version of shaft assembly (30) comprises a plurality of couplers (290) that are pivotably linked to one another via a plurality of pins (292). Couplers (290) are disposed about shaft assembly (30), including articulation section (130). A distal-most coupler (290A) of couplers (290) is secured to an exterior surface of distal outer sheath (33) of shaft assembly (30) distally of articulation section (130). A proximal-most coupler (290B) of couplers (290) is secured to an exterior surface of outer sheath (32) of shaft assembly (30) proximally of articulation section (130). Thus, when linked to one another via pins (292), couplers (290) completely encompass articulation section (130). As mentioned above, couplers (290) are pivotably linked to one another via a plurality of pins (292) such that couplers (290) pivot about a plurality of axes defined by pins (292). Pins (292), which pivotably link couplers (290) to one another, are aligned such that articulation section (130) may flex along a plane (P1) oriented perpendicular to the axes of rotation of pins (292).

As shown in FIGS. 23A-23C, rigidizing member (280) is configured to be positioned within an interior space of shaft assembly (30), including articulation section (130), inside the assembly formed by couplers (290). Rigidizing member (280) is oriented such that flanges (282) are substantially parallel to plane (P1) and perpendicular to the axes of rotation of pins (292). As shown in FIG. 23A, with flanges (282) in the first position, flanges (282) of rigidizing member (280) are positioned such that each flange (282) extends between a space defined by consecutive couplers (290) and such that pins (292) are positioned above and below an intermediate portion of flanges (282). Because flanges (282) are positioned at the joints of couplers (290), flanges (282) prevent couplers (290) from flexing at those joints. This further prevents flexing at articulation section. Thus, when rigidizing member (280) is in the position shown in FIG. 23A, the assembly formed by rigidizing member (280) and couplers (290) prevents bending of articulation section (130) and effectively rigidizes articulation section (130).

As shown in FIGS. 23B and 23C, rigidizing member (280) is translated proximally so as to move flanges (282) away from the joints of couplers (290) and to position flexible rods (284) at the joints of couplers (290). This positioning enables couplers (290) to pivot at the joints. With couplers (290) being enabled to pivot, and with flexible rods (284) being enabled to flex, articulation section (130) is thereby enabled to articulate as shown in FIG. 23C. Various suitable ways in which rigidizing member (280) may be actuated between the position shown in FIG. 23A and the positions shown in FIGS. 23B-23C will be apparent to those of ordinary skill in the art in view of the teachings herein.

F. Exemplary Variable-Thickness Rigidizing Member

Figure 28:
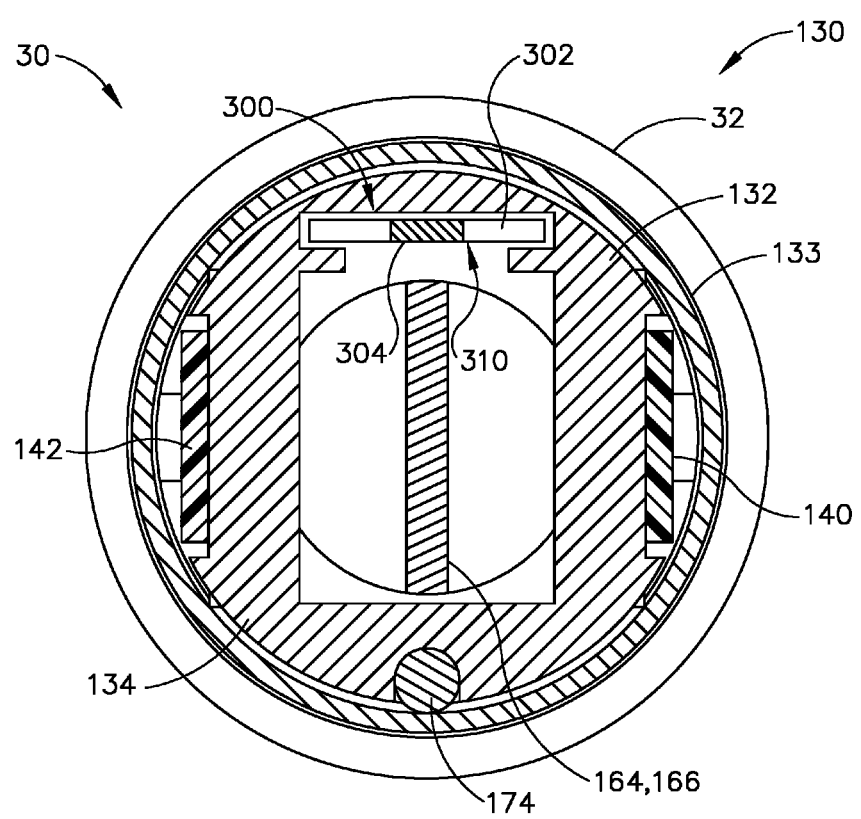
FIG. 28 depicts a cross-sectional front view of the modified shaft assembly of FIG. 24 with the structural feature of FIG. 24 positioned therein.
Figure 29C:
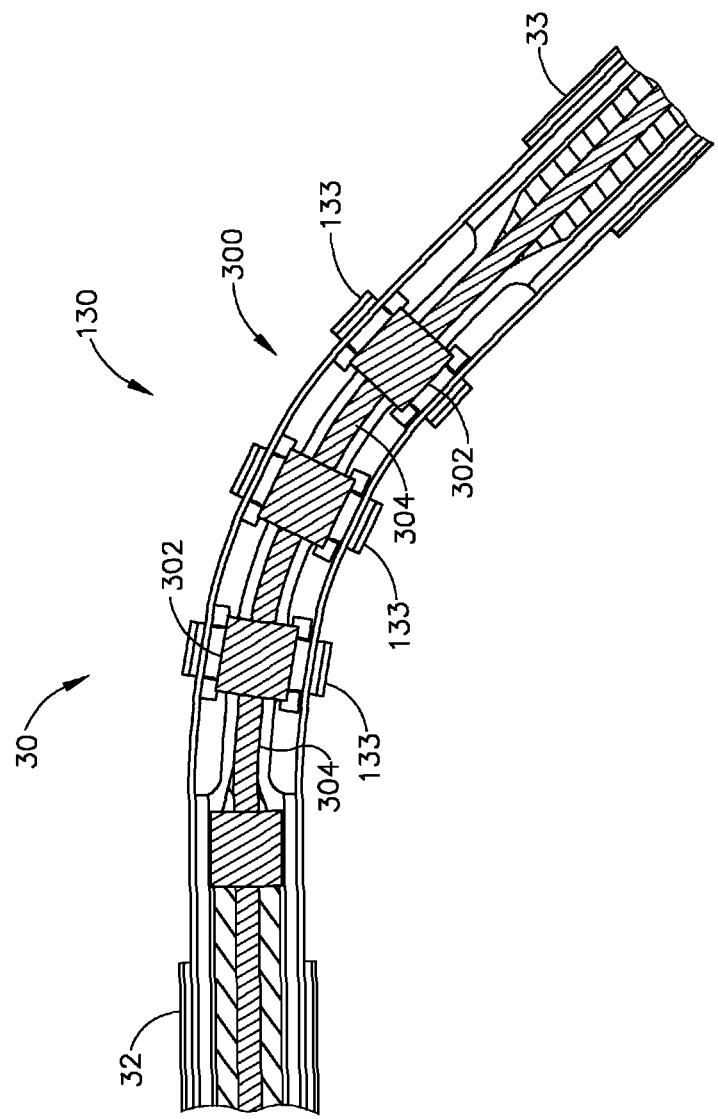
FIG. 29C depicts a detailed cross-sectional top plan view of the modified shaft assembly of FIG. 24 in an articulated configuration with the structural feature of FIG. 24 positioned therein in the proximal longitudinal position.

FIGS. 24-29C show shaft assembly (30) of instrument (10) described above having a variable-thickness rigidizing member (300) incorporated therein. As will be described in more detail below, rigidizing member (300) may function to selectively provide rigidity to articulation section (130) and/or to prevent inadvertent deflection of end effector (40) relative to outer sheath (32). As best seen in FIG. 25, rigidizing member (300) of the present example comprises a plurality of flanges (302) linked to one another by a plurality of flexible rods (304) that are positioned between consecutive flanges (302). It should be understood that rods (304) may be substituted with wires, cables, or any other suitable kind of flexible member. As shown in FIG. 26, flanges (302) of the present example have a rectangular cross-section. In some other versions, flanges (302) have a circular segment cross-section as shown in FIG. 27. Alternatively, flanges (302) may have any other suitable cross-section as will be appreciated by one of ordinary skill in the art in view of the teachings herein. As will be described in more detail below, rigidizing member (300) is longitudinally translatable along a length of shaft assembly (30) so as to transition flanges (302) between a first position (FIG. 29A) and a second position (FIGS. 29B and 29C). As will also be described in more detail below, when rigidizing member (300) is in the first position, flanges (302) of rigidizing member (300) function to provide rigidity to articulation section (130) and/or to prevent inadvertent deflection of end effector (40) relative to outer sheath (32).

As shown in FIG. 28, shaft assembly (30) of the present example, including articulation section (130), defines a channel (310) in a top portion of ribbed body portions (132, 134) of articulation section (130). Channel (310) is configured to slidably receive rigidizing member (300) such that rigidizing member (300) is longitudinally translatable within channel (310) along a length of shaft assembly (30).

As shown in FIGS. 29A-29C, rigidizing member (300) is configured to be positioned within an interior space of shaft assembly (30), including articulation section (130). Rigidizing member (300) is oriented such that flanges (302) are substantially parallel to a plane (P2) along which articulation member (130) is configured to flex. As shown in FIG. 29A, with flanges (302) in the first position, flanges (302) of rigidizing member (300) are positioned such that each flange (302) extends between the spaces between consecutive retention collars (133). Because of the orientation and position of flanges (302) in this state, and because of the width of flanges (302), flanges (302) block relative movement of retention collars (133) along plane (P2). Rigidizing member (300) thus prevents bending of articulation section (130) and effectively rigidizes articulation section (130).

As shown in FIGS. 29B and 29C, rigidizing member (300) is translated proximally so as to position flanges (302) away from the spaces between consecutive retention collars (133) and to position flexible rods (304) between the spaces between consecutive retention collars (133). This positioning enables retention collars (133) to move relative to each other along plane (P2). With such movement of collars (133) enabled, and with flexible rods (304) being enabled to flex, articulation section (130) is thereby enabled to articulate as shown in FIG. 29C. Various suitable ways in which rigidizing member (300) may be actuated between the position shown in FIG. 29A and the positions shown in FIGS. 29B-29C will be apparent to those of ordinary skill in the art in view of the teachings herein.

G. Exemplary Rigidizing Sleeve Member

Figure 32C:
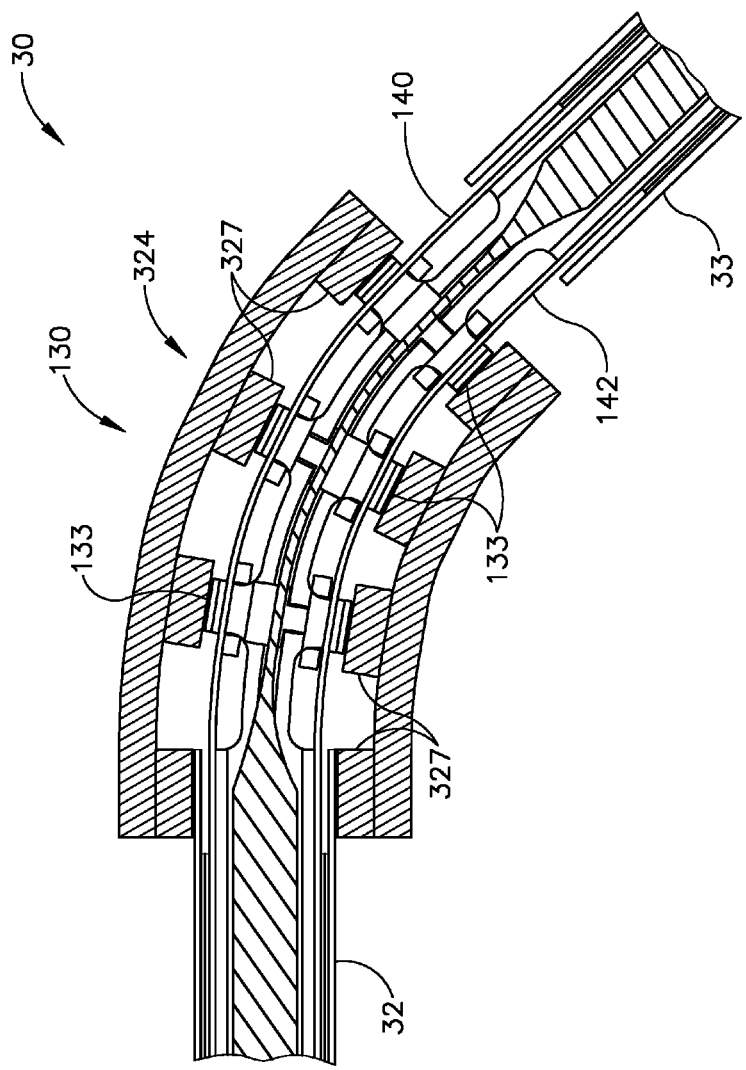
FIG. 32C depicts a detailed cross-sectional top plan view of the modified shaft assembly of FIG. 32A in an articulated configuration with the structural feature of FIG. 30 positioned thereabout in the proximal longitudinal position.

FIGS. 30-32C show an exemplary rigidizing sleeve member (320). As will be described in more detail below, rigidizing sleeve member (320) may function to selectively provide rigidity to articulation section (130) and/or to prevent inadvertent deflection of end effector (40) relative to outer sheath (32). As best seen in FIG. 30, rigidizing member (320) of the present example comprises a proximal semi-circular-cylindrical portion (322) and a distal semi-circular-cylindrical portion (324). Portions (322, 324) are coupled together via a flexible rod (326). Rod (326) provides lateral flexibility yet has sufficient column strength to provide effective actuation of rigidizing sleeve member (320) as described below. It should be understood that rod (326) may be substituted with a band or any other suitable kind of flexible member. Cylindrical portions (322, 324) are sized to receive and selectively couple about shaft assembly (30) in a snap-fit manner. As will be described in more detail, however, sleeve member (320) remains able to translate longitudinally along a length of shaft assembly (30) so as to transition distal cylindrical portion (324) between a first position (FIG. 32A) and a second position (FIGS. 32B and 32C). Also as will be described in more detail below, when sleeve member (320) is in the first position, distal cylindrical portion (324) of sleeve member (320) functions to provide rigidity to articulation section (130) and/or to prevent inadvertent deflection of end effector (40) relative to outer sheath (32).

As best seen in FIG. 30, proximal cylindrical portion (322) comprises a pair of flanges (328) extending from opposing sides of an exterior surface of proximal cylindrical portion (322). A user may engage flanges (328) to assist the user in positioning proximal cylindrical portion (322) about and removing proximal cylindrical portion (322) from shaft assembly (30). Alternatively, any other suitable features may be used to facilitate manipulation of proximal cylindrical portion (322). As shown in FIG. 31, distal cylindrical portion (324) comprises a plurality of rectangular projections (327) extending inwardly from an interior surface of distal cylindrical portion (324).

As shown in FIGS. 32A-32C, and as discussed above, distal cylindrical portion (324) is configured to be positioned about shaft assembly (30), in particular, about articulation section (130). As shown in FIG. 32A, with distal cylindrical portion (324) in the first position, projections (327) of distal cylindrical portion (324) are positioned such that each projection (327) is positioned within a corresponding space defined between consecutive retention collars (133) such that projections (327) abut consecutive retention collars (133). Because projections (327) abut consecutive retention collars (133) when sleeve member (320) is in the first position, projections (327) function to provide rigidity to articulation section (130) and/or to prevent inadvertent deflection of end effector (40) relative to outer sheath (32) by preventing movement of retention collars (133) relative to each other.

As shown in FIGS. 32B and 32C, rigidizing sleeve member (320) is translated proximally so as to draw projections (327) from the spaces defined by consecutive retention collars (133) and so as to position projections (327) adjacent an exterior surface of retention collars (133). With sleeve member (320) in this position, the space between consecutive retention collars (133) allows articulation section (130) to flex to thereby deflect end effector (40) relative to outer sheath (32) as shown in FIG. 32C.

Distal cylindrical portion (324) is formed of a resilient material that enables projections (327) to deflect outwardly from the position shown in FIG. 32A to the position shown in FIGS. 32B and 32C. The resilient properties of distal cylindrical portion (324) also cause projections (327) to snap back into the spaces defined between consecutive retention collars (133) when sleeve member (320) is advanced distally back to the position shown in FIG. 32A. In the present example, sleeve member (320) may be returned to the position shown in FIG. 32A after articulation section (130) has been returned to a straight, non-articulated configuration. Also in the present example, sleeve member (320) is translated between the distal position (FIG. 32A) and the proximal position (FIGS. 32B and 32C) by an operator grasping proximal cylindrical portion (322) and thereby sliding sleeve member (320) along shaft assembly (30). Other suitable ways in which sleeve member (320) may be actuated will be apparent to those of ordinary skill in the art in view of the teachings herein.

H. Exemplary C-Channel Rigidizing Member

Figure 33:
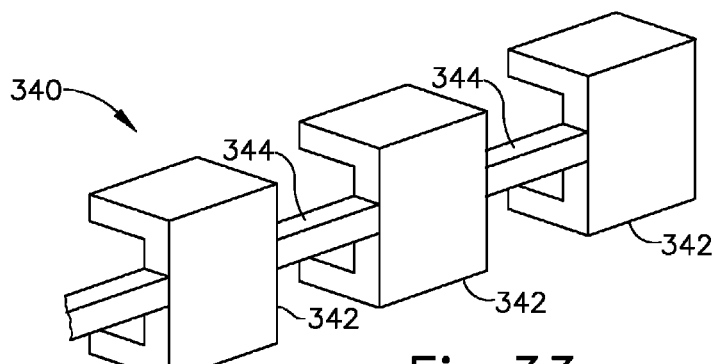
FIG. 33 depicts a perspective view of yet another exemplary structural feature that may be incorporated into the shaft assembly of FIG. 2.
Figure 34:
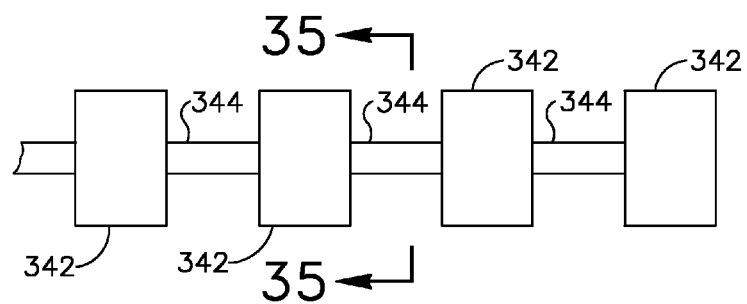
FIG. 34 depicts a side view of the structural feature of FIG. 33.
Figure 35:
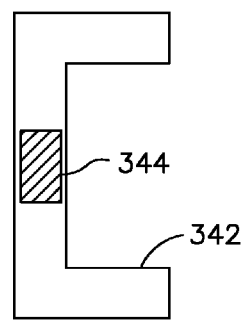
FIG. 35 depicts a cross-sectional front view of the structural feature of FIG. 33, taken along line 35-35 of FIG. 34.

FIGS. 33-37B show another exemplary rigidizing member (340). As will be described in more detail below, rigidizing member (340) may function to selectively provide rigidity to articulation section (130) and/or to prevent inadvertent deflection of end effector (40) relative to outer sheath (32). As best seen in FIG. 33, rigidizing member (340) of the present example comprises a plurality of C-channel members (342) linked to one another by a plurality of flexible rods (344), which are positioned between consecutive C-channel members (342). It should be understood that rods (344) may be substituted with wires, cables, or any other suitable kind of flexible member. As will be described in more detail below, rigidizing member (340) is configured to translate longitudinally along a length of shaft assembly (30) so as to transition C-channel members (342) between a first position (FIG. 36A) and a second position (FIGS. 36B and 36C). Also as will be described in more detail below, when rigidizing member (340) is in the first position, C-channel members (342) of rigidizing member (340) function to provide rigidity to articulation section (130) and/or to prevent inadvertent deflection of end effector (40) relative to outer sheath (32).

Figure 36C:
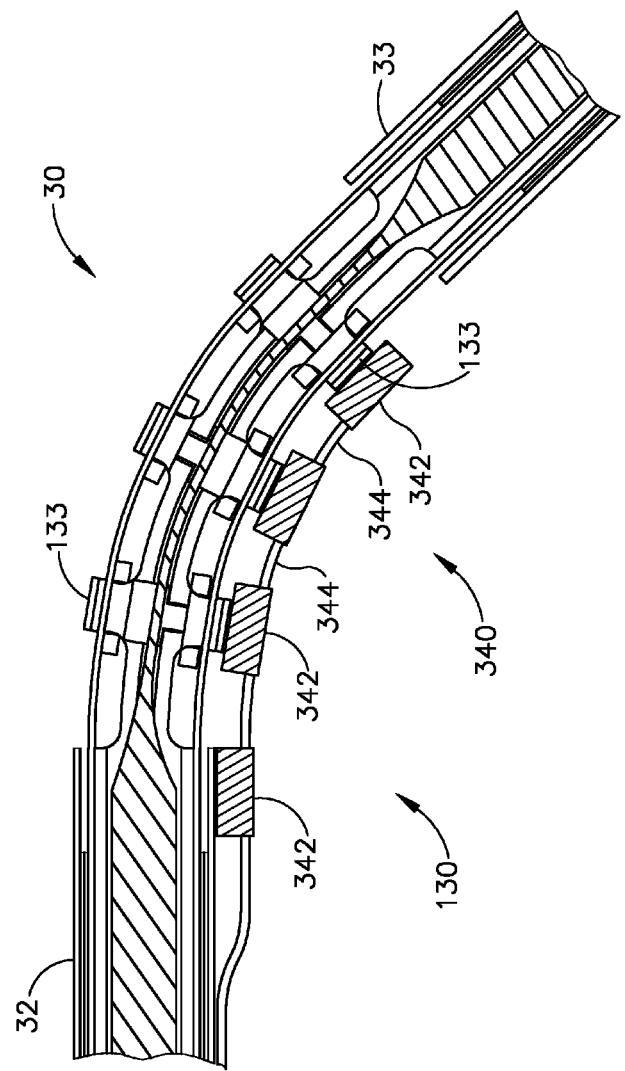
FIG. 36C depicts a detailed cross-sectional top plan view of the modified shaft assembly of FIG. 36A in an articulated configuration with the structural feature of FIG. 33 positioned thereabout in the proximal longitudinal position.

As shown in FIGS. 36A-36C, C-channel members (342) are configured to be positioned about shaft assembly (30), in particular, about articulation section (130). As shown in FIG. 36A, with rigidizing member (340) in the first position, C-channel members (342) are positioned such that each C-channel member (342) is positioned within a corresponding space defined between consecutive retention collars (133) such that C-channel members (342) abut consecutive retention collars (133). Because C-channel members (342) abut consecutive retention collars (133) when rigidizing member (340) is in the first position, C-channel members (342) function to provide rigidity to articulation section (130) and/or to prevent inadvertent deflection of end effector (40) relative to outer sheath (32) by preventing movement of retention collars (133) relative to each other.

As shown in FIGS. 36B and 36C, rigidizing member (340) is translated proximally so as to draw C-channel members (342) from the spaces defined between consecutive retention collars (133) and so as to position C-channel members (342) adjacent an exterior surface of retention collars (133). With rigidizing member (340) in this position, the space between consecutive retention collars (133) allows articulation section (130) to flex to thereby deflect end effector (40) relative to outer sheath (32) as shown in FIG. 36C.

Rigidizng member (340) is formed of a resilient material that enables C-channel members (342) to deform and deflect outwardly from the position shown in FIG. 36A to the position shown in FIGS. 36B and 36C. The resilient properties of C-channel members (342) also cause C-channel members (342) to snap back into the spaces defined between consecutive retention collars (133) when rigidizing member (340) is advanced distally back to the position shown in FIG. 36A. In the present example, rigidizing member (340) may be returned to the position shown in FIG. 36A after articulation section (130) has been returned to a straight, non-articulated configuration. Various suitable ways in which rigidizing member (340) may be actuated will be apparent to those of ordinary skill in the art in view of the teachings herein.

Although the example discussed above is provides just a single rigidizing member (340), on just one side of articulation section (130), it should be understood that two or more rigidizing members (340) may be used. For instance, as shown in FIGS. 37A and 37B, a pair of rigidizing members (340) may be positioned on opposite lateral sides of articulation section (130) to provide rigidity to articulation section (130) and/or to prevent inadvertent deflection of end effector (40) relative to outer sheath (32) in multiple directions.

I. Exemplary Rigidizing Clip Member

FIGS. 38-39B show an exemplary rigidizing clip member (360). As will be described in more detail below, rigidizing clip member (360) may function to selecitively provide rigidity to articulation section (130) and/or to prevent inadvertent deflection of end effector (40) relative to outer sheath (32). As best seen in FIG. 38, rigidizing clip member (360) of the present example comprises a semi-circular-cylindrical body (362). A plurality of slots (364) formed in opposing side surfaces of cylindrical body (362) separate a plurality of tabs (366). As shown in FIGS. 39A and 39B, rigidizing clip member (360) is configured to be positioned about shaft assembly (30), in particular, about articulation section (130).

As shown in FIG. 39A, spaces defined between consecutive retention collars (133) provide clearance allowing articulation section (130) to flex to thereby deflect end effector (40) relative to outer sheath (32). As shown in FIG. 39B, with rigidizing clip member (360) positioned about articulation section (130), tabs (366) are positioned such that each tab (366) is positioned within the space defined by consecutive retention collars (133). Tabs (366) abut consecutive retention collars (133) in this state. Because tabs (366) abut consecutive retention collars (133), tabs (366) function to provide rigidity to articulation section (130) and/or to prevent inadvertent deflection of end effector (40) relative to outer sheath (32) by preventing movement of retention collars (133) toward one another. It should be understood that clip member (360) may be formed of a resilient material such that clip member (360) may be removably secured to articulation section (130) through a snap fit. Alternatively, clip member (360) may be removably secured to articulation section (130) in any other suitable fashion.

J. Exemplary Dual Structural Bands

FIGS. 40A-43B show a modified version of shaft assembly (30) of instrument (10) described above having a pair of overlapping articulation bands (380, 390). As will be described in more detail below, articulation bands (380, 390) may function to provide rigidity to articulation section (130) and/or to prevent inadvertent deflection of end effector (40) relative to outer sheath (32). As best seen in FIG. 41, articulation band (380) comprises an elongate strip (382) having a plurality of circular openings (384) formed therein to provide "weak spots" along the length of strip (382). Circular openings (384) are spaced apart from one another, and provide flexibility to articulation band (380) at circular openings (384). As best seen in FIG. 42, articulation band (390) comprises an elongate strip (392) having a plurality of opposing rectangular recesses (394) formed therein to provide "weak spots" along the length of strip (392). Rectangular recesses (394) are spaced apart from one another, and provide flexibility to articulation band (390) at rectangular recesses (394). The spacing of recesses (394) corresponds to the spacing of openings (384).

Figure 40B:
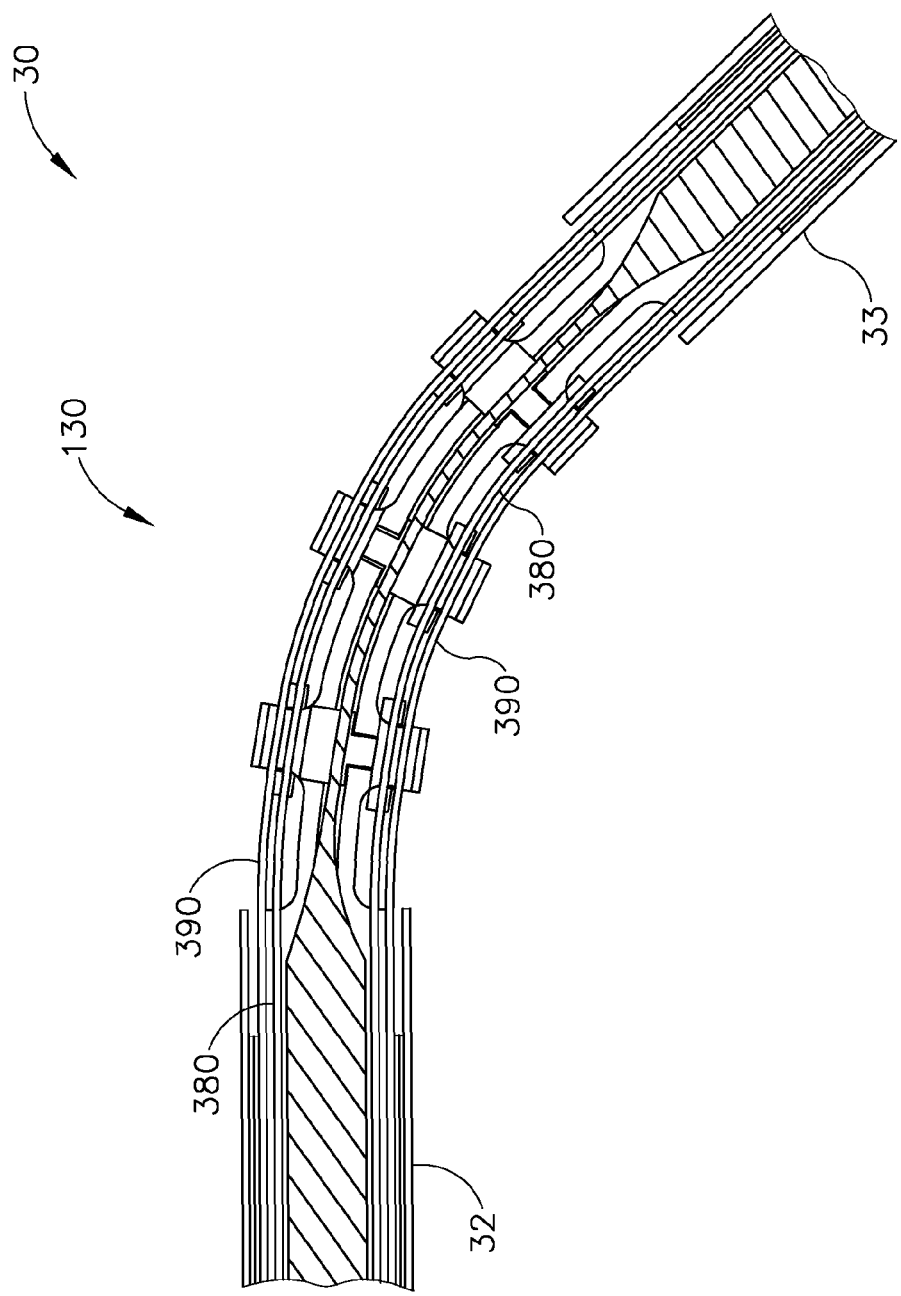
FIG. 40B depicts a detailed cross-sectional top plan view of the modified shaft assembly of FIG. 40A in an articulated configuration.

As shown in FIGS. 40A and 40B, articulation bands (380, 390) are positioned within an interior space of shaft assembly (30), including articulation section (130). One set of articulation bands (380, 390) is positioned on one side of waveguide (180); while another set of articulation bands (380, 390) is positioned on the other side of waveguide (180). Articulation bands (380, 390) are longitudinally translatable relative to one another between a first configuration (FIG. 43A) and a second configuration (FIG. 43B). As shown in FIG. 43A, in the first configuration, articulation bands (380, 390) overlap one another in an arrangement such that circular openings (384) of articulation band (380) are offset from rectangular recesses (394) of articulation band (390). With these "weak spots" of articulation bands (380, 390) offset from one another, the remaining "strong spots" of articulation bands (380, 390) accommodate for the "weak spots" and prevent articulation bands (380, 390) from flexing. Articulation bands (380, 390) thus cooperate to provide rigidity to articulation section (130) and/or prevent inadvertent deflection of end effector (40) relative to outer sheath (32) when articulation bands (380, 390) are arranged as shown in FIG. 43A. In the present example, articulation bands (380, 390) are positioned in this arrangement when articulation section (130) is in a straight, non-articulated configuration as shown in FIG. 40A.

As shown in FIG. 43B, in the second configuration, articulation bands (380, 390) overlap one another in an arrangement such that circular openings (384) of articulation band (380) align with rectangular recesses (394) of articulation band (390). With these "weak spots" of articulation bands (380, 390) aligned, articulation bands (380, 390) may flex to thereby allow articulation section (130) to flex to thereby deflect end effector (40) relative to outer sheath (32). In other words, articulation bands (380, 390) cooperate to provide flexibility to articulation section (130) when articulation bands (380, 390) are arranged as shown in FIG. 43B. While the "weak spots" of articulation bands (380, 390) are formed as circular openings (384) and rectangular recesses (394) in the present example, it should be understood that the "weak spots" may have any other suitable configurations. Various suitable alternative configurations for "weak spots" will be apparent to those of ordinary skill in the art in view of the teachings herein.

Articulation control assembly (100) may be readily modified to provide coordinated movement of articulation bands (380, 390). For instance, in one merely illustrative example, articulation control assembly (100) is configured such that knob (120) is rotatable through two ranges of motion from a neutral position where articulation section (130) is in a straight, non-articulated configuration as shown in FIG. 40A. With knob (120) in the neutral position, articulation bands (380, 390) are in the arrangement shown in FIG. 43A, such that articulation bands (380, 390) rigidize articulation section (130), with articulation section (130) being in the straight, non-articulated configuration. When knob (120) is rotated through a first range of motion from the neutral position, articulation control assembly (100) drives a first articulation band (380, 390) in each pair of articulation bands (380, 390) relative to a second articulation band (380, 390) in that pair. The second articulation band (380, 390) remains stationary during this first range of motion of knob (120).

When knob (120) completes the first range of motion, each pair of articulation bands (380) is transitioned to the configuration shown in FIG. 43B, such that articulation bands (380, 390) are arranged to provide flexibility. When the operator then rotates knob (120) through a second range of motion after completing the first range of motion, articulation control assembly (100) drives a both articulation bands (380, 390) of one pair together in a first longitudinal direction, while simultaneously driving both articulation bands (380, 390) of the other pair together in a second longitudinal direction. The pairs of articulation bands (380, 390) thus cooperate to drive articulation as knob (120) is rotated through the second range of motion.

When the operator wishes to subsequently transition articulation section (130) back to a straight, non-articulated state, the operator may simply reverse rotation of knob (120). During this reversal, the pairs of articulation bands (380, 390) will again cooperate to drive articulation section (130) back to the straight, non-articulated state. Once articulation section (130) reaches the straight, non-articulated state, knob (120) will transition from the second range of motion back to the first range of motion as knob (120) is further rotated. As knob (120) is rotated back through the first range of motion toward the neutral position, articulation control assembly (100) again drives a first articulation band (380, 390) in each pair of articulation bands (380, 390) relative to a second articulation band (380, 390) in that pair. The second articulation band (380, 390) remains stationary during this first range of motion of knob (120). Once knob (120) reaches the neutral position again, articulation bands (380, 390) are again returned to the arrangement shown in FIG. 43A, such that articulation bands (380, 390) again rigidize articulation section (130). Various structures and features that may be incorporated into articulation control assembly (100) in order to provide the above described operation will be apparent to those of ordinary skill in the art in view of the teachings herein.

While knob (120) is used in the present example, it should be understood that any other suitable kind of actuator may be used, including but not limited to a slider, a lever, a dial, etc. In addition, in the present example knob (120) is operable to both selectively rigidize articulation section (130) (as knob (120) is rotated through the first range of motion) and to drive articulation of articulation section (130) (as knob (120) is rotated through the second range of motion). In some other versions, two separate actuators are used—one actuator to selectively rigidize articulation section (130) and another actuator to drive articulation of articulation section (130).

It should also be understood that any other example described herein for selectively rigidizing articulation section (130) may also be coupled with a modified version of articulation control assembly (100) as described above. In other words, any other example described herein for selectively rigidizing articulation section (130) may be coupled with a knob (120) that rotates through two ranges of motion—a first range of motion to selectively rigidize articulation section (130) and a second range of motion to drive articulation of articulation section (130). Similarly, any other kind of actuator may be used, including but not limited to a slider, a lever, a dial, etc. Such alternative actuators may also be moved through two different ranges of motion to selectively rigidize articulation section (130) (during a first range of motion of the actuator) and to drive articulation of articulation section (during a second range of motion of the actuator). Furthermore, any other example described herein for selectively rigidizing articulation section (130) may also be coupled with two separate actuators—one actuator to selectively rigidize articulation section (130) and another actuator to drive articulation of articulation section (130). Various suitable ways in which these exemplary alternatives may be incorporated into the various examples described herein will be apparent to those of ordinary skill in the art in view of the teachings herein.

K. Exemplary Rigidizing Tubular Member

FIG. 44 shows a modified version of shaft assembly (30) of instrument (10) having a tubular member (400) that is configured to selectively rigidize. As will be described in more detail below, tubular member (400) may function to selectively provide rigidity to articulation section (130) and/or to prevent inadvertent deflection of end effector (40) relative to outer sheath (32). Tubular member (400) comprises hollow-cylindrical body (402) filled with magnetorheological fluid (MR fluid) (404). Cylindrical body (402) is positioned about shaft assembly (30) and encompasses articulation section (130). Cylindrical body (402) is capped at a distal end and a proximal end by a pair of magnets (406), In the present example, magnets (406) comprise electromagnets, such that magnets (406) may be selectively activated (and thereby be selectively magnetized) by application of an electric current to magnets (406). A distal magnet (406A) of magnets (406) is secured to an exterior surface of distal outer sheath (33) of shaft assembly (30) distally of articulation section (130). A proximal magnet (406B) of magnets (406) is secured to an exterior surface of outer sheath (32) of shaft assembly (30) proximally of articulation section (130).

Magnets (406) are in direct contact with MR fluid (404) such that magnets (406) may function to selectively magnetize MR fluid (404) based on selective activation of magnets (406). Prior to magnetizing MR fluid (404), cylindrical body (402) of tubular member (400) is operable to flex to thereby allow articulation section (130) to flex to thereby deflect end effector (40) relative to outer sheath (32). Once MR fluid (404) is magnetized via activation of magnets (406), however, MR fluid (404) becomes substantially rigid within cylindrical body (402) to thereby rigidize tubular member (400). Once tubular member (400) is rigidized, tubular member (400) may function to provide rigidity to articulation section (130) and/or to prevent inadvertent deflection of end effector (40) relative to outer sheath (32).

By way of example only, one or more wires, conductive traces, and/or other electrically conductive conduits may extend along the length of shaft assembly (30) to enable electrical power to be selectively delivered to magnets (406). In one merely illustrative example, articulation control assembly (100) is modified such that knob (120) causes closure of an electrical switch when knob (120) is rotated to a neutral position that is associated with articulation section (130) being in a straight, non-articulated configuration. This switch may be in communication with magnets (406) and a source of electrical power such that magnets (406) are activated when knob (120) is in the neutral position. Articulation section (130) will thus be rigidized when knob (120) is in the neutral position, with articulation section (130) in the straight, non-articulated configuration. As soon as knob (120) is rotated away from the neutral position to articulate articulation section (130), the switch will be transitioned to an open state, thereby deactivating magnets (406), thereby de-rigidizing articulation section (130) and allowing articulation section (130) to be articulated. When knob (120) is subsequently rotated back to the neutral position, the switch will again be closed, thereby re-activating magnets (406), thereby rigidizing articulation section (130) again as articulation section (130) reaches the straight, non-articulated configuration. Various other suitable ways in which magnets (406) may be selectively activated will be apparent to those of ordinary skill in the art in view of the teachings herein.

L. Exemplary Rigidizing Valve Assembly

FIG. 45 shows a modified version of shaft assembly (30) of instrument (10) described above having a valve assembly (420). As will be described in more detail below, valve assembly (420) is configured to selectively rigidize so as to provide rigidity to articulation section (130) and/or to prevent inadvertent deflection of end effector (40) relative to outer sheath (32). Valve assembly (420) comprises a pair of plungers (422, 424) that are slidably disposed within a pair of cylinders (426, 428). Plungers (422, 424) are coupled with articulation bands (140, 142) of shaft assembly (130) such that translation of articulation bands (140, 142) caused by articulation of articulation section (130) causes concurrent translation of plungers (422, 424) within cylinders (426, 428). Cylinders (426, 428) are filled with MR fluid (430, 432). One or more electromagnets (not shown) are in direct contact with MR fluid (430, 432) such that the electromagnets may selectively magnetize MR fluid (430, 4 when the electromagnets are activated. Prior to magnetizing MR fluid (430, 432), plungers (422, 424) are operable to translate within cylinders (426, 428) to thereby allow articulation section (130) to flex to thereby deflect end effector (40) relative to outer sheath (32). Once MR fluid (430, 432) is magnetized, however, MR fluid (430, 432) becomes substantially rigid within cylinders (426, 428) to thereby prevent movement of plungers (422, 424) to thereby prevent movement of articulation bands (140, 142) so as to provide rigidity to articulation section (130) and/or to prevent inadvertent deflection of end effector (40) relative to outer sheath (32). Various suitable ways in which MR fluid (430, 432) may be selectively magnetized will be apparent to those of ordinary skill in the art in view of the teachings herein.

M. Exemplary Stiffening Friction Features

Figure 46:
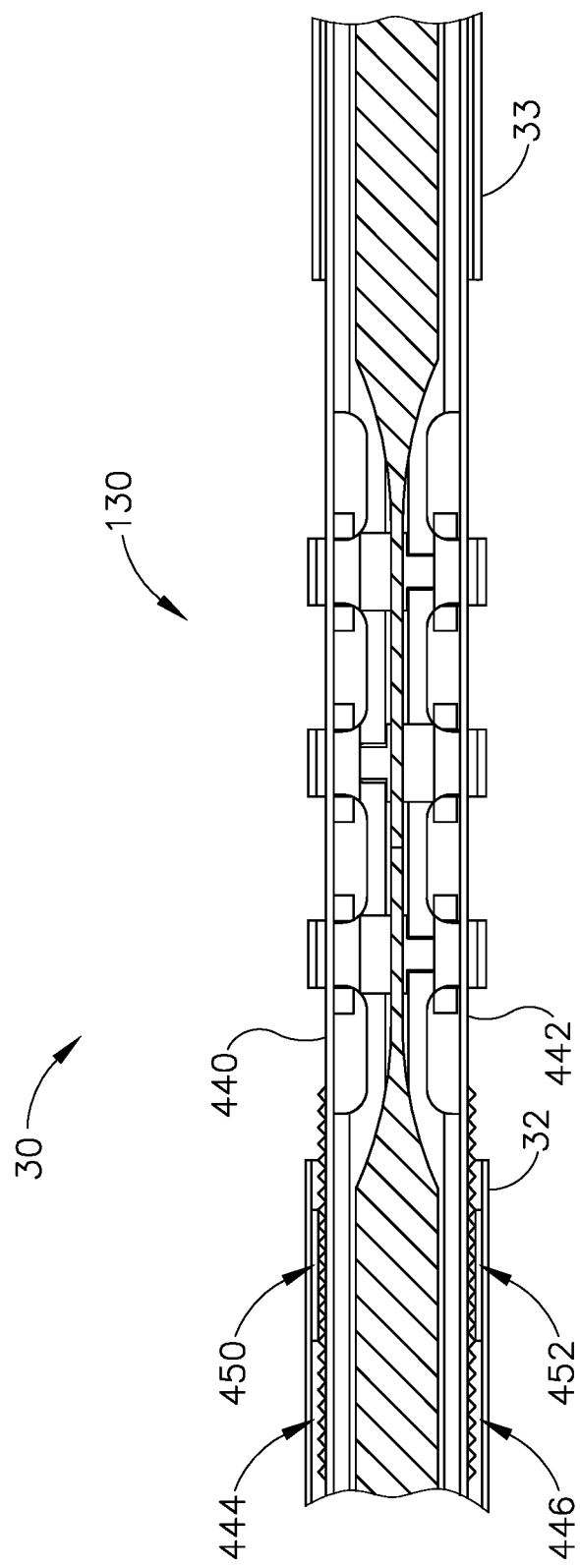
FIG. 46 depicts a detailed cross-sectional top plan view of a modified version of the shaft assembly of FIG. 2 having yet another exemplary structural feature.

FIG. 46 shows a modified version shaft assembly (30) of instrument (10) described above having a pair of exemplary alternative articulation bands (440, 442). As will be described in more detail below, articulation bands (440, 442) may function to provide rigidity to articulation section (130) and/or to prevent inadvertent deflection of end effector (40) relative to outer sheath (32). Each articulation band (440, 442) comprises a plurality of teeth (444, 446) projecting outwardly from opposing side surfaces of articulation bands (440, 442). An interior surface of outer sheath (32) comprises two sets of teeth (450, 452) projecting inwardly from opposing sides of an interior surface of outer sheath (32). Teeth (444, 446) of articulation bands (440, 442) are configured to engage teeth (450, 452) of outer sheath (32) to thereby limit longitudinal translation of articulation bands (440, 442). Limiting the longitudinal translation of articulation bands (440, 442) subsequently limits articulation of articulation section (130). Thus, it should be understood that depending upon the amount of engagement between teeth (444, 446) of articulation bands (440, 442) and teeth (450, 452) of outer sheath (32), teeth (444, 446, 450, 452) may function to merely limit actuation of articulation section (130) or to substantially limit actuation of articulation section (130) by requiring a lesser or greater force to articulate articulation section (130).

In some versions, articulation bands (440, 442) are configured to transition laterally between an inward configuration and an outward configuration. When articulation bands (440, 442) are in the inward configuration, teeth (444, 446) are disengaged from teeth (450, 452), allowing articulation bands (440, 442) to translate freely (e.g., to freely drive articulation of articulation section (130)). When articulation bands (440, 442) are in the outward configuration, teeth (444, 446) are engaged with teeth (450, 452), with enough force to prevent articulation bands (440, 442) from translating. With articulation bands (440, 442) being rigidly prevented from translating, articulation section (130) is effectively rigidized. Various suitable ways in which articulation bands (440, 442) may be selectively transitioned between the inward configuration and the outward configuration will be apparent to those of ordinary skill in the art in view of the teachings herein.

In some other versions, articulation bands (440, 442) are resiliently biased outwardly such that teeth (444, 446) are biased into engagement with teeth (450, 452). Teeth (444, 446) remain engaged with teeth (450, 452), yet teeth (444, 446) are permitted to slide along teeth (450, 452) in a ratcheting fashion as articulation bands (440, 442) are opposingly translated to drive articulation of articulation section (130). When articulation bands (440, 442) are held longitudinally stationary, engagement between teeth (444, 446) and teeth (450, 452) will prevent articulation section (130) from having any "play", such that teeth (444, 446) and teeth (450, 452) cooperate to effectively rigidize articulation section (130). It should be noted that teeth (444, 446) and teeth (450, 452) are positioned proximate to articulation section (130) in this example, thereby minimizing any tolerance stacking that might otherwise frustrate the rigidization functionality in cases where teeth (444, 446) and teeth (450, 452) would be positioned further remotely from articulation section (130).

N. Exemplary "Smart Material" Articulation Bands

Figure 47A:
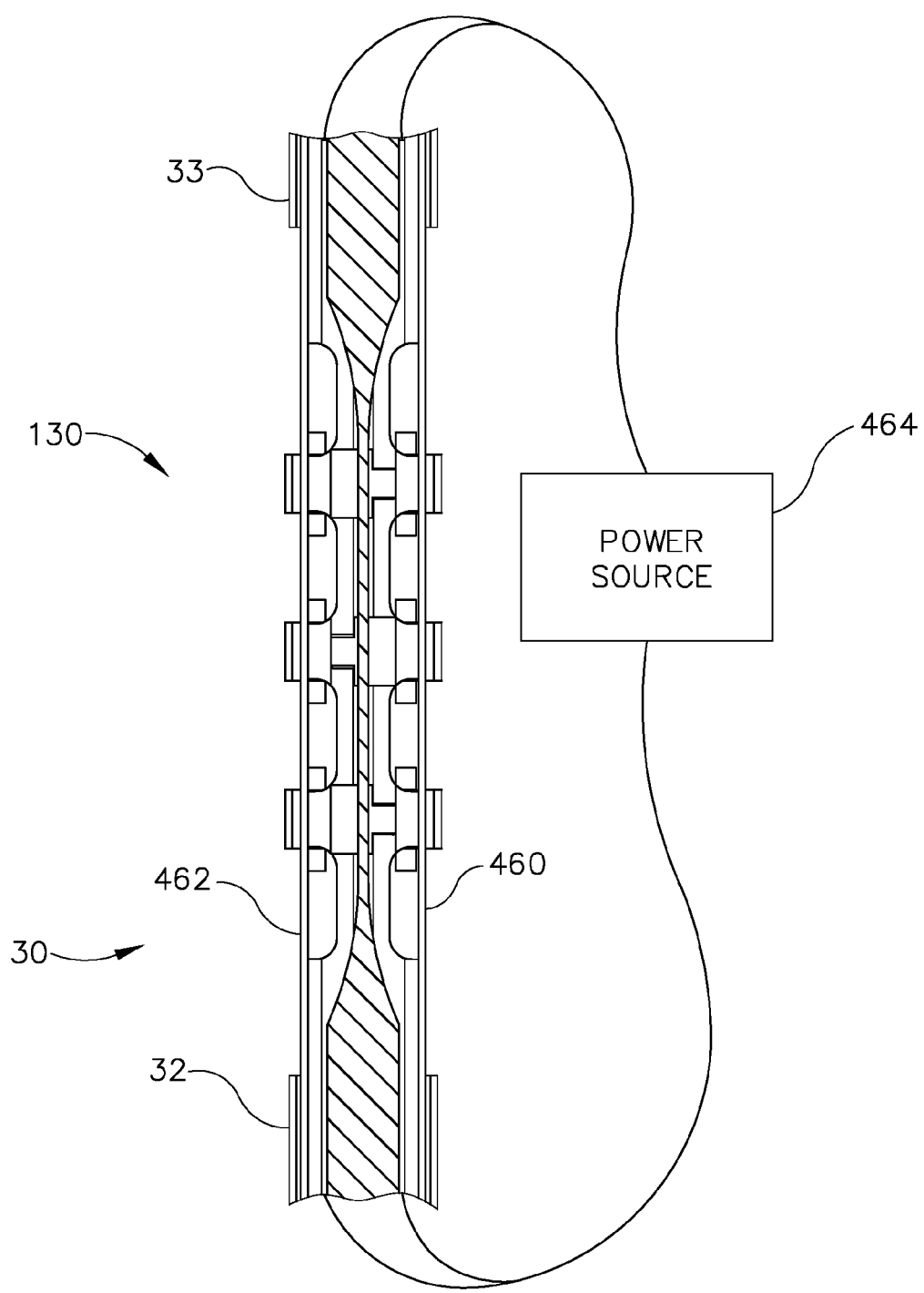
FIG. 47A depicts a detailed cross-sectional top plan view of a modified version of the shaft assembly of FIG. 2 in a straight configuration having yet another exemplary structural feature.
Figure 47B:
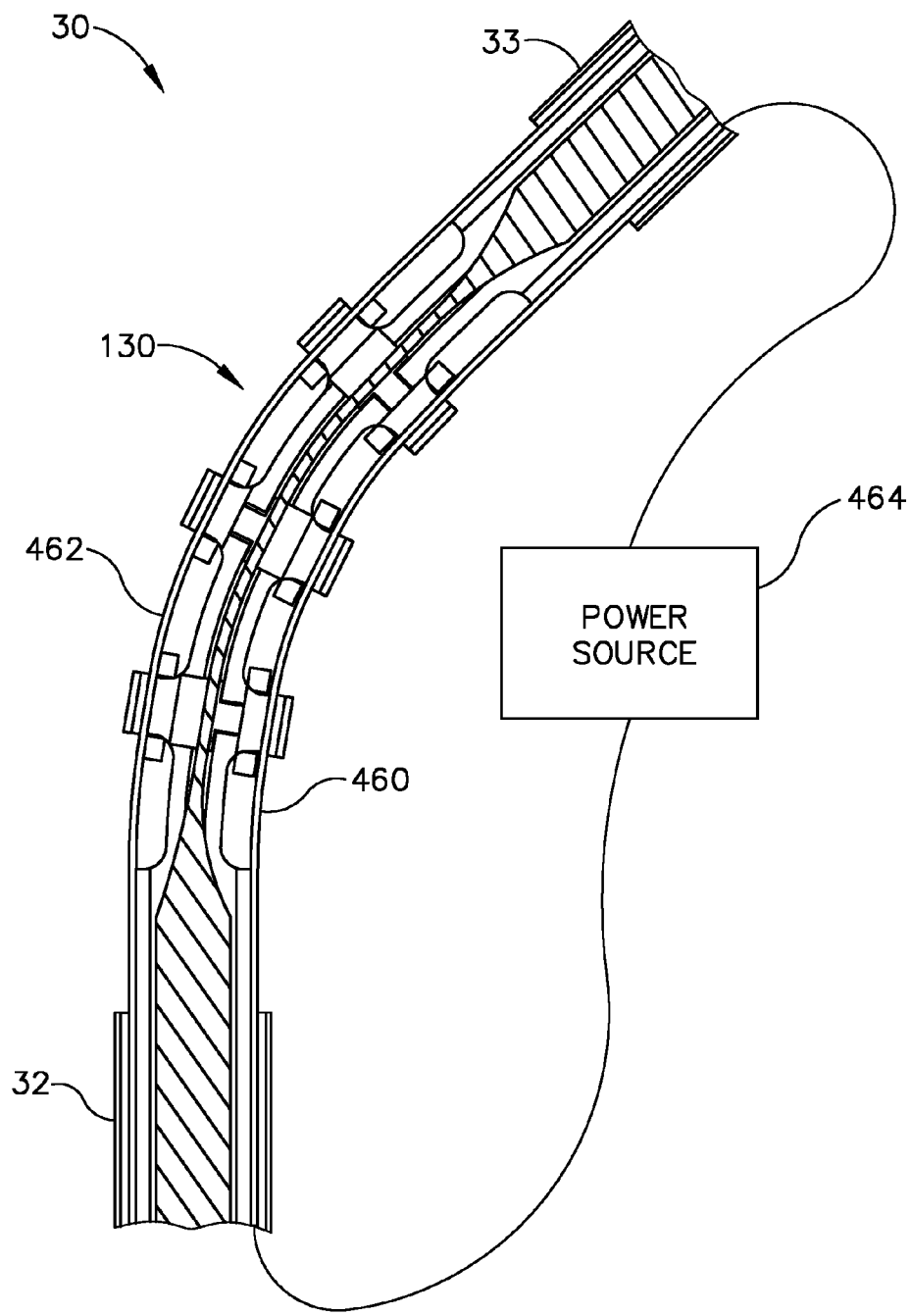
FIG. 47B depicts a detailed cross-sectional top plan view of the modified shaft assembly of FIG. 47A in an articulated configuration.

FIGS. 47A and 47B show a modified version of shaft assembly (30) of instrument (10) described above having a pair of exemplary alternative articulation bands (460, 462). Articulation bands (460, 462) are coupled with a power source (464) that is operable to provide an electrical current to articulation bands (460, 462). Articulation bands (460, 462) of the present example comprise a "smart material" (e.g. "muscle wire" shape memory alloy, electroactive polymer, etc.). In the absence of a current being applied to it, such a "smart material" may be stretched by a small force. Thus, as shown in FIG. 47B, in the absence of a current applied to articulation bands (460, 462), articulation bands (460, 462) may easily flex to thereby allow articulation section (130) to flex so as to deflect end effector (40) relative to outer sheath (32). Once a current is applied to such a "smart material," the material becomes substantially harder and returns to its original length (e.g., a length that is shorter than the length when the current is removed). Thus, as shown in FIG. 47A, once power source (464) provides an electrical current to articulation bands (460, 462), articulation bands (460, 462) become substantially rigid and return to their original (e.g., shorter) lengths so as to provide rigidity to articulation section (130) and/or to prevent inadvertent deflection of end effector (40) relative to outer sheath (32). Various suitable ways in which articulation bands (460, 462) may be selectively activated by power source (464) will be apparent to those of ordinary skill in the art in view of the teachings herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An An apparatus for operating on tissue, the apparatus comprising: (a) a body assembly; (b) a shaft assembly, wherein the shaft assembly extends distally from the body assembly, wherein the shaft assembly defines a longitudinal axis; (c) an end effector, wherein the end effector is located at a distal end of the shaft assembly; (d) an articulation section, wherein the articulation section is coupled with the shaft assembly, wherein the articulation section is operable to flex to thereby deflect the end effector from the longitudinal axis; and (e) a rigidizing member, wherein the rigidizing member is operable to selectively rigidize the articulation section.

Example 2

The apparatus of Example 1 or any of the following Examples, wherein the rigidizing member comprises a collapsible and expandable tube slidably disposed about a portion the shaft assembly and the articulation section.

Example 3

The apparatus of any of the preceding or following Examples, wherein the rigidizing member comprises an inflatable and deflatable balloon disposed about a portion the shaft assembly and the articulation section.

Example 4

The apparatus of any of the preceding or following Examples, wherein the shaft assembly comprises a plurality of couplers pivotably linked to one another, wherein the rigidizing member is configured to selectively engage the plurality of couplers to thereby rigidize the articulation section.

Example 5

The apparatus of Example 4, wherein the rigidizing member comprises an expandable and contractable accordion-like rigidizing member configured to selectively engage the plurality of couplers.

Example 6

The apparatus of Example 4, wherein the rigidizing member comprises a plurality of pegs configured to selectively engage the plurality of couplers.

Example 7

The apparatus of any of the preceding or following Examples, wherein the rigidizing member comprises a plurality of flanges linked to one another by at least one flexible member.

Example 8

The apparatus of Example 7, wherein the flanges of the plurality of flanges comprise a rectangular cross-sectional profile.

Example 9

The apparatus of any of the preceding or following Examples, wherein the rigidizing member comprises rigidizing sleeve member slidably disposed about a portion the shaft assembly and the articulation section.

Example 10

The apparatus of Example 9, wherein the rigidizing sleeve member comprises a plurality of projections, wherein the plurality of projections are configured to selectively engage at least a portion of the articulation section to thereby rigidize the articulation section.

Example 11

The apparatus of any of the preceding or following Examples, wherein the rigidizing member comprises a plurality of C-channel members linked to one another by at least one flexible member.

Example 12

The apparatus of Example 11, wherein the plurality of C-channel members are configured to selectively engage at least a portion of the articulation section to thereby rigidize the articulation section.

Example 13

The apparatus of any of the preceding or following Examples, wherein the rigidizing member comprises a rigidizing clip member selectively coupleable about at least a portion of the articulation section.

Example 14

The apparatus of any of the preceding or following Examples, wherein the rigidizing member comprises at least one pair of overlapping articulation bands, wherein each articulation band of the plurality of structural bands comprises a plurality of weak spots, wherein the overlapping articulation bands are movable relative to each other to selectively align or offset the weak spots to thereby provide flexibility or rigidity to the rigidizing member.

Example 15

The apparatus of any of the preceding or following Examples, wherein the rigidizing member comprises magnetorheological fluid.

Example 16

The apparatus of Example 15, wherein the rigidizing member comprises a valve assembly.

Example 17

The apparatus of any of the preceding or following Examples, wherein the rigidizing member comprises at least one articulation band comprised of smart material, wherein the smart material is configured to change in length in response to application of an electrical current to the smart material.

Example 18

An apparatus for operating on tissue, the apparatus comprising: (a) a body assembly; (b) a shaft assembly, wherein the shaft assembly extends distally from the body assembly, wherein the shaft assembly defines a longitudinal axis; (c) an end effector, wherein the end effector is located at a distal end of the shaft assembly; (d) an articulation section, wherein the articulation section is coupled with the shaft assembly, wherein the articulation section is operable to flex to thereby deflect the end effector from the longitudinal axis; and (e) a rigidizing member, wherein the rigidizing member is operable to selectively engage at least a portion of the articulation section to thereby selectively rigidize the articulation section

Example 19

The apparatus of Example 18, wherein the articulation section comprises a plurality of retention collars, wherein the rigidizing member is operable to selectively engage the retention collars of the articulation section to thereby rigidize the articulation section.

Example 20

An apparatus for operating on tissue, the apparatus comprising: (a) a body assembly; (b) a shaft assembly, wherein the shaft assembly extends distally from the body assembly, wherein the shaft assembly defines a longitudinal axis; (c) an end effector, wherein the end effector is located at a distal end of the shaft assembly; (d) an articulation section, wherein the articulation section is coupled with the shaft assembly, wherein the articulation section is operable to flex to thereby deflect the end effector from the longitudinal axis; and (e) a rigidizing member, wherein the rigidizing member is movable between a first position and a second position, wherein the articulation section is operable to flex to thereby deflect the end effector from the longitudinal axis with the rigidizing member in the first position, wherein the rigidizing member is operable to limit deflection of the end effector by limiting the flexibility of the articulation section with the rigidizing member in the second position.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) a body assembly;
   (b) a shaft assembly, wherein the shaft assembly extends distally from the body assembly, wherein the shaft assembly defines a longitudinal axis;
   (c) an end effector, wherein the end effector is located at a distal end of the shaft assembly;
   (d) an articulation section, wherein the articulation section is coupled with the shaft assembly, wherein the articulation section is operable to deflect the end effector from the longitudinal axis; and
   (e) a rigidizing member, wherein the rigidizing member has a proximal end and a distal end defining a length of the rigidizing member, wherein the length of the rigidizing member is operable to translate relative to the articulation section to thereby selectively rigidize the articulation section.

2. The apparatus of claim 1, wherein the rigidizing member comprises a collapsible and expandable tube slidably disposed about a portion the shaft assembly and the articulation section.

3. The apparatus of claim 1, wherein the rigidizing member comprises an inflatable and deflatable balloon disposed about a portion the shaft assembly and the articulation section.

4. The apparatus of claim 1, wherein the shaft assembly comprises a plurality of couplers pivotably linked to one another, wherein the rigidizing member is configured to selectively engage the plurality of couplers to thereby rigidize the articulation section.

5. The apparatus of claim 4, wherein the rigidizing member comprises an expandable and contractable accordion-like rigidizing member configured to selectively engage the plurality of couplers.

6. The apparatus of claim 4, wherein the rigidizing member comprises a plurality of pegs configured to selectively engage the plurality of couplers.

7. The apparatus of claim 1, wherein the rigidizing member comprises a plurality of flanges linked to one another by at least one flexible member.

8. The apparatus of claim 7, wherein the flanges of the plurality of flanges comprise a rectangular cross-sectional profile.

9. The apparatus of claim 1, wherein the rigidizing member comprises rigidizing sleeve member slidably disposed about a portion the shaft assembly and the articulation section.

10. The apparatus of claim 9, wherein the rigidizing sleeve member comprises a plurality of projections, wherein the plurality of projections are configured to selectively engage at least a portion of the articulation section to thereby rigidize the articulation section.

11. The apparatus of claim 1, wherein the rigidizing member comprises a plurality of C-channel members linked to one another by at least one flexible member.

12. The apparatus of claim 11, wherein the plurality of C-channel members are configured to selectively engage at least a portion of the articulation section to thereby rigidize the articulation section.

13. The apparatus of claim 1, wherein the rigidizing member comprises a rigidizing clip member selectively coupleable about at least a portion of the articulation section.

14. The apparatus of claim 1, wherein the rigidizing member comprises at least one pair of overlapping articulation bands, wherein each articulation band of the at least one pair of overlapping articulation bands comprises a plurality of weak spots, wherein the overlapping articulation bands are movable relative to each other to selectively align or offset the weak spots to thereby provide flexibility or rigidity to the rigidizing member.

15. The apparatus of claim 1, wherein the rigidizing member comprises magnetorheological fluid.

16. The apparatus of claim 15, wherein the rigidizing member comprises a valve assembly.

17. The apparatus of claim 1, wherein the rigidizing member comprises at least one articulation band comprised of smart material, wherein the smart material is configured to change in length in response to application of an electrical current to the smart material.

18. An apparatus for operating on tissue, the apparatus comprising:

(a) a body assembly;
(b) a shaft assembly, wherein the shaft assembly extends distally from the body assembly, wherein the shaft assembly defines a longitudinal axis;
(c) an end effector, wherein the end effector is located at a distal end of the shaft assembly;
(d) an articulation section, wherein the articulation section is coupled with the shaft assembly, wherein the articulation section is operable to deflect the end effector from the longitudinal axis; and
(e) a rigidizing member longitudinally terminating at ends defining a full length, wherein the full length of the rigidizing member is operable to translate relative to the shaft assembly to selectively engage at least a portion of the articulation section to thereby selectively rigidize the articulation section.

19. The apparatus of claim 18, wherein the articulation section comprises a plurality of retention collars, wherein the rigidizing member is operable to selectively engage the retention collars of the articulation section to thereby rigidize the articulation section.

20. An apparatus for operating on tissue, the apparatus comprising:
(a) a body assembly;
(b) a shaft assembly, wherein the shaft assembly extends distally from the body assembly, wherein the shaft assembly defines a longitudinal axis, wherein the shaft assembly further defines a radially interior region;
(c) an end effector, wherein the end effector is located at a distal end of the shaft assembly;
(d) an articulation section, wherein the articulation section is coupled with the shaft assembly, wherein the articulation section is operable to flex to thereby deflect the end effector from the longitudinal axis; and
(e) a rigidizing member located within the radially interior region of the shaft assembly, wherein the rigidizing member is selectively movable within the radially interior region of the shaft assembly between a first position and a second position, wherein the articulation section is operable to flex to thereby deflect the end effector from the longitudinal axis with the rigidizing member in the first position, wherein the rigidizing member is operable to limit deflection of the end effector by limiting the flexibility of the articulation section with the rigidizing member engaging with the articulation section in the second position.

* * * * *